US011667974B2

(12) United States Patent
Firat et al.

(10) Patent No.: US 11,667,974 B2
(45) Date of Patent: Jun. 6, 2023

(54) DIAGNOSTIC, PROGNOSTIC AND THERAPEUTIC USES OF LONG NONCODING RNAS FOR PATHOLOGIES AND TOXICITIES INDUCING HEART DISORDERS

(71) Applicants: Firalis SA, Huningue (FR); Luxembourg Institute of Health, Luxembourg (LU); The University Hospital of Lausanne, Lausanne (CH); The Cardinal Stefan Wyszynski Institute of Cardiology, Warsaw (PL)

(72) Inventors: Hueseyin Firat, Huningue (FR); Sabrina Danilin, Riedisheim (FR); Yvan Devaux, Zoufftgen (FR); Lu Zhang, Metz (FR); Przemyslaw Leszek, Warsaw (PL); Eric Schordan, Wentzwiller (FR); Samir Ounzain, Lausanne (CH); Thierry Pedrazzini, Lausanne (CH)

(73) Assignees: FIRALIS SA, Huningue (FR); LUXEMBOURG INSTITUTE OF HEALTH, Luxembourg (LU); THE UNIVERSITY HOSPITAL OF LAUSANNE, Lausanne (CH); THE CARDINAL STEFA WUSZYNSKI INSTITUTE OF CARDIOLOGY, Warsaw (PL)

( * ) Notice: Subject to any disclaimer, the term of this patent is extended or adjusted under 35 U.S.C. 154(b) by 0 days.

(21) Appl. No.: 16/622,059

(22) PCT Filed: Jun. 12, 2018

(86) PCT No.: PCT/EP2018/065492
§ 371 (c)(1),
(2) Date: Dec. 12, 2019

(87) PCT Pub. No.: WO2018/229046
PCT Pub. Date: Dec. 20, 2018

(65) Prior Publication Data
US 2021/0189491 A1 Jun. 24, 2021

Related U.S. Application Data

(60) Provisional application No. 62/518,418, filed on Jun. 12, 2017.

(51) Int. Cl.
*C12Q 1/6883* (2018.01)
*C12Q 1/686* (2018.01)
(52) U.S. Cl.
CPC ......... *C12Q 1/6883* (2013.01); *C12Q 1/686* (2013.01); *C12Q 2600/178* (2013.01)
(58) Field of Classification Search
CPC .............................................. C12Q 2600/178
See application file for complete search history.

(56) References Cited

FOREIGN PATENT DOCUMENTS

| EP | 2921561 A1 | 9/2015 |
| WO | WO 2015/092020 A2 | 6/2015 |
| WO | WO 2015/162161 A1 | 10/2015 |

OTHER PUBLICATIONS

Thum, T., Facts and updates about cardiovascular non-coding RNAs in heart failure, ESC Heart Failure, vol. 2, pp. 108-111 (Year: 2015).*
Devaux, Y. et al., Long noncoding RNAs in cardiac development and ageing, Nature Reviews, Cardiology, vol. 12, pp. 415-425 (Year: 2015).*
NONHSAT211604.1, pp. 1-3, downloaded from NONCODE database on Apr. 28, 2022 (Year: 2022).*
GenBank Accession No. NR_135480, Uncharacterized lncRNA, pp. 1-2 (Year: 2017).*
LNCipedia, gene ID SP2-AS1, pp. 1-2, downloaded from the database on May 2, 2022 (Year: 2022).*
LncBook, transcript ID HSALNT0241779, pp. 1-5, downloaded from the database on May 2, 2022 (Year: 2022).*
GenBank Accession No. NR_033963, *Homo sapiens* heart tissue-associated transcript 92 (HRAT92) lncRNA, pp. 1-3 (Year: 2017).*
GenBank Accession No. NR_046252, *Homo sapiens* FGD5 antisense RNA1 (FGD5-AS1), transcript variant 2, lncRNA; pp. 1-4 (Year: 2017).*
GenBank Accession No. NR_044993 , *Homo sapiens* GAS6 antisense RNA 2 (head to head) (GAS6-AS2) lncRNA , pp. 1-3 (Year: 2017).*
Lncbook, transcript HSALNT0207435, pp. 1-5, downloaded from the database on May 2, 2022 (Year: 2022).*

(Continued)

*Primary Examiner* — Teresa E Strzelecka
(74) *Attorney, Agent, or Firm* — Hoxie & Associates LLC

(57) ABSTRACT

The present invention provides methods for the diagnosing, monitoring and prognostication of primary and secondary cardiac disorders in a subject based on lncRNA expression. The invention also provides methods for predicting heart failure after myocardial infarction, and differenciation of Ischemic versus non-ischemic Heart Failure. The assessment/quantification of these lncRNAs may also be used as a marker for monitoring drug-induced cardiac toxicities and for the assessment of cardiac involvement during systemic diseases and others disorders/toxicities impacting cardiac function. These lncRNAs are cardiac tissue enriched and may be involved in different cardiac pathophysiological events and represent a potential target for therapeutical approaches.

16 Claims, 7 Drawing Sheets
Specification includes a Sequence Listing.

(56) References Cited

OTHER PUBLICATIONS

GenBank Accession No. NR_027451, *Homo sapiens* non-coding RNA activated by DNA damage (NORAD), pp. 1-4 (Year: 2016).*
Lncbook, transcript ID HSALNT0289380, pp. 1-5, downloaded from the database on May 2, 2022 (Year: 2022).*
GenBank Accession No. NR_024484, *Homo sapiens* long intergenic non-protein coding RNA909 (LINC00909), pp. 1-5 (Year: 2017).*
Lncbook, transcript ID HSALNT0289071, pp. 1-5, downloaded from the database on May 2, 2022 (Year: 2022).*
Hui Zhai, et al., "Expression pattern of genome-scale long noncoding RNA following acute myocardial infarction in Chinese Uyghur patients", OncoTarget, vol. 8, No. 19, (2017).
Gao, J. et al., "The Role and Molecular Mechanism of Non-Coding RNAs in Pathological Cardiac Remodeling," International Journal of Molecular Sciences, 2017, 18(3):1-17.
"Gene: HSPC324, ENSG00000228401—Summary—*Homo sapiens*—Ensembl genome browser 89," Ensembl, May 1, 2017, retrieved from the Internet, date retrieved: Jul. 18, 2018, 1 page, URL: http://may2017.archive.ensembl.org/Homo_sapiens/Gene/Summary?g=ENSG00000228401;r=9:138394717-138394717;t=ENST00000411904.
International Search Report of International Application No. PCT/EP2018/065492, prepared by the International Searching Authority, dated Sep. 24, 2018, 9 pages.
Kataoka, M. et al., "Noncoding RNAs in Cardiovascular Disease," Etiology and Morphogenesis of Congenital Heart Disease, 2016, Chapter 44, 313-317.
Vausort, M. et al., "Long Noncoding RNAs in Patients with Acute Myocardial Infarction," Circulation Research, 2014, 115(7):668-677.
Viereck, J. et al., "Long Noncoding RNAs in Pathological Cardiac Remodeling," Circulation Research, 2017, 120(2):262-264.
Zhai, H. et al., "Expression pattern of genome-scale long noncoding RNA following acute myocardial infarction in Chinese Uyghur patients," Oncotarget, 2017, 8(19):31449-31464.

* cited by examiner

DIAGNOSTIC, PROGNOSTIC AND THERAPEUTIC USES OF LONG NONCODING RNAS FOR PATHOLOGIES AND TOXICITIES INDUCING HEART DISORDERS

CROSS REFERENCE TO RELATED APPLICATIONS

This application is a U.S. national stage application filed under 35 U.S.C. § 371 of International Application No. PCT/EP2018/065492, filed on Jun. 12, 2018, which claims the benefit and priority of U.S. provisional application 62/518,418, filed on Jun. 12, 2017, the contents of each of which are incorporated herein by reference in their entireties.

REFERENCE TO A SEQUENCE LISTING

This application contains a Sequence Listing as a separate part of the disclosure. The Sequence Listing is incorporated herein by reference.

The present invention provides new biomarkers and methods for the diagnosing, monitoring and prognostication of primary and secondary cardiac disorders in a subject based on lncRNA expression. The invention also provides methods for predicting heart failure (HF) after myocardial infarction, or differentiation between Ischemic (ICM) versus non-ischemic (Non-ICM) HF (e.g., dilated cardiomyopathy (DCM)). The assessment/quantification of these lncRNAs in a single mode or in combination with other lncRNAs can also be used as a marker for monitoring drug-induced cardiac toxicities and for the assessment of cardiac involvement during systemic diseases and others disorders/toxicities impacting cardiac function. These lncRNAs are cardiac tissue enriched and may be involved in different pathophysiological events pertaining to cardiac function and represent a potential target for therapeutic approaches. These therapeutic approaches may be inhibitors or activators of these lncRNAs or the products activated or inhibited by these lncRNAs.

FIELD OF THE INVENTION

The present invention provides a list of cardiac associated or cardiac-enriched lncRNAs and methods for monitoring and diagnosing cardiac disorders in a subject based on lncRNA expression. The invention also provides methods for diagnosing different types of HF such as ICM versus Non-ICM (e.g., DCM), methods for predicting HF after myocardial infarction, and for monitoring treatment efficacy and drug-induced cardiac toxicities.

BACKGROUND OF THE INVENTION

In recent years, long non-coding RNA (lncRNAs) have emerged as a new type of non-coding RNA and many studies have shown their potential as powerful biomarkers in varous pathologies such as cancer.

In contrast to other non-coding RNA such as miRNA or snoRNA, lncRNA lack strong whole sequence conservation across different species but rather appear to contain short, highly conserved elements. Despite only a few lncRNA having been shown to be biologically relevant and functionally annotated, there's growing evidence that the majority of them are likely to be functional. While the exact function of most lncRNAs remain unknown, they have been implicated in various biological processes, mainly relating to transcriptional, post-transcriptional and epigenetic regulation. The majority of lncRNAs to date, that are functionally characterized, are believed to regulate developmental processes. However, recent profiling of the mice cardiac transcriptome, after myocardial infarction in mice cardiac tissue, has shown their role in controlling mature tissue as well as the relevance of their expression level in cardiac pathologies. There are publications which have argued for apparent similar roles of certain lncRNAs in humans e.g., WO2015092020, Cardiac disorders such as coronary artery disease (CAD), acute myocardial infarcation (AMI) and heart failure (HF) are leading causes of mortality and morbidity in the world and cardiac toxicities such as those induced by drugs and drug candidates are the most important cause of drug withdrawal. Thus, there is a very important unmet medical need for diverse types of biomarkers for assessing cardiac function, including but not limited to diagnosis, prognosis, monitoring of drug effects and diseases activity. Several cardiac pathologies remain still incurable or need less aggressive and more personalized treatment. lncRNA represent a novel family of targets useful for these diagnostic and therapeutic applications in the cardiovascular area. The present invention relates to lncRNAs that are cardiac enriched and described for the first time in human cardiac tissues. They represent good therapeutic and diagnostic candidates for cardiac related disorders.

SUMMARY OF THE INVENTION

Given that expression levels of lncRNAs could be associated with heart disease in human cardiac biopsies, the inventors set out to characterize lncRNA specifically relevant to cardiac tissue and involved in cardiac remodeling.

The present invention relates to lncRNAs having a sequence selected from the group consisting of SEQ ID NO:1 to SEQ ID NO: 3238 (Human sequences) isoforms thereof, fragments thereof and variant sharing at least 80% nucleotide sequence homology (hereinafter named "lncRNA of the invention") suitable for the diagnosis, prognosis and monitoring of subjects suffering from cardiovascular disorders.

In particular, the invention provides a method for diagnosing and monitoring cardiac disorders, the method comprising determining the level of expression, in a biological sample derived from said subject, of one or more lncRNAs of the invention and calculating differential expression of one of more lncRNAs of the invention compared to one or more lncRNA in a biological sample from a control subject, wherein differential expression of one or more lncRNAs of the invention indicates that the subject has developed or is at risk of developing a cardiac disorder. This method of the invention is also suitable for the prognostication of cardiac disorders.

In another aspect, the invention provides a method for predicting the development of heart failure (HF) in a subject having suffered myocardial infarction, a method for monitoring treatment efficacy in a subject suffering from cardiac injury and receiving a pharmaceutical cardiac therapy, a method for evaluating drug-induced cardiac toxicity in a subject receiving an effective amount of pharmaceutical composition, a method for diagnosing ischemic cardiomyopathy (ICM) in a subject, a method for diagnosing dilated cardiomyopathy (DCM) in a subject, a method for differentiating ICM vs Non-ICM (e.g., DCM) in subjects suffering heart failure, the methods comprising determining the level of expression, in a biological sample derived from said subject, of one or more lncRNAs of the invention and calculating differential expression of one of more lncRNAs of the invention compared to one or more lncRNA in a biological sample from a control subject.

In another aspect, the invention concerns a diagnostic/prognostic kit for carrying out any of the before cited methods.

In still another aspect, the present invention provides a method for treating a cardiac pathology in a subject comprising administering to said subject an effective amount of a pharmaceutical agent modulating the expression of one or more lncRNAs of the invention.

It yet another aspect, the invention provides for a method of detecting one or more lncRNAs (e.g., lncRNAs having a sequence selected from the group consisting of SEQ ID NO: 1 to SEQ ID NO: 3238). In one aspect, the method comprises the step of obtaining the lncRNA from a human biological sample (e.g., a human plasma sample).

In still another aspect, the invention provides a method of obtaining one or more lncRNAs, wherein the method comprises selection and isolation of total RNA. In one aspect, the lncRNA is correlated with the risk or development of a cardiac disorder. In one aspect the lncRNA is obtained from a biological sample (e.g., a cardiac biopsy or blood sample (e.g., plasma sample)).

BRIEF DESCRIPTION OF THE FIGURES

FIG. 3A compares ICM and Control. FIG. 3B compares DCM and Control.

DETAILED DESCRIPTION OF THE INVENTION

Figure 1:
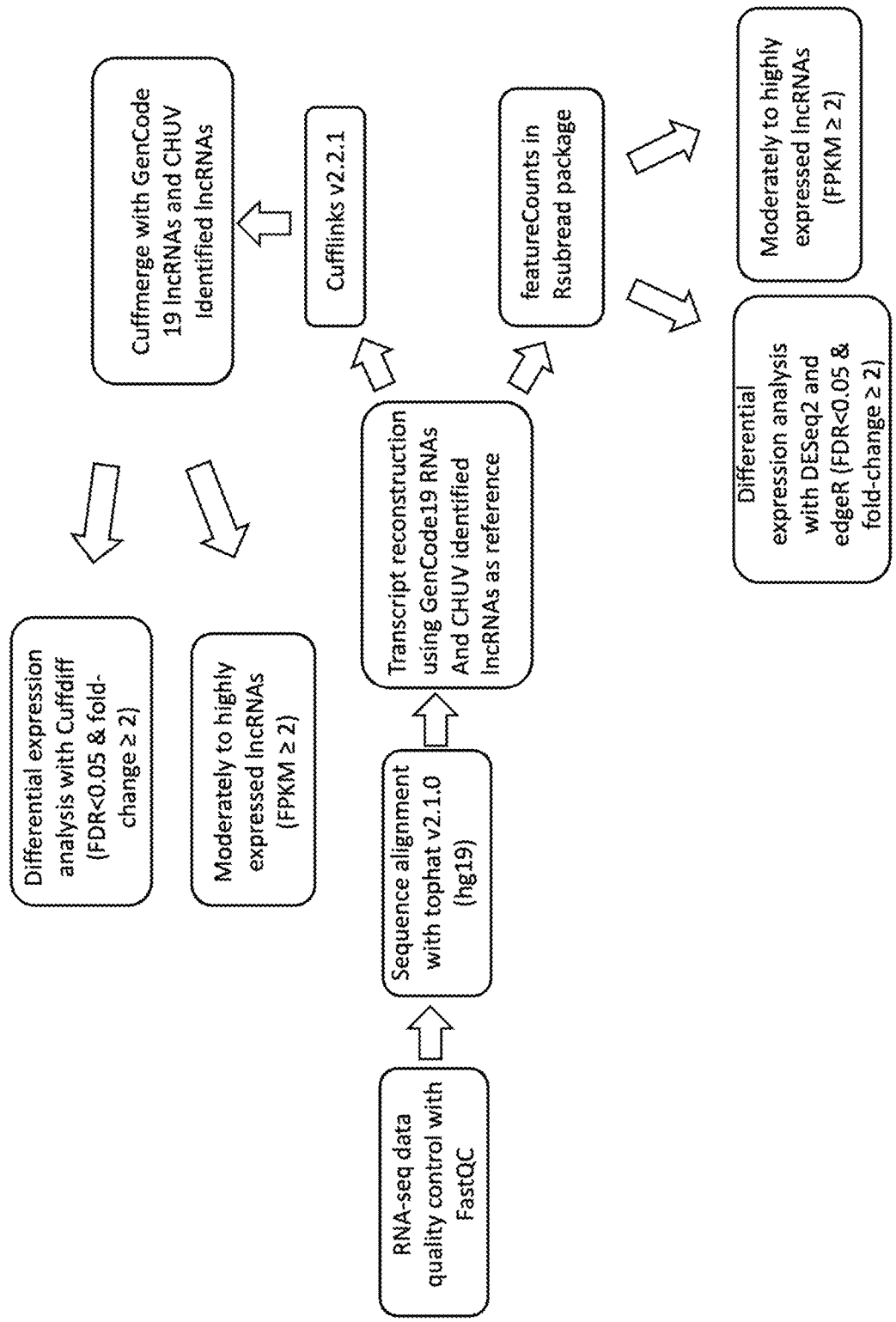
FIG. 1 shows the sequencing data analysis and the selection procedure of known lncRNA relevant to the cardiac pathologies.
Figure 2:
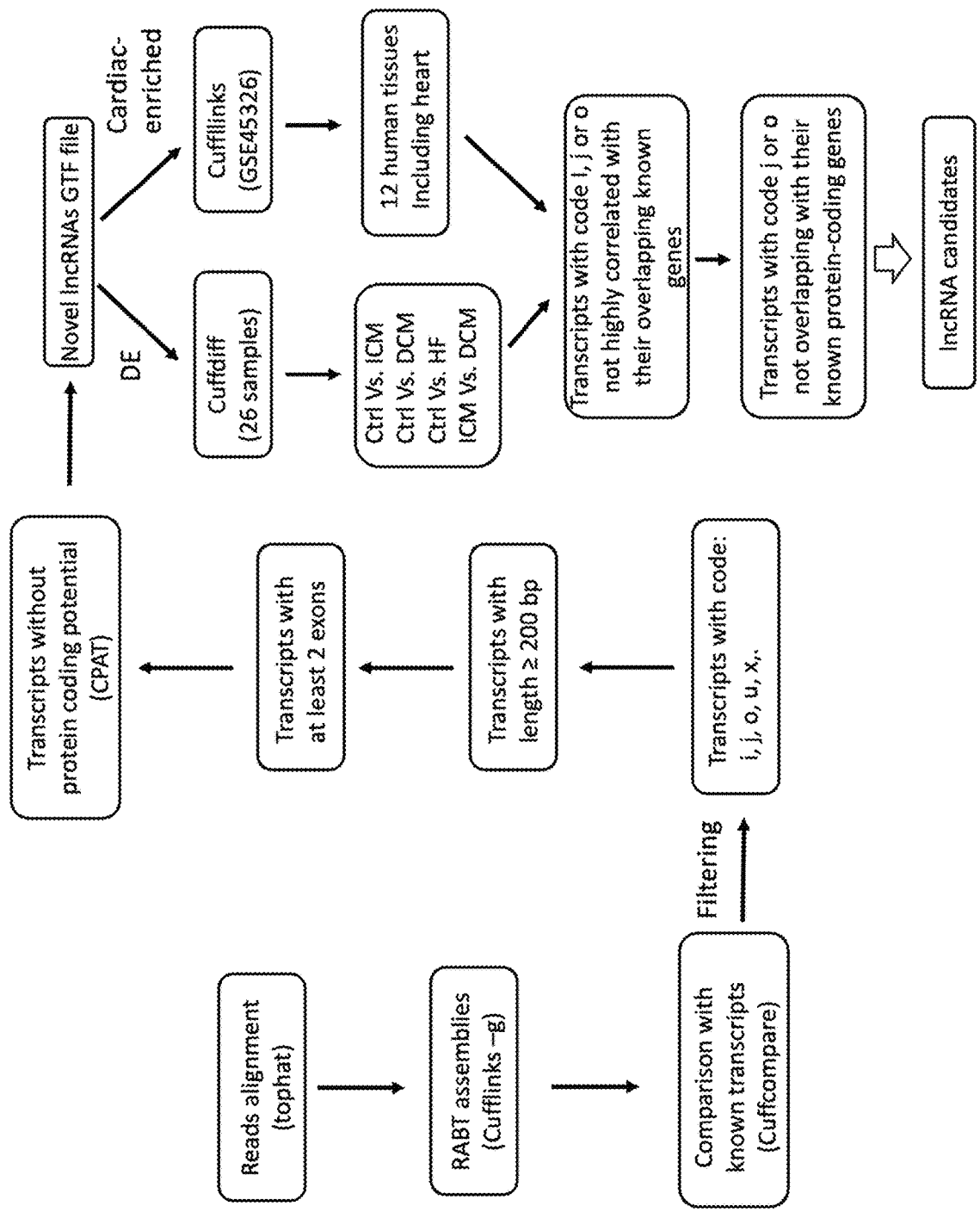
FIG. 2 shows the sequencing data analysis and the selection procedure of novel identified lncRNA relevant to the cardiac pathologies.
Figure 3A:
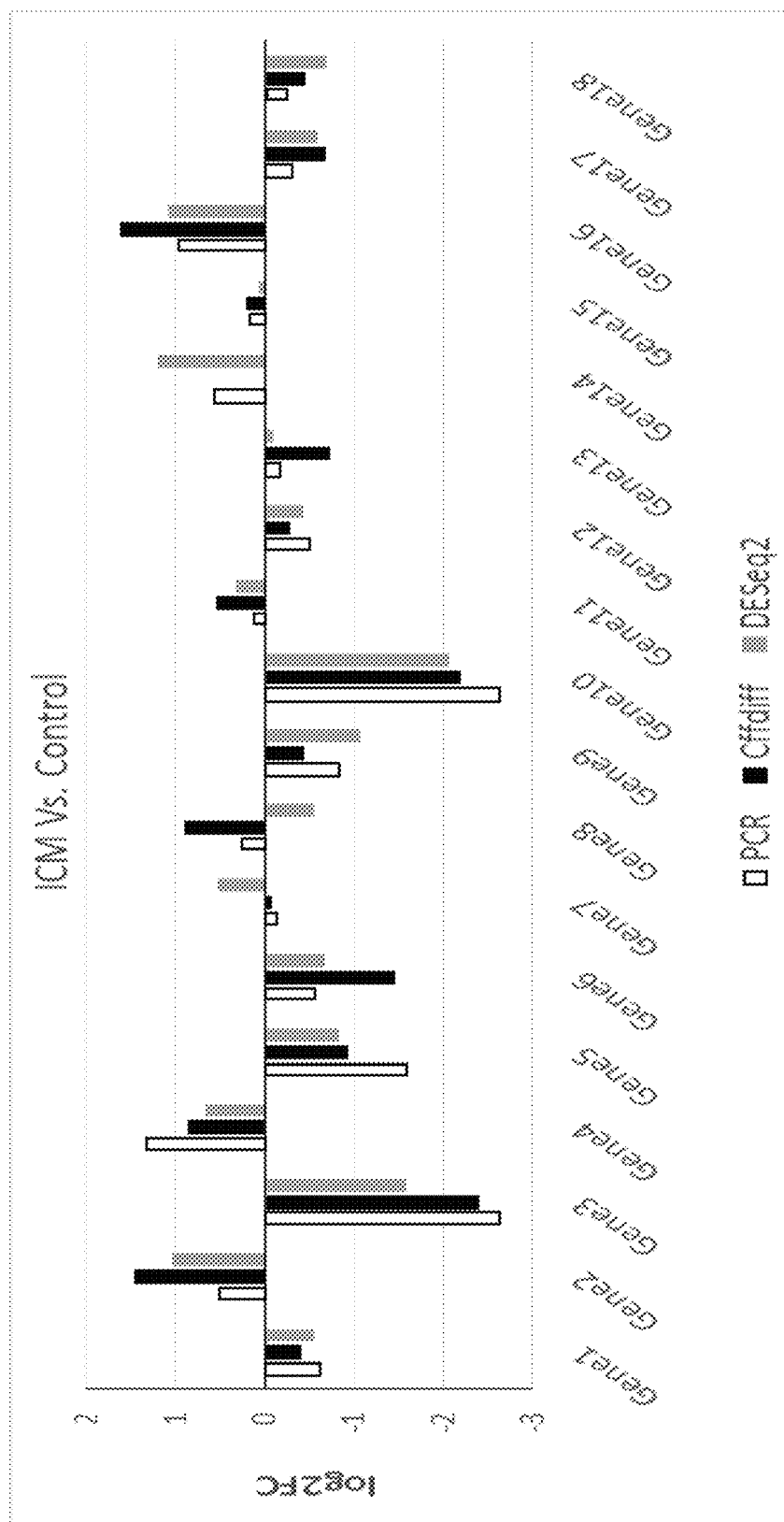
FIGS. 3A and 3B show the correlation between results obtained by sequencing with both Cuffdiff (middle bar) and DeSeq (right bar) analysis and results obtained by PCR (left bar) on patients of the same conditions.
Figure 3B:
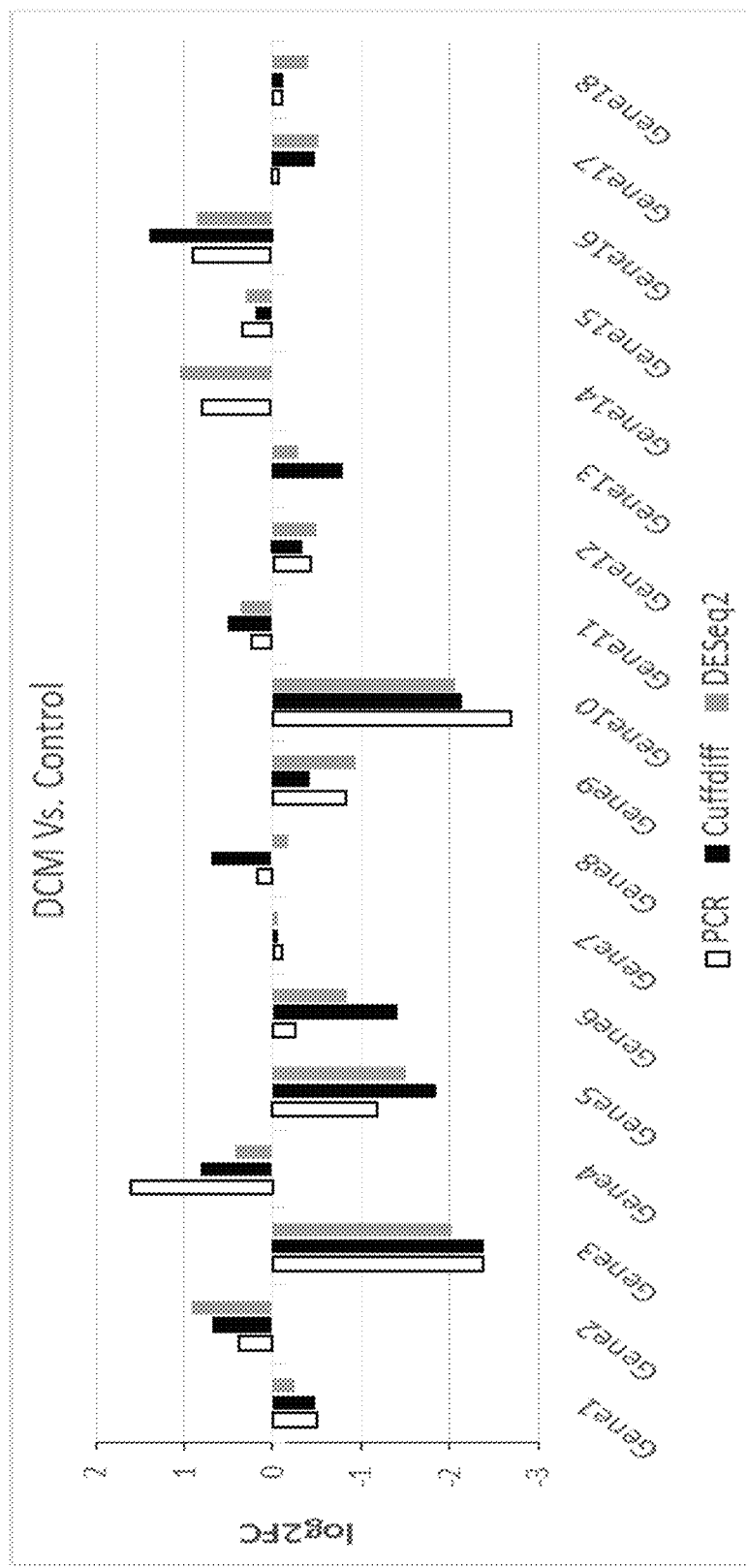

The Inventors intended to characterize the cardiac long non-coding transcriptome and more particularly the dynamically modulated fraction after left ventricular remodeling. The Inventors performed deep RNA-sequencing of cardiac biopsies coupled to novel transcript reconstruction and integration in genome-wide data sets as well as previously characterized predicted human cardiac-specific lncRNA to systematically identify and annotate heart-specific lncRNAs.

Surprisingly, it has been found that the lncRNAs of the invention are highly cardiac and context specific, thus providing a high potential as biomarkers of cardiac disorders as well as pathological response and physiological homeostasis. In addition, using novel transcripts reconstruction, novel lncRNA never described before that are cardiac-enriched and differentially expressed in cardiomyopathies have been found. These findings have been validated by comparing their RNA-Seq data with qPCR data from patients suffering the same conditions. A number of these human lncRNAs are detected in human plasma samples, supporting the feasibility of measuring their expression in patient biofluids for diagnosis and prognosis purposes. Furthermore, the inventors have identified lncRNAs which are differentially expressed in blood sample between the low LVEF (left ventricular ejection fraction) group and the high LVEF group after PCI (Percutaneous Coronary Intervention). Collectively, a novel panel of heart-specific lncRNAs with unique prognosis value relevant to cardiac disorders has been found.

As used herein, a control sample refers to a biological sample such as tissue or cells (e.g., blood sample) from a normal subject (e.g. an individual who does not have cardiac disease or any condition or symptom associated with).

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared times 100. Such alignment can be provided using, for instance, the program Basic Local Alignment Search Tool (BLAST) from the National Center for Biotechnology Information NCBI.

The one or more lncRNAs, fragments thereof, isoforms thereof and variants sharing at least 80% nucleotide sequence identity thereto listed in Table 1 are not part of the present invention. The sequences of these one or more lncRNAs, excluded from the present invention, are described in PCT/EP2014/078868 (Université de Lausanne) and in filed in ST25 format.

TABLE 1

| XLOC_ID | Physiology Cluster | Lnc |
| --- | --- | --- |
| XLOC_007900 | 1 | Lnc7900 |
| XLOC_008052 | 1 | Lnc8052 |
| XLOC_006224 | 1 | Lnc6224 |
| XLOC_013471 | 1 | Lnc13471 |
| XLOC_002075 | 1 | Lnc2075 |
| XLOC_023749 | 1 | Lnc23749 |
| XLOC_008063 | 1 | Lnc8063 |
| XLOC_024203 | 1 | Lnc24203 |
| XLOC_019889 | 1 | Lnc19889 |
| XLOC_008229 | 1 | Lnc8229 |
| XLOC_014116 | 1 | Lnc14116/Novlnc11 |
| XLOC_003166 | 1 | Lnc3166 |
| XLOC_010335 | 1 | Lnc10335 |
| XLOC_021863 | 1 | Lnc21863 |
| XLOC_012367 | 1 | Lnc12367 |

TABLE 1-continued

| XLOC_ID | Physiology Cluster | Lnc |
|---|---|---|
| XLOC_007833 | 1 | Lnc7833 |
| XLOC_023850 | 2 | Lnc23850 |
| XLOC_029624 | 2 | Lnc-TEAD1 |
| XLOC_022865 | 2 | Lnc-SE-22865 |
| XLOC_018239 | 2 | Lnc18239 |
| XLOC_022715 | 2 | Lnc-COL16A1 |
| XLOC_013413 | 2 | Lnc13413 |
| XLOC_005390 | 2 | Lnc-MEOX1 |
| XLOC_010961 | 2 | Lnc-WISP1 |
| XLOC_000709 | 2 | Lnc-TGFB2 |
| XLOC_013407 | 2 | Lnc-SLC8A1 |
| XLOC_020214 | 2 | Lnc-CYR61 |
| XLOC_012723 | 2 | Lnc-SE-12723/Novlnc174 |
| XLOC_022262 | 2 | Lnc22262 |
| XLOC_000719 | 2 | Lnc00719 |
| XLOC_004951 | 2 | Lnc4951 |
| XLOC_026589 | 2 | Lnc26589 |
| XLOC_019010 | 2 | Lnc19010 |
| XLOC_022236 | 2 | Lnc22236 |
| XLOC_011236 | 3 | Lnc-SLC38A2 |
| XLOC_012015 | 3 | Lnc-KCNJ6 |
| XLOC_012884 | 3 | Lnc-NKX2.5 |
| XLOC_004797 | 3 | Lnc4797 |
| XLOC_003851 | 3 | Lnc-SPNB2 |
| XLOC_011237 | 3 | Lnc-SLC38A2 |
| XLOC_014898 | 3 | Lnc-SE-14989 |
| XLOC_030839 | 3 | Lnc-CDH13 |
| XLOC_012194 | 3 | Lnc-ACAP2 |
| XLOC_031308 | 3 | Lnc-IRX3 |
| XLOC_026621 | 3 | Lnc-ATOH8 |
| XLOC_002721 | 3 | Lnc-TXLNB |
| XLOC_003170 | 3 | Lnc-KITLG |
| XLOC_002849 | 4 | Lnc-Novlnc6 |
| XLOC_016279 | 4 | Lnc-Novlnc25 |
| XLOC_024141 | 4 | Lnc-CARD11 |
| XLOC_021524 | 4 | Lnc-NFIB |
| XLOC_021715 | 4 | Lnc-FOXO6 |
| XLOC_020321 | 4 | Lnc-ANX5A |
| XLOC_006274 | 4 | Lnc-MAX |
| XLOC_021416 | 4 | Lnc21416 |
| XLOC_003767 | 4 | Lnc-LIF |
| XLOC_014118 | 4 | Lnc-LCLAT1 |
| XLOC_004833 | 4 | Lnc4833 |
| XLOC_009582 | 4 | Lnc-PPIF |
| XLOC_024449 | 4 | Lnc24449 |
| XLOC_006146 | 4 | Lnc6146 |
| XLOC_033521 | 4 | Lnc-Dedbt (Lnc033521) |
| XLOC_025643 | 4 | Lnc25643 |
| XLOC_004910 | 4 | Lnc-SPARC |
| XLOC_010967 | 4 | Lnc-miR30b |
| XLOC_002503 | 4 | Lnc-SOCS2 |
| XLOC_017764 | 4 | Lnc-ID1 |
| XLOC_020119 | 4 | Lnc20119 |
| XLOC_001065 | 4 | Lnc-GPC1 |
| XLOC_009131 | 4 | Lnc-OTX2 |
| XLOC_000264 | 4 | Lnc-FAM124B |
| XLOC_032325 | 4 | Lnc-TALIN1 |
| XLOC_002546 | 4 | Lnc-KRR1 |
| XLOC_006241 | 4 | Lnc-DACT1 |
| XLOC_029781 | 4 | Lnc29781 |
| XLOC_030722 | 4 | Lnc-SE-30722 |
| XLOC_032031 | 4 | Lnc-KCNJ |
| XLOC_020634 | 4 | Lnc-SE-20634 |
| XLOC_031524 | 4 | Lnc-IRF2BP2 |
| XLOC_020212 | 4 | Lnc-CYR61 |
| XLOC_000336 | 4 | Lnc-HDAC4 |
| XLOC_015960 | 4 | Lnc-ITPRIP |
| XLOC_004067 | 4 | Lnc-MYOCD |
| XLOC_015277 | 4 | Lnc-SMAD7/Novlnc23 |
| XLOC_020313 | 4 | Lnc20313 |
| XLOC_008190 | 4 | Lnc8190 |
| XLOC_033125 | 4 | Lnc33125 |
| XLOC_032788 | 4 | Lnc32788/Novlnc90 |
| XLOC_014917 | 4 | Lnc14917 |
| XLOC_014935 | 4 | Lnc14935 |
| XLOC_007419 | 4 | Lnc7419 |
| XLOC_006561 | 4 | Lnc6561 |
| XLOC_024370 | 4 | Lnc24370 |
| XLOC_006255 | 4 | Lnc6255 |
| XLOC_029637 | 4 | Lnc29637 |
| XLOC_010855 | 2 | Lnc10855 |
| XLOC_007852 | 4 | Lnc7852/Novlnc15 |
| XLOC_009335 | 4 | Lnc9335/Novlnc32 |
| XLOC_019782 | 2 | Lnc19782/Novlnc35 |
| XLOC_010735 | 4 | Lnc10735/Novlnc44 |
| XLOC_007917 | 4 | Lnc7917/Novlnc61 |
| XLOC_033357 | 4 | Lnc33357 |
| XLOC_023848 | 4 | Lnc23848/Novlnc49 |
| XLOC_016979 | 4 | Lnc16979 |

The present invention relates to lncRNAs having a sequence selected from the group consisting of SEQ ID NO: 1 to SEQ ID NO: 3238 (Human sequences) isoforms thereof, fragments thereof and variant sharing at least 80% (e.g., at least 90%, at least 95%, at least 98%, or at least 99%) nucleotide sequence homology suitable for the diagnosis, prognosis and monitoring of subjects suffering from cardiovascular disorders.

In some embodiments, the lncRNA which is detected is selected from any of SEQ ID NO: 1 to SEQ ID NO: 3238.

In some embodiments, the lncRNA which is detected is selected from the group consisting of:
  (i) 15 lncRNAs of SEQ ID NO: 1204, SEQ ID NO: 1736, SEQ ID NO: 0544, SEQ ID NO: 0915, SEQ ID NO:2368, SEQ ID NO: 1595, SEQ ID NO: 2382, SEQ ID NO: 0859, SEQ ID NO: 3112, SEQ ID NO: 1869, SEQ ID NO: 1406, SEQ ID NO: 0043, SEQ ID NO: 0363, SEQ ID NO: 0069 and SEQ ID NO: 1947;
  (ii) 11 lncRNAs of SEQ ID NO: 2373, SEQ ID NO: 1748, SEQ ID NO: 3112, SEQ ID NO: 1231, SEQ ID NO: 0664, SEQ ID NO: 1686, SEQ ID NO: 0791, SEQ ID NO: 2126, SEQ ID NO: 2750, SEQ ID NO: 3010, and SEQ ID NO: 2241;
  (iii) 14 lncRNAs of SEQ ID NO: 2150, SEQ ID NO: 1534, SEQ ID NO: 0311, SEQ ID NO: 2952, SEQ ID NO: 2838, SEQ ID NO: 1437, SEQ ID NO: 1297, SEQ ID NO: 1059, SEQ ID NO: 1465, SEQ ID NO: 2826, SEQ ID NO: 0180, SEQ ID NO: 0538, SEQ ID NO: 0258, and SEQ ID NO: 2273;
  (iv) 20 lncRNAs of SEQ ID NO: 0190, SEQ ID NO: 0359, SEQ ID NO: 0776, SEQ ID NO: 1421, SEQ ID NO: 1795, SEQ ID NO: 0477, SEQ ID NO: 1511, SEQ ID NO: 0435, SEQ ID NO: 1418, SEQ ID NO: 1025, SEQ ID NO: 0265, SEQ ID NO: 1311, SEQ ID NO: 2540, SEQ ID NO: 2323, SEQ ID NO: 3011, SEQ ID NO: 2447, SEQ ID NO: 2863, SEQ ID NO: 2697, SEQ ID NO: 3128, and SEQ ID NO: 2265;
  (v) 11 lncRNAs of SEQ ID NO: 2540, SEQ ID NO: 0545, SEQ ID NO: 1766, SEQ ID NO: 3011, SEQ ID NO: 0968, SEQ ID NO: 2371, SEQ ID NO: 1533, SEQ ID NO: 0749, SEQ ID NO: 0609, SEQ ID NO: 1446, and SEQ ID NO: 2986;
  (vi) 8 lncRNAs of SEQ ID NO: 1204, SEQ ID NO: 2454, SEQ ID NO: 0334, SEQ ID NO: 1403, SEQ ID NO: 1089, SEQ ID NO: 2692, SEQ ID NO: 2273, SEQ ID NO: 0502;
  (vii) 4 lncRNAs of SEQ ID NO: 0097, SEQ ID NO: 1947, SEQ ID NO: 1051 and SEQ ID NO: 2996; and
  (viii) lncRNAs in Table 4, Table 5, Table 8, Table 9, Table 12, Table 15, Table 18, Table 19, Table 20, Table 21, Table 22, Table 24, Table 25, Table 28, Table 29, Table 32, Table 33, Table 34, Table 35, Table 36, Table 37, Table 38, Table 39, Table 40, and/or Table 41.

As used herein, a biological sample may be any sample that may be taken from a subject, such as whole blood, serum, plasma, semen, saliva, tears, urine, fecal material, sweat, buccal smears, skin, cardiac tissue, liver, brain tissue, amniotic fluid, nerve tissue and hair. It also includes specific cellular subtypes or derivatives extracted from those such as PBMCs. The sample used in this invention is preferably blood or cardia tissue, more preferably blood, e.g., serum.

The expression level of lncRNAs may be determined by any technology known by a man skilled in the art. In particular, the expression level of lncRNAs is determined by measuring the amount of nucleic acid transcripts of each lncRNA. The amount of nucleic acid transcripts can be measured by any technology known by a man skilled in the art. The measure may be carried out directly on an extracted RNA sample or on retrotranscribed complementary DNA (cDNA) prepared from extracted RNA by technologies well-known in the art. From the RNA or cDNA sample, the amount of nucleic acid transcripts may be measured using any technology known by a man skilled in the art, including nucleic acid microarrays, quantitative PCR, sequencing (e.g., next generation sequencing), and hybridization with a labeled probe.

In some embodiments, the expression level of lncRNAs is determined using sequencing, e.g., next generation sequencing. Sequencing may be carried out after converting extracted RNA to cDNA using reverse transcriptase or RNA molecules may be directly sequenced. In a particular embodiment, which should not be considered as limiting the scope of the invention, the measurement of the expression level using next generation sequencing may be performed as follows. Briefly, RNA is extracted from a sample (e.g., blood sample). After removing rRNA, RNA samples are then reverse transcribed into cDNA. To ensure strand specificity, single stranded cDNA is first synthetized using Super-Script II reverse transcriptase and random primers in the presence of Actinomycin D, and then converted to double stranded cDNA with the second strand marking mix that incorporates dUTP in place of dTTP. Resulting blunt ended cDNA are purified using AMPure XP magnetic beads. After a 3'end adenylation step, adaptor is attached to cDNA. So obtained cDNA (sequencing library) may be amplified by PCR. The sequencing libraries can be sequenced by any next generation sequencing technology known by a man skilled in the art.

In some embodiments, the measurement of the expression level of lncRNAs, e.g., by sequencing (e.g., next generation sequencing), is facilitated by capturing and enriching nucleic acids (RNA or cDNA) corresponding to lncRNAs of interest prior to the measurement. As used herein, enrichment refers to increasing the percentage of the nucleic acids of interest in the sample relative to the initial sample by selectively purifying the nucleic acids of interest. The enrichment of nucleic acids corresponding to lncRNAs of interest can be carried out on extracted RNA sample or cDNA sample prepared from extracted RNA. In some embodiments, nucleic acids corresponding to lncRNAs of interest are captured and enriched by hybridizing RNA or cDNA sample to oligonucleotide probes specific to lncRNAs of interest (e.g. oligonucleotide probes comprising a sequence complementary to a region of lncRNAs of interest) under conditions allowing for hybridization of the probes and target nucleic acids to form probe-target nucleic acid complexes. Probes may be DNA or RNA, preferably DNA. The length of probes may be from 30 to 80 nucleotides, e.g., from 40 to 70, from 40 to 60, or about 50 nucleotides. The probe-target nucleic acid complexes can be purified by any technology known by a man skilled in the art. In a preferred embodiment, probes are biotinylated. The biotinylated probe-target nucleic acid complexes can be purified by using a streptavidin-coated substrate, e.g, a streptavidin-coated magnetic particle, e.g., T1 streptavidin coated magnetic bead.

In some embodiments, the expression level of lncRNAs may be determined using quantitative PCR. Quantitative, or real-time, PCR is a well known and easily available technology for those skilled in the art and does not need a precise description. In a particular embodiment, which should not be considered as limiting the scope of the invention, the determination of the expression profile using quantitative PCR may be performed as follows. Briefly, the real-time PCR reactions are carried out using the TaqMan Universal PCR Master Mix (Applied Biosystems). 6 µl cDNA is added to a 9 µl PCR mixture containing 7.5 µl TaqMan Universal PCR Master Mix, 0.75 µl of a 20× mixture of probe and primers and 0.75 µl water. The reaction consisted of one initiating step of 2 min at 50 deg. C., followed by 10 min at 95 deg. C., and 40 cycles of amplification including 15 sec at 95 deg. C. and 1 min at 60 deg. C. The reaction and data acquisition can be performed using the ABI 7900HT Fast Real-Time PCR System (Applied Biosystems). The number of template transcript molecules in a sample is determined by recording the amplification cycle in the exponential phase (cycle threshold or $C_Q$ or $C_T$), at which time the fluorescence signal can be detected above background fluorescence. Thus, the starting number of template transcript molecules is inversely related to $C_T$.

In some embodiments, the expression level of lncRNAs may be determined by the use of a nucleic acid microarray. A nucleic acid microarray consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray"), and the oligonucleotides may be about 25 to about 60 base pairs or less in length. To determine the expression profile of a target nucleic acid sample, said sample is labelled, contacted with the microarray in hybridization conditions, leading to the formation of complexes between target nucleic acids that are complementary to probe sequences attached to the microarray surface. The presence of labelled hybridized complexes is then detected. Many variants of the microarray hybridization technology are available to the man skilled in the art.

The present invention provides Method 1. Method 1 is a method of diagnosing or monitoring or treating cardiac diseases or disorders in a subject, the method comprising
  a.) obtaining a sample from said subject;
  b.) detecting the level of expression of one or more lncRNAs (e.g., having a sequence consisting of SEQ ID NO: 1 to SEQ ID NO: 3238, isoforms thereof, fragment thereof and variant sharing at least 80% nucleotide sequence homology); and
  c.) diagnosing the subject with one or mores cardiac diseases or disorders based upon the level of expression of one or more lncRNAs compared to a control, with the proviso that the one or more lncRNAs, fragments thereof, isoforms thereof and variants sharing at least 80% nucleotide sequence identity thereto listed in Table 1 are not part of the present invention.

In various aspects, Method 1 includes the following:
1.1 Method 1, wherein the method wherein the level of expression or the differential expression of one or more said lncRNAs indicates that the subject has developed or is at risk of developing a cardiac disorder.
1.2 Method 1 or 1.1, wherein cardiac disorder is selected from the group consisting of: pathologies or abnormalities with Interventricular Septal Thickness (IVS), heart failure (e.g., left and right ventricle dilatation/dysfunction), EF, LVID, MI, HFrEF, myocardial infarction, myocarditis (e.g., viral myocarditis), cardiac toxicity, brachycardia, arrhythmia, congenital heart defects, hypertension, diabetic cardiomyopathy, idiopathic and dilated cardiomyopathy, pathologies characterized by malformation, pathologies characterized by tissue remodeling, pathologies characterized by affected function, pathologies characterized by disorders of the right heart, pathologies characterized by arrhythmias, pathologies characterized by intoxication, pathologies characterized by cancer, pathologies characterized by neurologic disorders, pathologies characterized by trauma, pathologies characterized by a change in hemodynamic, pathologies characterized by vascular disorders altering cardiac functions such as Coronary artery disease (CAD), and pathologies resulted from cardiac dysfunction/disorders inducing ischemic (embolic/thrombotic) stroke.
1.3 The method of Method 1, 1.1, or 1.2, wherein the diagnosis step includes predicting the development of heart failure in a subject having suffered AMI, the method comprising determining the level of expression, in a biological sample derived from said subject, of one or more lncRNAs of the invention or calculating differential expression of one of more lncRNAs compared to one or more lncRNAs in the same biological sample, wherein the level of expression or the differential expression of one or more said lncRNAs predicts the risk for the subject to develop HF.
1.4 The method of any of Method 1-1.3, wherein the method optionally further comprises the step of administering at least one pharmaceutical to the subject in order to treat one or more cardiovascular diseases or disorders.
1.5 The method of any of Method 1-1.4, wherein the level of expression refers to the differential expression of lncRNAs, the presence of lncRNAs, or the absence of lncRNAs.
1.6 The method of any of Methods 1-1. 5, wherein the level of expression of one or more said lncRNAs indicates that the subject suffers ICM.
1.7 The method of any of Methods 1-1. 5, wherein the level of expression of one or more said lncRNAs indicates that the subject suffers Non-ICM (e.g., DCM).
1.8 The method of any of the preceding methods, wherein the subject has been previously diagnosed with Heart Failure (e.g., congestive heart failure)
1.9 The method of 1.8, wherein the level of expression of one or more said lncRNAs indicates that the subject with Heart Failure also suffers Non-ICM (e.g., DCM).
1.10 Any of the preceding methods, wherein the biological sample is selected from the group consisting of: whole blood, serum, plasma, semen, saliva, tears, urine, fecal material, sweat, buccal smears, skin, cardiac tissue, liver, brain tissue, amniotic fluid, nerve tissue and hair (e.g, wherein the sample is preferably plasma or cardiac tissue).
1.11 Any of the preceding methods, wherein the lncRNA expression levels are detected in a sample (e.g., biological sample) using a technique selected from the group consisting of: S1 nuclease protection assay, microarray analysis, polymerase chain reaction (PCR), hybridization technologies, reverse transcriptase polymerase chain reaction (RT-PCR), Northern blot, serial analysis of gene expression (SAGE), immunoassay, and mass spectrometry.
1.12 Any of the preceding methods, wherein the lncRNA expression level of lncRNA in sample (e.g., biological sample) is detected using a singleplexed or multiplexed method selected from a group consisting of: fluorescence, luminescence, radio-marking, sequencing, e.g., next generation sequencing, and coded microdisks.
1.13 Any of the preceding methods further comprising administering a pharmaceutical composition which modulates one or more lncRNAs, wherein the pharmaceutical composition is selected from the group consisting of: a chemical agent, a RNA mimic, an antibody, an engineered protease, a CRISPR based technology and enzymatically active RNA.
1.14 The method of 1.13, wherein the enzymatically active RNA is selected from the group consisting of: a miRNA, a siRNA, a piRNA, a hnRNA, a snRNA, esiRNA, shRNA, decoys, RNA aptamers and an antisense oligonucleotide.
1.15 Any of the preceding methods, wherein the method is a method of diagnosis.
1.16 Any of the preceding methods, wherein the method is a method of monitoring.
1.17 Any of the preceding methods, wherein the method is a method of treatment.
1.18 Any of the preceding methods, wherein the expression level of the lncRNAs of the invention are detected by measuring the levels of cDNAs, amplified RNAs or DNAs or quantities of DNA probes, or other molecules, in a sample (e.g., biological sample) that are indicative of the expression level of the lncRNA.
1.19 Any of the preceding methods, wherein the lncRNA which is detected is selected from any of SEQ ID NO: 1 to SEQ ID NO: 3238.
1.20 Any of the preceding methods, wherein the lncRNA which is detected is selected from selected from the group consisting of:
  (i) 15 lncRNAs of SEQ ID NO: 1204, SEQ ID NO: 1736, SEQ ID NO: 0544, SEQ ID NO: 0915, SEQ ID NO:2368, SEQ ID NO: 1595, SEQ ID NO: 2382, SEQ ID NO: 0859, SEQ ID NO: 3112, SEQ ID NO: 1869, SEQ ID NO: 1406, SEQ ID NO: 0043, SEQ ID NO: 0363, SEQ ID NO: 0069 and SEQ ID NO: 1947;
  (ii) 11 lncRNAs of SEQ ID NO: 2373, SEQ ID NO: 1748, SEQ ID NO: 3112, SEQ ID NO: 1231, SEQ ID NO: 0664, SEQ ID NO: 1686, SEQ ID NO: 0791, SEQ ID NO: 2126, SEQ ID NO: 2750, SEQ ID NO: 3010, and SEQ ID NO: 2241;
  (iii) 14 lncRNAs of SEQ ID NO: 2150, SEQ ID NO: 1534, SEQ ID NO: 0311, SEQ ID NO: 2952, SEQ ID NO: 2838, SEQ ID NO: 1437, SEQ ID NO: 1297, SEQ ID NO: 1059, SEQ ID NO: 1465, SEQ ID NO: 2826, SEQ ID NO: 0180, SEQ ID NO: 0538, SEQ ID NO: 0258, and SEQ ID NO: 2273;
  (iv) 20 lncRNAs of SEQ ID NO: 0190, SEQ ID NO: 0359, SEQ ID NO: 0776, SEQ ID NO: 1421, SEQ ID NO: 1795, SEQ ID NO: 0477, SEQ ID NO: 1511, SEQ ID NO: 0435, SEQ ID NO: 1418, SEQ ID NO:

1025, SEQ ID NO: 0265, SEQ ID NO: 1311, SEQ ID NO: 2540, SEQ ID NO: 2323, SEQ ID NO: 3011, SEQ ID NO: 2447, SEQ ID NO: 2863, SEQ ID NO: 2697, SEQ ID NO: 3128, and SEQ ID NO: 2265;
(v) 11 lncRNAs of SEQ ID NO: 2540, SEQ ID NO: 0545, SEQ ID NO: 1766, SEQ ID NO: 3011, SEQ ID NO: 0968, SEQ ID NO: 2371, SEQ ID NO: 1533, SEQ ID NO: 0749, SEQ ID NO: 0609, SEQ ID NO: 1446, and SEQ ID NO: 2986;
(vi) 8 lncRNAs of SEQ ID NO: 1204, SEQ ID NO: 2454, SEQ ID NO: 0334, SEQ ID NO: 1403, SEQ ID NO: 1089, SEQ ID NO: 2692, SEQ ID NO: 2273, SEQ ID NO: 0502;
(vii) 4 lncRNAs of SEQ ID NO: 0097, SEQ ID NO: 1947, SEQ ID NO: 1051 and SEQ ID NO: 2996; and
(viii) lncRNAs in Table 4, Table 5, Table 8, Table 9, Table 12, Table 15, Table 18, Table 19, Table 20, Table 21, Table 22, Table 24, Table 25, Table 28, Table 29, Table 32, Table 33, Table 34, Table 35, Table 36, Table 37, Table 38, Table 39, Table 40, and/or Table 41.

1.21 Any of the preceding methods, wherein the expression level of lncRNA (e.g., SEQ ID NO: 1 to SEQ ID NO: 3238) is compared to a control.

1.22 Any of the preceding methods, wherein cardiac disorder can be selected from the group consisting of: pathologies or abnormalities related to heart failure (HF) e.g., left and right ventricle dilatation/dysfunction, reduced ejection fraction (HFrEF), independently from HF etiology: ICM (Ischemic HF-related with coronary artery disease, myocardial infarction, etc.) vs Non-ICM (Non-Ischemic HF-related with myocarditis, cardiac toxicity, arrhythmia, hypertension, congenital heart defects, diabetic, idiopathic cardiomyopathy or others).

The invention also provides Method 2. Method 2 is a method for monitoring treatment efficacy in a subject suffering from a cardiac disease or disorder and receiving a pharmaceutical cardiac therapy, the method comprising
a.) administering a pharmaceutical to a subject suffering from cardiac injury;
b.) obtaining a sample (e.g., a biological sample) from the subject;
c.) detecting the level of expression of one or more lncRNAs (e.g., having a sequence selected from the group consisting of SEQ ID NO: 1 to SEQ ID NO: 3238, isoforms thereof, fragment thereof and variant sharing at least 80% nucleotide sequence homology) in the sample, wherein the expression level of lncRNA is compared to a control; and
d.) determining the level of expression of one or more lncRNAs, wherein the level of expression of said one or more lncRNAs indicates the efficacy of the treatment,
with the proviso that the one or more lncRNAs, fragments thereof, isoforms thereof and variants sharing at least 80% nucleotide sequence identity thereto listed in Table 1 are not part of the present invention.

In various aspects, Method 2 includes the following:
2.1 Method 2, wherein the level of expression of one or more said lncRNAs indicates that the subject has developed or is at risk of developing a cardiac disorder despite the administration of a pharmaceutical.
2.2 Method 2 or 2.1, wherein cardiac disorder is selected from the group consisting of: pathologies or abnormalities with Interventricular Septal Thickness (IVS), heart failure (e.g., left and right ventricle dilatation/dysfunction), EF, LVID, MI, HFrEF, myocardial infarction, myocarditis (e.g., viral myocarditis), cardiac toxicity, brachycardia, arrhythmia, congenital heart defects, hypertension, diabetic cardiomyopathy, idiopathic and dilated cardiomyopathy, pathologies characterized by malformation, pathologies characterized by tissue remodeling, pathologies characterized by affected function, pathologies characterized by disorders of the right heart, pathologies characterized by arrhythmias, pathologies characterized by intoxication, pathologies characterized by cancer, pathologies characterized by neurologic disorders, pathologies characterized by trauma, pathologies characterized by a change in hemodynamic, pathologies characterized by vascular disorders altering cardiac functions such as Coronary artery disease (CAD), and pathologies resulted from cardiac dysfunction/disorders inducing ischemic (embolic/thrombotic) stroke.
2.3 The method of Method 2, 2.1, or 2.2, wherein the diagnosis step includes predicting the development of heart failure in a subject having suffered AMI, the method comprising determining the level of expression, in a biological sample derived from said subject, of one or more lncRNAs of the invention or calculating differential expression of one of more lncRNAs compared to one or more lncRNAs in the same biological sample, wherein the level of expression or the differential expression of one or more said lncRNAs predicts the risk for the subject to develop HF.
2.4 The method of any of Method 2-2.3, wherein the method optionally further comprises the step of administering at least one pharmaceutical to the subject depending on the efficacy of the treatment.
2.5 The method of any of Method 2-2.4, wherein the level of expression refers to the differential expression of lncRNAs, the presence of lncRNAs, or the absence of lncRNAs.
2.6 The method of any of the preceding methods, wherein the subject has been previously diagnosed with Heart Failure (e.g., congestive heart failure)
2.7 Any of the preceding methods, wherein the biological sample is selected from the group consisting of: whole blood, serum, plasma, semen, saliva, tears, urine, fecal material, sweat, buccal smears, skin, cardiac tissue, liver, brain tissue, amniotic fluid, nerve tissue and hair (e.g, wherein the sample is preferably plasma or cardiac tissue).
2.8 Any of the preceding methods, wherein the lncRNA expression levels are measured by technique selected from the group consisting of: Si nuclease protection assay, microarray analysis, polymerase chain reaction (PCR), hybridization technologies, reverse transcriptase polymerase chain reaction (RT-PCR), Northern blot, serial analysis of gene expression (SAGE), immunoassay, and mass spectrometry.
2.9 Any of the preceding methods, wherein the lncRNA expression level is detected using a singleplexed or multiplexed method selected from a group consisting of: fluorescence, luminescence, radio-marking, next generation sequencing and coded microdisks.
2.10 Any of the preceding methods further comprising administering a pharmaceutical composition which modulates one or more lncRNAs, wherein the pharmaceutical composition is selected from the group consisting of: a chemical agent, a RNA mimic, an antibody, an engineered protease, a CRISPR based technology and enzymatically active RNA.

2.11 The method of 2.10, wherein the enzymatically active RNA is selected from the group consisting of: a miRNA, a siRNA, a piRNA, a hnRNA, a snRNA, esiRNA, shRNA, decoys, RNA aptamers and an antisense oligonucleotide.

2.12 Any of the preceding methods, wherein the expression level of the lncRNAs of the invention are determined by measuring the levels of cDNAs, amplified RNAs or DNAs or quantities of DNA probes, or other molecules that are indicative of the expression level of the lncRNA.

2.13 Any of the preceding methods, wherein the lncRNA which is detected is selected from any of SEQ ID NO: 1 to SEQ ID NO: 3238.

2.14 Any of the preceding methods, wherein the lncRNA which is detected is selected from selected from the group consisting of:
- (i) 15 lncRNAs of SEQ ID NO: 1204, SEQ ID NO: 1736, SEQ ID NO: 0544, SEQ ID NO: 0915, SEQ ID NO:2368, SEQ ID NO: 1595, SEQ ID NO: 2382, SEQ ID NO: 0859, SEQ ID NO: 3112, SEQ ID NO: 1869, SEQ ID NO: 1406, SEQ ID NO: 0043, SEQ ID NO: 0363, SEQ ID NO: 0069 and SEQ ID NO: 1947;
- (ii) 11 lncRNAs of SEQ ID NO: 2373, SEQ ID NO: 1748, SEQ ID NO: 3112, SEQ ID NO: 1231, SEQ ID NO: 0664, SEQ ID NO: 1686, SEQ ID NO: 0791, SEQ ID NO: 2126, SEQ ID NO: 2750, SEQ ID NO: 3010, and SEQ ID NO: 2241;
- (iii) 14 lncRNAs of SEQ ID NO: 2150, SEQ ID NO: 1534, SEQ ID NO: 0311, SEQ ID NO: 2952, SEQ ID NO: 2838, SEQ ID NO: 1437, SEQ ID NO: 1297, SEQ ID NO: 1059, SEQ ID NO: 1465, SEQ ID NO: 2826, SEQ ID NO: 0180, SEQ ID NO: 0538, SEQ ID NO: 0258, and SEQ ID NO: 2273;
- (iv) 20 lncRNAs of SEQ ID NO: 0190, SEQ ID NO: 0359, SEQ ID NO: 0776, SEQ ID NO: 1421, SEQ ID NO: 1795, SEQ ID NO: 0477, SEQ ID NO: 1511, SEQ ID NO: 0435, SEQ ID NO: 1418, SEQ ID NO: 1025, SEQ ID NO: 0265, SEQ ID NO: 1311, SEQ ID NO: 2540, SEQ ID NO: 2323, SEQ ID NO: 3011, SEQ ID NO: 2447, SEQ ID NO: 2863, SEQ ID NO: 2697, SEQ ID NO: 3128, and SEQ ID NO: 2265;
- (v) 11 lncRNAs of SEQ ID NO: 2540, SEQ ID NO: 0545, SEQ ID NO: 1766, SEQ ID NO: 3011, SEQ ID NO: 0968, SEQ ID NO: 2371, SEQ ID NO: 1533, SEQ ID NO: 0749, SEQ ID NO: 0609, SEQ ID NO: 1446, and SEQ ID NO: 2986;
- (vi) 8 lncRNAs of SEQ ID NO: 1204, SEQ ID NO: 2454, SEQ ID NO: 0334, SEQ ID NO: 1403, SEQ ID NO: 1089, SEQ ID NO: 2692, SEQ ID NO: 2273, SEQ ID NO: 0502;
- (vii) 4 lncRNAs of SEQ ID NO: 0097, SEQ ID NO: 1947, SEQ ID NO: 1051 and SEQ ID NO: 2996; and
- (viii) lncRNAs in Table 4, Table 5, Table 8, Table 9, Table 12, Table 15, Table 18, Table 19, Table 20, Table 21, Table 22, Table 24, Table 25, Table 28, Table 29, Table 32, Table 33, Table 34, Table 35, Table 36, Table 37, Table 38, Table 39, Table 40, and/or Table 41.

2.15 Any of the preceding methods, wherein cardiac disorder can be selected from the group consisting of: pathologies or abnormalities related to heart failure (HF) e.g., left and right ventricle dilatation/dysfunction, reduced ejection fraction (HFrEF), independently from HF etiology: ICM (Ischemic HF-related with coronary artery disease, myocardial infarction, etc.) vs Non-ICM (Non-Ischemic HF-related with myocarditis, cardiac toxicity, arrhythmia, hypertension, congenital heart defects, diabetic, idiopathic cardiomyopathy or others).

The invention also provides for Method 3. Method 3 is a method for diagnosing drug-induced cardiac toxicity in a subject receiving a pharmaceutical composition, wherein the method comprises
- a.) obtaining a sample from the subject;
- b.) measuring the level of expression, (e.g., in a biological sample derived from said subject) of one or more lncRNAs of the invention from the sample
- c.) diagnosing the subject as having a cardiac toxicity from the pharmaceutical composition depending upon the level of expression of one or more said lncRNAs (e.g, wherein the lncRNA is one or more sequences selected from SEQ ID NO: 1 to SEQ ID NO: 3238), with the proviso that the one or more lncRNAs, fragments thereof, isoforms thereof and variants sharing at least 80% nucleotide sequence identity thereto listed in Table 1 are not part of the present invention.

The invention also provides for Method 4. Method 4 is a method of detecting one or more lncRNAs (e.g., lncRNAs having a sequence selected from the group consisting of SEQ ID NO: 1 to SEQ ID NO: 3238) useful for Method 1 et seq, Method 2 et seq, and Method 3 et seq. In one aspect, the method comprises the step of obtaining the lncRNA from a human biological sample (e.g., a human plasma sample). The sample can be any biological sample as described in Method 1 et seq, Method 2 et seq, and Method 3 et seq. Method 4 comprises:
- a.) obtaining a sample (e.g., biological sample) from a subject; and
- b.) measuring the expression level of the lncRNA (e.g, wherein the lncRNA is detected by sequencing (e.g., next generation sequencing), 51 nuclease protection assay, microarray analysis, polymerase chain reaction (PCR), hybridization technologies, reverse transcriptase polymerase chain reaction (RT-PCR), Northern blot, serial analysis of gene expression (SAGE), immunoassay, and mass spectrometry) (e.g, wherein the lncRNA is one or more sequences selected from SEQ ID NO: 1 to SEQ ID NO: 3238), with the proviso that the lncRNAs, fragments thereof, isoforms thereof and variants sharing at least 80% nucleotide sequence identity thereto listed in Table 1 are not part of the present invention.

In various aspects, Method 4 includes the following:

4.1 Method 4, wherein the expression level of the lncRNA is measured by sequencing (e.g., next generation sequencing).

4.2 The method of any of the preceding methods, wherein measuring the expression level of the lncRNA comprises the steps of:
- (i) extracting RNA from the sample (e.g., blood sample),
- (ii) converting the RNA to cDNA,
- (iii) optionally, amplifying the cDNA by PCR, and
- (iv) sequencing the cDNA.

4.3 The method of any of the preceding methods further comprising a step of capturing and enriching extracted RNA or cDNA corresponding to lncRNAs of interest prior to sequencing, comprising the steps of:
- (1) hybridizing extracted RNA or cDNA to oligonucleotide probes specific to lncRNAs of interest (e.g., oligonucleotide probes comprising a sequence complementary to a region of lncRNAs of interest)

under a condition allowing for hybridization of the probes and RNA or cDNA corresponding to lncRNAs of interest to form probe-target nucleic acid complexes, and (2) purifying the probe-target nucleic acid complexes.

4.4 The method of Method 4.3 wherein oligonucleotide probes are hybridized to cDNA.

4.5 The method of any of Methods 4.3-4.4 wherein the oligonucleotide probe is biotinylated and purifying the probe-target nucleic acid complexes comprises binding the probe-target nucleic acid complexes to a streptavidin-coated substrate.

4.6 The method of Method 4.5 wherein the streptavidin-coated substrate is a streptavidin coated magnetic particle, e.g., T1 streptavidin coated magnetic bead.

4.7 The method of any of the preceding methods wherein the sample is blood sample.

4.8 Any of the preceding methods, wherein the lncRNA which is detected is selected from selected from the group consisting of:
  (i) 15 lncRNAs of SEQ ID NO: 1204, SEQ ID NO: 1736, SEQ ID NO: 0544, SEQ ID NO: 0915, SEQ ID NO:2368, SEQ ID NO: 1595, SEQ ID NO: 2382, SEQ ID NO: 0859, SEQ ID NO: 3112, SEQ ID NO: 1869, SEQ ID NO: 1406, SEQ ID NO: 0043, SEQ ID NO: 0363, SEQ ID NO: 0069 and SEQ ID NO: 1947;
  (ii) 11 lncRNAs of SEQ ID NO: 2373, SEQ ID NO: 1748, SEQ ID NO: 3112, SEQ ID NO: 1231, SEQ ID NO: 0664, SEQ ID NO: 1686, SEQ ID NO: 0791, SEQ ID NO: 2126, SEQ ID NO: 2750, SEQ ID NO: 3010, and SEQ ID NO: 2241;
  (iii) 14 lncRNAs of SEQ ID NO: 2150, SEQ ID NO: 1534, SEQ ID NO: 0311, SEQ ID NO: 2952, SEQ ID NO: 2838, SEQ ID NO: 1437, SEQ ID NO: 1297, SEQ ID NO: 1059, SEQ ID NO: 1465, SEQ ID NO: 2826, SEQ ID NO: 0180, SEQ ID NO: 0538, SEQ ID NO: 0258, and SEQ ID NO: 2273;
  (iv) 20 lncRNAs of SEQ ID NO: 0190, SEQ ID NO: 0359, SEQ ID NO: 0776, SEQ ID NO: 1421, SEQ ID NO: 1795, SEQ ID NO: 0477, SEQ ID NO: 1511, SEQ ID NO: 0435, SEQ ID NO: 1418, SEQ ID NO: 1025, SEQ ID NO: 0265, SEQ ID NO: 1311, SEQ ID NO: 2540, SEQ ID NO: 2323, SEQ ID NO: 3011, SEQ ID NO: 2447, SEQ ID NO: 2863, SEQ ID NO: 2697, SEQ ID NO: 3128, and SEQ ID NO: 2265;
  (v) 11 lncRNAs of SEQ ID NO: 2540, SEQ ID NO: 0545, SEQ ID NO: 1766, SEQ ID NO: 3011, SEQ ID NO: 0968, SEQ ID NO: 2371, SEQ ID NO: 1533, SEQ ID NO: 0749, SEQ ID NO: 0609, SEQ ID NO: 1446, and SEQ ID NO: 2986;
  (vi) 8 lncRNAs of SEQ ID NO: 1204, SEQ ID NO: 2454, SEQ ID NO: 0334, SEQ ID NO: 1403, SEQ ID NO: 1089, SEQ ID NO: 2692, SEQ ID NO: 2273, SEQ ID NO: 0502;
  (vii) 4 lncRNAs of SEQ ID NO: 0097, SEQ ID NO: 1947, SEQ ID NO: 1051 and SEQ ID NO: 2996; and
  (viii) lncRNAs in Table 4, Table 5, Table 8, Table 9, Table 12, Table 15, Table 18, Table 19, Table 20, Table 21, Table 22, Table 24, Table 25, Table 28, Table 29, Table 32, Table 33, Table 34, Table 35, Table 36, Table 37, Table 38, Table 39, Table 40, and/or Table 41.

The invention also provides for Method 5. Method 5 is a method for identifying lncRNA from a sample (e.g., a biological sample as described in any of Method 1 et seq, Method 2 et seq, and Method 3 et seq.), wherein the lncRNA can be used to treat, diagnose, and/or predict primary and secondary cardiac disorder(s) in a subject. The method comprises
  a.) isolating total RNA from the biological sample (e.g. cardiac biopsy, serum, or plasma)
  b.) sequencing total RNA from the sample and determining which are lncRNA; and
  c.) comparing the expression (e.g., either relative levels or presence or absence) of lncRNA to a control;
wherein the expression of the lncRNA, compared to a control, means that the lncRNA can be indicative of primary and secondary cardiac disorder(s) in a subject, with the proviso that the one or more lncRNAs, fragments thereof, isoforms thereof and variants sharing at least 80% nucleotide sequence identity thereto listed in Table 1 are not part of the present invention.

Method 5 uses any detection method described in Method 1 et seq, Method 2, et seq, Method 3, et seq., and/or Method 4 et seq.

In still a further aspect, the present invention also encompasses a diagnostic/prognostic kit for carrying out any of the previously cited methods (any of Method 1 et seq, Method 2, et seq, Method 3, et seq., and/or Method 4 et seq and/or Method 5 et seq.). In some embodiments, the diagnostic/prognostic kit comprises one or more oligonucleotide probes specific to lncRNAs of interest (e.g., lncRNAs selected from the group consisting of SEQ ID NO: 1 to SEQ ID NO: 3238, isoforms thereof, fragment thereof and variant sharing at least 80% nucleotide sequence homology) and a reagent for purifying the probe-target nucleic acid complexes. The oligonucleotide probes comprise a sequence complementary to a region of the lncRNAs of interest. The oligonucleotide probes may be DNA or RNA. The oligonucleotide probes are preferably DNA. The length of oligonucleotide probes may be from 30 to 80 nucleotides, e.g., from 40 to 70, from 40 to 60, or about 50 nucleotides. In a preferred embodiment, the oligonucleotide probes are biotinylated and the reagent for purifying the probe-target complexes is a streptavidin-coated substrate, e.g, a streptavidin-coated magnetic particle, e.g., T1 streptavidin coated magnetic bead.

In some embodiments, the diagnostic/prognostic kit comprises one or more oligonucleotide probes specific to one or more lncRNAs (i.e., oligonucleotide probes comprising a sequence complementary to a region of the lncRNAs of interest) selected from any of SEQ ID NO: 1 to SEQ ID NO: 3238.

In some embodiments, the diagnostic/prognostic kit comprises one or more oligonucleotide probes specific to one or more lncRNAs selected from the group consisting of:
  (i) 15 lncRNAs of SEQ ID NO: 1204, SEQ ID NO: 1736, SEQ ID NO: 0544, SEQ ID NO: 0915, SEQ ID NO:2368, SEQ ID NO: 1595, SEQ ID NO: 2382, SEQ ID NO: 0859, SEQ ID NO: 3112, SEQ ID NO: 1869, SEQ ID NO: 1406, SEQ ID NO: 0043, SEQ ID NO: 0363, SEQ ID NO: 0069 and SEQ ID NO: 1947;
  (ii) 11 lncRNAs of SEQ ID NO: 2373, SEQ ID NO: 1748, SEQ ID NO: 3112, SEQ ID NO: 1231, SEQ ID NO: 0664, SEQ ID NO: 1686, SEQ ID NO: 0791, SEQ ID NO: 2126, SEQ ID NO: 2750, SEQ ID NO: 3010, and SEQ ID NO: 2241;
  (iii) 14 lncRNAs of SEQ ID NO: 2150, SEQ ID NO: 1534, SEQ ID NO: 0311, SEQ ID NO: 2952, SEQ ID NO: 2838, SEQ ID NO: 1437, SEQ ID NO: 1297, SEQ ID NO: 1059, SEQ ID NO: 1465, SEQ ID NO: 2826, SEQ ID NO: 0180, SEQ ID NO: 0538, SEQ ID NO: 0258, and SEQ ID NO: 2273;

(iv) 20 lncRNAs of SEQ ID NO: 0190, SEQ ID NO: 0359, SEQ ID NO: 0776, SEQ ID NO: 1421, SEQ ID NO: 1795, SEQ ID NO: 0477, SEQ ID NO: 1511, SEQ ID NO: 0435, SEQ ID NO: 1418, SEQ ID NO: 1025, SEQ ID NO: 0265, SEQ ID NO: 1311, SEQ ID NO: 2540, SEQ ID NO: 2323, SEQ ID NO: 3011, SEQ ID NO: 2447, SEQ ID NO: 2863, SEQ ID NO: 2697, SEQ ID NO: 3128, and SEQ ID NO: 2265;

(v) 11 lncRNAs of SEQ ID NO: 2540, SEQ ID NO: 0545, SEQ ID NO: 1766, SEQ ID NO: 3011, SEQ ID NO: 0968, SEQ ID NO: 2371, SEQ ID NO: 1533, SEQ ID NO: 0749, SEQ ID NO: 0609, SEQ ID NO: 1446, and SEQ ID NO: 2986;

(vi) 8 lncRNAs of SEQ ID NO: 1204, SEQ ID NO: 2454, SEQ ID NO: 0334, SEQ ID NO: 1403, SEQ ID NO: 1089, SEQ ID NO: 2692, SEQ ID NO: 2273, SEQ ID NO: 0502;

(vii) 4 lncRNAs of SEQ ID NO: 0097, SEQ ID NO: 1947, SEQ ID NO: 1051 and SEQ ID NO: 2996; and (viii) lncRNAs in Table 4, Table 5, Table 8, Table 9, Table 12, Table 15, Table 18, Table 19, Table 20, Table 21, Table 22, Table 24, Table 25, Table 28, Table 29, Table 32, Table 33, Table 34, Table 35, Table 36, Table 37, Table 38, Table 39, Table 40, and/or Table 41.

EXAMPLES

Example 1 Identification of lncRNAs of the Invention

The inventors incorporate deep RNA-sequencing of cardiac biopsies starting from total RNA to characterize both coding and non-coding transcriptomes and identify cardiac relevant lncRNA through a multistep analysis procedure. The Inventors use differential expression analysis as well as novel transcript reconstruction and data integration into genome-wide data sets as well as previously characterized predicted human cardiac-specific lncRNA to systematically identify heart-specific lncRNAs. Using the aforementioned techniques, the Inventors can identify 3,238 lncRNAs potentially relevant to cardiac disorders. Indeed, hundreds of known lncRNA are differentially expressed in a control subject compared to a subject suffering from ischemic or dilated cardiomyopathies. The Inventors are able to determine that 1027 novel lncRNAs, including some orthologs predicted in the art, that are differentially expressed and/or cardiac-enriched.

Sample Collection

Cardiac biopsies are obtained from 5 control patients, 11 patients suffering ICM and 10 patients suffering DCM. Biopsies of control hearts are provided from subjects with either head injury (n=2) or subarachnoid haemorrhage (n=3). The protocol is approved by the Local Ethics Committee at Cardinal Stefan Wyszynski Institute of Cardiology (approval number IK-NP-0021-48/846/13 (Apr. 9, 2013). No donors or their relatives completed the National Refusal List. Heart biopsies obtained from the left ventricle are snap-frozen and stored at −80° C. until RNA isolation.

RNA Isolation

Total RNA is extracted from cardiac biopsies using the mirVana isolation kit (Life technologies, Merelbeke, Belgium). Potential contaminating genomic DNA is digested with DNase I (Qiagen, Venlo, The Netherlands). RNA concentration is measured with a Nanodrop spectrophotometer (Nanodrop products, Wilmington, USA) and RNA integrity is verified using a 2100 Bioanalyzer (Agilent technologies, Santa Clara, USA).

Biopsies Sequencing

Sequencing libraries are prepared from 0.5 µg of total RNA using the Illumina TruSeq stranded total RNA library preparation kit combined with the human/mouse/rat RiboZero rRNA removal kit (Illumina Inc. San Diego, USA, C). All steps are performed with the low-throughput protocol and according to the manufacturer's instructions. Briefly, cytoplasmic rRNA are hybridized to biotinylated target-specific oligos and removed using streptavidin coated magnetic beads. rRNA depleted RNA samples are then fragmented by heat digestion with divalent cations (8 minutes, 94° C.) and reverse transcribed into cDNA. To ensure strand specificity, single stranded cDNA is first synthetized using Super-Script II reverse transcriptase (Invitrogen) and random primers in the presence of Actinomycin D, and then converted to double stranded cDNA with the second strand marking mix that incorporates dUTP in place of dTTP. Resulting blunt ended cDNA are purified using AMPure XP magnetic beads. After a 3' end adenylation step, Illumina's adapters ligation is performed. The singled indexed libraries thus obtained are washed twice using AMPure XP beads to remove excess adapters and enriched by PCR (15 cycles). PCR products are purified with a final AMPure XP beads wash and sequencing ready libraries are eluted in 30 µl of resuspension buffer.

For quality control, 1 µl of each library is run on the Agilent Technologies 2100 Bioanalyzer using a DNA 1000 chip according to the manufacturer's recommendations. Absence of adapter dimers is checked and the average library size is determined by a region table. Libraries are quantified by qPCR using the KAPA Library quantification kit for Illumina Platforms (KAPAbiosystems). Samples are run in duplicate and quantified against a standard curve ranging from 20 to 2.10-4 pM. Library size previously determined on the Bioanalyzer is used for size correction of the calculated concentrations.

All libraries are sequenced with the Illumina NextSeq500 (2×75 bp).

Sequencing Analysis for Known Transcripts

All RNA-seq reads of 26 samples are aligned to human reference genome (hg19) using Tophat 2.1.0 (1). Bowtie index of UCSC reference sequences are downloaded from Illumina iGenomes. The transcript assembly is performed using cufflinks 2.2.1 (1) with –G option and the feature-Counts function of Rsubread R package (2). The GTF file is generated by integrating GENCODE comprehensive gene annotation release 19 (3) and human lncRNAs identified by Ounzain et al. (4). Cuffdiff (1) and DESeq2 (5) are respectively used for differential expression analysis. Transcripts with an adjusted p-value<0.05 between controls and failing hearts, or with a p-value<0.05 between ICM and DCM are considered to be differentially expressed.

Pipeline of Novel lncRNA Prediction

De Novo Transcript Assembly

RABT (Reference Annotation Based Transcript) assembly (6) is performed using cufflinks with –g option for 3 control samples, 3 ICM samples and 3 DCM samples. The GTF file is the same as the one used for known transcripts. The cuffcompare (1) program is used to compare the assembled transcripts to the reference annotated GTF file and to generate a new GTF file with all transcripts from 9 samples for further analysis.

Filtering for Novel lncRNAs

Filtering is done on Transfrag class codes generated by cuffcompare, transcript length, number of exons and protein coding potential. Firstly, the transcripts with code 'i', 'j', 'o', 'u', 'x' and '.' are extracted, all of which could potentially include novel lncRNAs. The 'i' category, for example, could contain the lncRNAs entirely within the intron of known genes. Similarly, the '.' category could be long non-coding isoforms of known genes. The 'o' category could include novel lncRNAs having generic exonic overlap with known transcripts. The V category could be long intergenic non-coding RNAs (lincRNAs). The 'x' category could contain novel lncRNAs on the opposite strand of reference genes. The category may be sequences with multiple classifications. The combined GTF file is converted to a BED file using UCSC table browser (7). Following this, only the transcripts with a length of ≥200 nt and with at least 2 exons are kept for the next step. Finally, the BED files of transcripts from the last 2 filtering steps are uploaded to CPAT (Coding-Potential Assessment Tool) (8) to calculate the coding potential score. The transcripts with CPAT scores <0.364 are considered as non-coding. A new GTF file is generated with the final list of selected novel lncRNAs.

Differential Expression of Novel lncRNAs

The cuffdiff (1) is used for all 26 samples with the new GTF file of novel lncRNAs. Transcripts with an adjusted p-value<0.05 are considered to be differentially expressed.

Analysis for Public Dataset

Fastq files of GSE45326 are downloaded from ArrayExpress (9). The dataset includes RNA-seq data of 12 normal human tissues. The paired-end sequencing is performed on ribominus total RNA library. Reads alignment and transcript assembly for known genes are performed as described before. Cufflinks (1) with the GTF file of novel lncRNAs is used to calculate FPKM of novel lncRNAs in each tissue. The transcripts with FPKM≥1 and at least twice higher than the FPKM of any other tissues are considered as cardiac-enriched.

The selection of the lncRNA of the panel is a multistep procedure:

Known transcripts selection.

In a first step, the inventors focused on the identification of known lncRNA that are relevant to cardiac pathophysiology. After data alignment and transcript reconstruction using both Cufflink and features counts using Gencode19, the authors used two distinct tools that use different approaches for differential expression analysis, respectively Cuffdiff and DeSeq2, and only transcripts showing high expression (fragments per kilobase of transcript per million mapped reads (FPKM) FPKM or FPM≥1) in at least half the samples of one group are considered. Differential expression using both tools is analysed in controls vs ICM samples, controls vs DCM samples, as well as ICM vs DCM samples. 80 and 1193 differentially expressed transcripts between any of the groups are identified with Cuffdiff and DeSeq2 analysis respectively. This difference is mainly due to the low number of lncRNA flagged OK by Cuffdiff (ie, neither NOTEST nor HIDATA). As those excluded lncRNA are included in the DeSeq2 analysis, Cuffdiff default settings are not modified. Interestingly, we observed from the DeSeq2 analysis that even if the majority of differentially expressed transcripts in controls vs ICM samples are also differentially expressed in controls vs DCM samples (and vice versa), about one third of them are ICM or DCM specific, illustrating that as the coding transcriptome, the noncoding transcriptome shows features common to a common heart defect (cardiomyopathies) but also specific ones differentiating the physiological bases of this defect (ischemic vs non-ischemic). Moreover, 97 lncRNAs are also differentially expressed between ICM and DCM patients, differentiating the 2 pathologies. Similar observations are made from the Cuffdiff analysis.

The authors also focused on highly expressed non coding transcripts and thus selected 687 lncRNA having a FPKM or FPM≥2 to include in the panel.

In summary, the authors identified 1,835 lncRNA corresponding to 1,501 genes, previously annotated in Gencode19, as relevant for cardiac function.

Predicted Human Orthologs Selection

In order to validate the relevance of the humans orthologs identified by Ounzain et al, the authors realized the same analysis using the GTF file containing the predicted human orthologs as reference for transcripts reconstruction. Surprisingly, the inventors identified few predicted orthologs that are expressed in human tissue: 86 corresponding to 77 genes. Among them, 75 are differentially expressed lncRNA across the control, ICM and DCM groups, 16 highly expressed (FPKM or FPM≥2) lncRNA and 5 of them fitted the 2 criteria. This unexpected low amount of validated predicted human orthologs can in part be explained by the different sequencing approaches used in the 2 studies. Nonetheless, the so identified lncRNAs, shown to be highly tissue and context specific in mice and validated in human cardiac disorders appear to be promising biomarker candidates playing crucial roles in cardiac function regulation.

Cardiac-Enriched Transcripts Selection

As stated in the previous study from Ounzain et al, lncRNA regulating cardiac homeostasis identified in mice are highly context specific but also and importantly, cardiac tissue specific.

This led us to look for non-coding transcripts that are enriched in the cardiac tissue compared to others and thus might play important roles in cardiac functions. By comparing public RNA-seq data from 12 human tissues (heart, brain, bladder, colon, breast, skin, lung, ovary, kidney, prostate, liver, muscle), the inventors identified 470 and 24 lncRNA, from known and Human predicted transcripts respectively, that had at least a 2 fold higher expression rate in cardiac tissue than in any other tissue.

Novel Transcripts Selection

The growing interest on lncRNA together with the development of next generation sequencing techniques over the past years has led to a better knowledge of these non-coding transcripts. Nonetheless, non-coding transcripts account for the majority of the human transcriptome and have so far not been completely characterized. The authors thus performed very deep sequencing to allow for discovery of novel transcripts. After de novo transcript reconstruction and transcript selection as detailed in the material and methods, the inventors can identify over 13,000 new transcripts with no coding potential. Among them, they can identify 696 lncRNA differentially expressed between the 3 groups (FDR<0.05) and 810 lncRNA enriched in cardiac tissue. The transcripts having class codes 'o', 'j' or 'i' and highly positively correlated with overlapped known genes are eliminated. ('i' category, for example, could contain the lncRNAs entirely within the intron of known genes, the 'j' category could be long non-coding isoforms of known genes and the 'o' category could include novel lncRNAs having generic exonic overlap with known transcripts). The transcripts with class codes 'j' or 'o' and overlapping with exons of known protein-coding genes on the same strand are discarded. This resulted in a total number of novel lncRNAs of 755 relevant to cardiac physiology.

In summary, the inventors identified a highly relevant panel of 3,092 cardiac-related lncRNAs. This panel encompasses 2,317 known transcripts here shown to be relevant to cardiac physiology, as well as 755 lncRNA, here described for the first time and relevant to cardiac tissue.

Example 2

LncRNA Detection in Plasma Samples and PCR Validation in Biopsies

Sample Selection: Mitocare Aidbank/

Like miRNA, lncRNA can be released from the original tissue into the body circulation. Thus such markers may be detected in body fluids like whole blood or plasma which facilitates their use in clinics. The expression of four lncRNA previously identified is verified in plasma samples from patients who suffered AMI versus control patients.

Plasma samples from 3 control subjects and 3 subjects who suffered AMI are used. RNA extraction is performed using Norgen Serum/plasma extraction kit according to the manufacturer's instructions. Isolated RNAs are then subjected to reverse transcription using the high capacity cDNA synthesis kit with the following thermal conditions: 25° C. for 10 min, 37° C. for 2 hours, 85° C. for 5 min Preamplification reactions are prepared using Applied Biosystems preamplication master mix with 0.1× (100 nM) of each of the 4 primers pairs corresponding to the lncRNAs of interest (sequences listed below). 16 preamplification cycles are performed as recommended by the furnisher (50° C. 2 minutes, 96° C. 10 minutes, 40 cycles at 95° C. for 15 seconds and 60° C. for 1 minute). Preamplified products are then diluted 1/20 in TE buffer and quantified by qPCR using the Biorad Ssoadvanced SYBR green kit. Briefly, 15 µl reactions containing 6 ul of each diluted sample are amplified in a 1× ready to use reaction mix containing 500 µl of the diluted sample, 1× biorad reaction mix and 500 nM sense and reverse primers are amplified on a ABIHT7900 with the following conditions: 30 sec 95° C., 40 cycles of 15 sec at 95° C. denaturation and 30 sec at 60° C. annealing and extension). Relative expression level is determined against a standard curve realized on a 5 log scale.

TABLE 2

| | |
|---|---|
| Lnc21524Se (SEQ ID NO: 3239) | TTGAATCCTGGCTTTGCTCT |
| Lnc21524As (SEQ ID NO: 3240) | GGAAAGGCAATTGAGTGAGG |
| Lnc23749Se (SEQ ID NO: 3241) | TTGGTCTTTCACCCTTCCTG |
| Lnc23749As (SEQ ID NO: 3242) | GAAAACGTCCTCCCTCCTTC |
| Lnc19889Se (SEQ ID NO: 3243) | ACACGGGAAGCTCTTTGAGA |
| Lnc19889As (SEQ ID NO: 3244) | TCAAGAGGGAAGGATGGATG |
| LncAnx5aSe (SEQ ID NO: 3245) | GAATTTCTGGGGACCTTTCC |
| LncAnx5aAs (SEQ ID NO: 3246) | GCAAAGGGAGAGAAAGCAGA |

Figure 4:
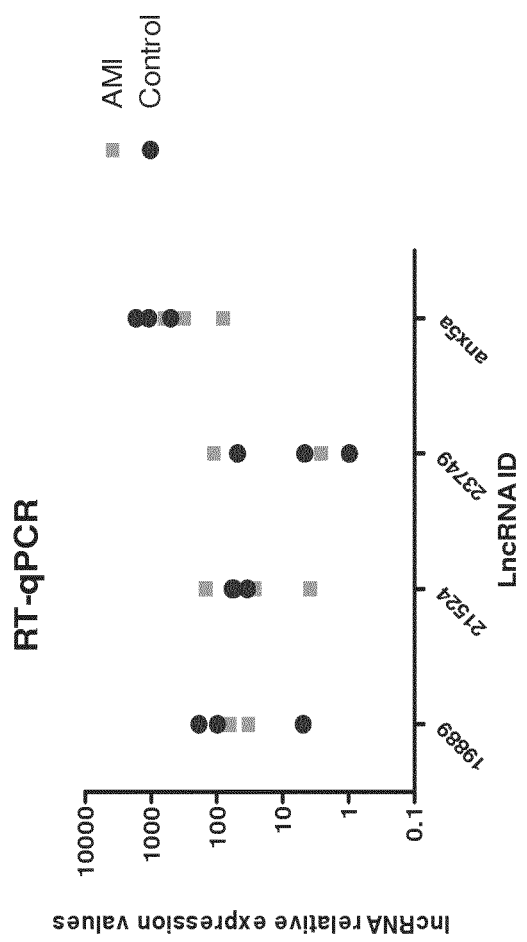
FIG. 4 shows the expression of 4 lncRNA in human plasma samples as analyzed by qRT-PCR after preamplification: AMI indicated by a square and Control indicated by a circle.

In FIG. 4, the authors showed that lncRNA are indeed detectable in plasma samples. Moreover expression profile compared to NGS data (lnc21524 identified with NGS need more precision on DE).

Example 3: lncRNA Detection in Serum Samples Using a Total RNA-Seq Protocol

Material and Methods:

Quantification of lncRNAs in body fluids like whole blood, serum or plasma is a non-invasive way to develop a diagnostic test to use in clinics. The expression of circulating lncRNA released by the tissues was studied in serum samples from patients with AMI and control subjects. Serum samples collected at discharge of patient between D3 and D5 from 30 patients with AMI from the MitoCare cohort were used for lncRNA profiling. Mitocare is a multicenter, randomized, double-blind, placebo controlled study. The study population includes AMI patients undergoing PCI (Percutaneous Coronary Intervention), older than 18 years. The primary endpoint is the level of left ventricular ejection fraction (LVEF) less than 40% at 1 month. Patients demographics are presented in Table 3. Control serum samples were selected from subjects of ADDIA Chronobiological study.

TABLE 3

Demographic data of Mitocare samples:

| | Group 1 | Group 2 | Group 3 |
|---|---|---|---|
| EF | <40 | 41-50 | >50 |
| Nb | 10 | 10 | 10 |
| Age | 64.0 | 64.2 | 60.9 |
| Male | 80% | 80% | 70% |
| BMI | 27.4 | 28.3 | 27.6 |
| Systolic Blood Pressure | 103.5 | 116.9 | 113.6 |
| Diastolic Blood Pressure | 67.4 | 70.2 | 66.5 |
| Heart Rate | 83.3 | 75.9 | 69.3 |

Serum Samples Sequencing

RNA is extracted from 1.5 ml of serum, using Norgen Serum extraction and RNA Clean-Up and Concentration Micro-Elute Kits according to the manufacturer's instructions. Sequencing libraries are prepared from the total amount of extracted RNA, using the Illumina TruSeq stranded total RNA library preparation kit combined with the human/mouse/rat RiboZero rRNA removal kit (Illumina Inc. San Diego, USA, C). All steps are performed with the low-throughput protocol and according to the manufacturer's instructions, with no fragmentation step. Briefly, cytoplasmic rRNA are hybridized to biotinylated target-specific oligos and removed using streptavidin coated magnetic beads. rRNA depleted RNA samples are then reverse transcribed into cDNA. To ensure strand specificity, single stranded cDNA is first synthetized using Super-Script II reverse transcriptase (Invitrogen) and random primers in the presence of Actinomycin D, and then converted to double stranded cDNA with the second strand marking mix that incorporates dUTP in place of dTTP. Resulting blunt ended cDNA are purified using AMPure XP magnetic beads. After a 3' end adenylation step, Illumina's adapters ligation is performed. So obtained singled indexed libraries are washed twice using AMPure XP beads to remove excess adapters and enriched by PCR (15 cycles). PCR products are purified with a final AMPure XP beads wash and sequencing ready libraries are eluted in 30 µl of resuspension buffer.

For quality control, 1 µl of each library is run on the Agilent Technologies 2100 Bioanalyzer using a DNA 1000 chip according to the manufacturer's recommendations. Absence of adapter dimers is checked and the average library size is determined by a region table. Libraries are quantified on Qubit 2.0 using Qubit dsDNA High Sensitivity assay kit (Invitrogen). Library size previously determined on the Bioanalyzer is used to calculate molar concentrations from mass concentrations.

All libraries are sequenced with the Illumina NextSeq500 (2×75 bp).

Sequencing Analysis for the 3238 lncRNAs

RNA-seq data analysis is performed using Partek Flow (Partek Inc., St Louis, Mo., USA build 6). The pre-alignment QA/QC module of Partek Flow is used to visualize the read quality of the FASTQ files. All reads are examined. The raw FASTQ files are trimmed at the 3' end in function of their quality score (Phred score). The parameters used are an end minimum quality level of 30 and a minimum trimmed read length of 50. Unaligned reads are mapped using the *Homo* sapiens hg19 genome and using as guide a GTF file with the patented lncRNA annotation. This mapping is done using the software STAR version 2.5.3. The default parameters are used. The post-alignment QC module of Partek Flow is used to visualize the average base quality score per position as well as the mapping quality per alignment. The mapped reads are quantified using the GTF file with the patented lncRNA annotation for quantification using the Partek Expectation/Maximization (E/M) algorithm. The default parameters are used. The transcript counts are normalized by CPM (counts per million). Only transcripts showing high expression (CPM≥10) in at least half the samples of one group are considered.

Statistical Analysis and Predictive Modelling

For the statistical analysis, samples are grouped into 2 groups based on the left ventricular ejection fraction (LVEF) measured by echocardiography at 1-month after the PCI. To identify differentially expressed lncRNA, a statistical analysis is performed using a non-parametric Wilcoxon-Mann-Whitney test and a parametric T-test. A lncRNA with a p-value≤0.05 is considered as differentially expressed.

In order to build classification models for the 2 classifications, the Classification for MicroArrays (CMA) package of R (Slawski et al, 2008) with a leave-one-out cross-validation is used. The algorithms used for this predictive modelling are (a) random forest, (b) linear discriminant analysis and (c) naïve Bayes.

Results:

Comparison Between Low LVEF (LVEF≤40) and High LVEF (LVEF>40)

First, samples were grouped into 2 groups by a dichotomized variable: 1-month LVEF<40% considered as LV dysfunction (Ventricular remodeling) and 1-month LVEF>40% considered as preserved LV function. The volcano plot showed the differential expression of lncRNA. 192 lncRNAs are differentially expressed and among these, 20 lncRNAs are differentially expressed and have a fold change>2 or <0.5 between the low LVEF (LVEF≤40) and the high LVEF (LVEF>40) groups. The p-value and the fold-change of these lncRNA are listed in the Table 4. 316 lncRNAs which have a P<0.05 and/or an individual AUC>0.7 or <0.3 are listed in Table 5.

TABLE 4

List of 20 lncRNAs which are differentially expressed between the low LVEF group (LVEF ≤ 40) and the high LVEF group (LVEF > 40)

| lncRNA | p-value | Fold change |
|---|---|---|
| SEQ ID NO: 0930 | 0.03736 | 2.042 |
| SEQ ID NO: 0821 | 0.03299 | 0.491 |
| SEQ ID NO: 1196 | 0.00653 | 2.648 |
| SEQ ID NO: 0664 | 0.00660 | 0.441 |
| SEQ ID NO: 2642 | 0.04102 | 2.623 |
| SEQ ID NO: 1910 | 0.04224 | 2.669 |
| SEQ ID NO: 1239 | 0.01161 | 0.475 |
| SEQ ID NO: 0243 | 0.04133 | 0.490 |
| SEQ ID NO: 2368 | 0.00240 | 0.443 |
| SEQ ID NO: 0283 | 0.01599 | 2.363 |
| SEQ ID NO: 1837 | 0.04199 | 0.416 |
| SEQ ID NO: 0527 | 0.01436 | 0.487 |
| SEQ ID NO: 1167 | 0.01803 | 0.296 |
| SEQ ID NO: 0153 | 0.04675 | 2.333 |
| SEQ ID NO: 1757 | 0.04483 | 2.224 |
| SEQ ID NO: 1719 | 0.02190 | 0.367 |
| SEQ ID NO: 1650 | 0.00217 | 0.487 |
| SEQ ID NO: 0051 | 0.01192 | 52.864 |
| SEQ ID NO: 1410 | 0.00818 | 2.953 |
| SEQ ID NO: 2699 | 0.02230 | 2.072 |

TABLE 5

List of 316 lncRNAs which are differentially expressed and/or have an AUC >0.7 or <0.3 between the low LVEF group (LVEF ≤ 40) and the high LVEF group (LVEF > 40)

| LncRNA (SEQ ID NO:) | p-value | AUC |
|---|---|---|
| 0005 | 0.033 | 0.755 |
| 0033 | 0.131 | 0.715 |
| 0037 | 0.061 | 0.73 |
| 0042 | 0.119 | 0.715 |
| 0043 | 0.068 | 0.175 |
| 0051 | 0.012 | 0.225 |
| 0069 | 0.168 | 0.255 |
| 0075 | 0.028 | 0.745 |
| 0119 | 0.021 | 0.33 |
| 0120 | 0.046 | 0.735 |
| 0136 | 0.026 | 0.71 |
| 0141 | 0.05 | 0.28 |
| 0153 | 0.047 | 0.328 |
| 0163 | 0.083 | 0.285 |
| 0169 | 0.042 | 0.73 |
| 0172 | 0.045 | 0.74 |
| 0173 | 0.046 | 0.76 |
| 0189 | 0.024 | 0.755 |
| 0190 | 0.043 | 0.73 |
| 0199 | 0.004 | 0.83 |
| 0208 | 0.027 | 0.283 |
| 0216 | 0.087 | 0.735 |
| 0226 | 0.083 | 0.72 |
| 0243 | 0.041 | 0.73 |
| 0244 | 0.01 | 0.24 |
| 0283 | 0.016 | 0.27 |
| 0290 | 0.079 | 0.715 |
| 0312 | 0.065 | 0.25 |
| 0321 | 0.022 | 0.815 |
| 0334 | 0.017 | 0.785 |
| 0339 | 0.042 | 0.71 |
| 0363 | 0.001 | 0.87 |
| 0366 | 0.216 | 0.3 |
| 0383 | 0.052 | 0.7 |
| 0386 | 0.113 | 0.715 |
| 0388 | 0.116 | 0.71 |
| 0392 | 0.029 | 0.74 |
| 0398 | 0.027 | 0.795 |
| 0405 | 0.051 | 0.73 |
| 0420 | 0.06 | 0.72 |
| 0454 | 0.06 | 0.295 |
| 0493 | 0.05 | 0.715 |
| 0495 | 0.072 | 0.755 |
| 0502 | 0.065 | 0.75 |
| 0538 | 0.083 | 0.715 |
| 0544 | 0.002 | 0.825 |
| 0552 | 0.039 | 0.775 |
| 0560 | 0.063 | 0.725 |
| 0565 | 0.064 | 0.7 |
| 0586 | 0.032 | 0.775 |
| 0615 | 0.008 | 0.825 |
| 0638 | 0.017 | 0.77 |
| 0643 | 0.072 | 0.725 |
| 0664 | 0.007 | 0.815 |
| 0677 | 0.073 | 0.74 |
| 0685 | 0.014 | 0.79 |
| 0688 | 0.079 | 0.72 |
| 0702 | 0.035 | 0.77 |

TABLE 5-continued

List of 316 lncRNAs which are differentially expressed and/or have an AUC >0.7 or <0.3 between the low LVEF group (LVEF ≤ 40) and the high LVEF group (LVEF > 40)

| LncRNA (SEQ ID NO:) | p-value | AUC |
|---|---|---|
| 0745 | 0.029 | 0.725 |
| 0748 | 0.052 | 0.71 |
| 0753 | 0.063 | 0.7 |
| 0781 | 0.015 | 0.76 |
| 0796 | 0.065 | 0.7 |
| 0821 | 0.033 | 0.738 |
| 0858 | 0.129 | 0.7 |
| 0861 | 0.082 | 0.715 |
| 0866 | 0.036 | 0.735 |
| 0904 | 0.042 | 0.73 |
| 0910 | 0.054 | 0.72 |
| 0915 | 0.009 | 0.81 |
| 0917 | 0.025 | 0.765 |
| 0925 | 0.037 | 0.72 |
| 0930 | 0.037 | 0.3 |
| 0935 | 0.039 | 0.72 |
| 0944 | 0.055 | 0.725 |
| 0948 | 0.073 | 0.28 |
| 0959 | 0.029 | 0.745 |
| 0994 | 0.12 | 0.715 |
| 1001 | 0.11 | 0.713 |
| 1004 | 0.041 | 0.715 |
| 1014 | 0.037 | 0.74 |
| 1036 | 0.038 | 0.25 |
| 1040 | 0.134 | 0.72 |
| 1042 | 0.046 | 0.31 |
| 1046 | 0.006 | 0.785 |
| 1075 | 0.069 | 0.7 |
| 1081 | 0.055 | 0.73 |
| 1089 | 0.045 | 0.765 |
| 1094 | 0.013 | 0.78 |
| 1095 | 0.089 | 0.74 |
| 1113 | 0.037 | 0.725 |
| 1114 | 0.063 | 0.71 |
| 1127 | 0.061 | 0.715 |
| 1171 | 0.106 | 0.745 |
| 1179 | 0.049 | 0.28 |
| 1182 | 0.032 | 0.73 |
| 1198 | 0.016 | 0.765 |
| 1204 | 0 | 0.88 |
| 1205 | 0.001 | 0.8 |
| 1214 | 0.045 | 0.71 |
| 1231 | 0.037 | 0.3 |
| 1240 | 0.044 | 0.74 |
| 1271 | 0.109 | 0.715 |
| 1276 | 0.053 | 0.725 |
| 1281 | 0.016 | 0.22 |
| 1286 | 0.409 | 0.71 |
| 1301 | 0.087 | 0.71 |
| 1319 | 0.048 | 0.32 |
| 1329 | 0.006 | 0.245 |
| 1340 | 0.084 | 0.283 |
| 1347 | 0.065 | 0.705 |
| 1348 | 0.013 | 0.275 |
| 1356 | 0.099 | 0.705 |
| 1373 | 0.024 | 0.215 |
| 1377 | 0.121 | 0.7 |
| 1385 | 0.117 | 0.71 |
| 1391 | 0.133 | 0.71 |
| 1398 | 0.004 | 0.195 |
| 1403 | 0.018 | 0.775 |
| 1404 | 0.109 | 0.705 |
| 1406 | 0.083 | 0.74 |
| 1410 | 0.008 | 0.235 |
| 1412 | 0.042 | 0.775 |
| 1420 | 0.042 | 0.75 |
| 1428 | 0.006 | 0.225 |
| 1442 | 0.026 | 0.715 |
| 1444 | 0.057 | 0.29 |
| 1449 | 0.089 | 0.7 |
| 1454 | 0.098 | 0.708 |
| 1462 | 0.071 | 0.728 |
| 1468 | 0.002 | 0.81 |
| 1483 | 0.041 | 0.27 |
| 1518 | 0.154 | 0.71 |
| 1528 | 0.018 | 0.735 |
| 1556 | 0.102 | 0.72 |
| 1564 | 0.018 | 0.765 |
| 1576 | 0.051 | 0.725 |
| 1583 | 0.083 | 0.715 |
| 1595 | 0.152 | 0.715 |
| 1601 | 0.007 | 0.24 |
| 1618 | 0.056 | 0.275 |
| 1626 | 0.004 | 0.785 |
| 1632 | 0.048 | 0.305 |
| 1638 | 0.091 | 0.275 |
| 1656 | 0.083 | 0.725 |
| 1667 | 0.022 | 0.735 |
| 1674 | 0.006 | 0.8 |
| 1683 | 0.024 | 0.745 |
| 1692 | 0.084 | 0.745 |
| 1693 | 0.05 | 0.7 |
| 1705 | 0.12 | 0.295 |
| 1707 | 0.016 | 0.77 |
| 1712 | 0.063 | 0.71 |
| 1715 | 0.01 | 0.665 |
| 1719 | 0.022 | 0.77 |
| 1726 | 0.006 | 0.23 |
| 1732 | 0.002 | 0.855 |
| 1733 | 0.046 | 0.74 |
| 1737 | 0.037 | 0.315 |
| 1746 | 0.137 | 0.705 |
| 1757 | 0.045 | 0.338 |
| 1793 | 0.13 | 0.71 |
| 1804 | 0.056 | 0.75 |
| 1809 | 0.05 | 0.305 |
| 1818 | 0.022 | 0.74 |
| 1819 | 0.031 | 0.8 |
| 1820 | 0.154 | 0.255 |
| 1837 | 0.042 | 0.748 |
| 1842 | 0.035 | 0.735 |
| 1853 | 0.194 | 0.705 |
| 1869 | 0.051 | 0.755 |
| 1910 | 0.042 | 0.37 |
| 1926 | 0.061 | 0.755 |
| 1938 | 0.058 | 0.71 |
| 1942 | 0.048 | 0.72 |
| 1947 | 0.091 | 0.733 |
| 1950 | 0.156 | 0.71 |
| 1954 | 0.174 | 0.29 |
| 1979 | 0.04 | 0.72 |
| 1983 | 0.002 | 0.865 |
| 2026 | 0.031 | 0.71 |
| 2049 | 0.012 | 0.78 |
| 2053 | 0.121 | 0.71 |
| 2061 | 0.068 | 0.29 |
| 2074 | 0.004 | 0.215 |
| 2100 | 0.007 | 0.78 |
| 2114 | 0.062 | 0.725 |
| 2121 | 0.058 | 0.725 |
| 2126 | 0.032 | 0.25 |
| 2157 | 0.049 | 0.695 |
| 2162 | 0.051 | 0.705 |
| 2190 | 0.109 | 0.705 |
| 2209 | 0.074 | 0.81 |
| 2216 | 0.077 | 0.71 |
| 2240 | 0.069 | 0.27 |
| 2253 | 0.006 | 0.19 |
| 2260 | 0.063 | 0.285 |
| 2273 | 0.064 | 0.72 |
| 2274 | 0.043 | 0.27 |
| 2282 | 0.023 | 0.235 |
| 2286 | 0.06 | 0.295 |
| 2287 | 0.048 | 0.27 |
| 2288 | 0.007 | 0.2 |
| 2294 | 0.086 | 0.705 |
| 2299 | 0.015 | 0.765 |
| 2314 | 0.019 | 0.735 |

TABLE 5-continued

List of 316 lncRNAs which are differentially expressed and/or have an AUC >0.7 or <0.3 between the low LVEF group (LVEF ≤ 40) and the high LVEF group (LVEF > 40)

| LncRNA (SEQ ID NO:) | p-value | AUC |
|---|---|---|
| 2320 | 0.005 | 0.83 |
| 2344 | 0.024 | 0.72 |
| 2349 | 0.1 | 0.275 |
| 2352 | 0.033 | 0.32 |
| 2353 | 0.075 | 0.705 |
| 2360 | 0.045 | 0.295 |
| 2368 | 0.002 | 0.85 |
| 2373 | 0 | 0.85 |
| 2374 | 0.016 | 0.245 |
| 2377 | 0.036 | 0.73 |
| 2382 | 0.012 | 0.835 |
| 2385 | 0.05 | 0.72 |
| 2402 | 0.003 | 0.82 |
| 2405 | 0.102 | 0.7 |
| 2407 | 0.1 | 0.275 |
| 2411 | 0.047 | 0.7 |
| 2454 | 0.015 | 0.755 |
| 2457 | 0.027 | 0.74 |
| 2461 | 0.031 | 0.245 |
| 2466 | 0.138 | 0.71 |
| 2470 | 0.001 | 0.15 |
| 2472 | 0.032 | 0.255 |
| 2478 | 0.02 | 0.23 |
| 2484 | 0.038 | 0.28 |
| 2485 | 0.026 | 0.375 |
| 2501 | 0.008 | 0.805 |
| 2502 | 0.049 | 0.745 |
| 2518 | 0.091 | 0.29 |
| 2521 | 0.015 | 0.3 |
| 2523 | 0.019 | 0.76 |
| 2540 | 0.019 | 0.745 |
| 2544 | 0.022 | 0.255 |
| 2560 | 0.075 | 0.705 |
| 2567 | 0.026 | 0.745 |
| 2593 | 0.057 | 0.29 |
| 2605 | 0.044 | 0.32 |
| 2618 | 0.032 | 0.215 |
| 2622 | 0.118 | 0.29 |
| 2631 | 0.027 | 0.27 |
| 2644 | 0.054 | 0.285 |
| 2657 | 0.033 | 0.65 |
| 2658 | 0.069 | 0.27 |
| 2677 | 0.037 | 0.7 |
| 2684 | 0.005 | 0.185 |
| 2692 | 0.062 | 0.28 |
| 2695 | 0.026 | 0.24 |
| 2696 | 0.07 | 0.265 |
| 2697 | 0.045 | 0.725 |
| 2698 | 0.052 | 0.705 |
| 2699 | 0.022 | 0.325 |
| 2702 | 0.041 | 0.34 |
| 2703 | 0.005 | 0.805 |
| 2715 | 0.032 | 0.25 |
| 2720 | 0.054 | 0.7 |
| 2726 | 0.04 | 0.735 |
| 2750 | 0.047 | 0.735 |
| 2752 | 0.025 | 0.695 |
| 2753 | 0.06 | 0.735 |
| 2785 | 0.039 | 0.275 |
| 2794 | 0.035 | 0.32 |
| 2800 | 0.18 | 0.705 |
| 2825 | 0.11 | 0.7 |
| 2830 | 0.018 | 0.72 |
| 2833 | 0.158 | 0.295 |
| 2853 | 0.003 | 0.785 |
| 2875 | 0.047 | 0.28 |
| 2882 | 0.037 | 0.24 |
| 2896 | 0.02 | 0.27 |
| 2912 | 0.119 | 0.7 |
| 2921 | 0.06 | 0.295 |
| 2922 | 0.015 | 0.25 |
| 2928 | 0.016 | 0.775 |
| 2930 | 0.046 | 0.295 |
| 2960 | 0.057 | 0.28 |
| 2971 | 0.024 | 0.755 |
| 2973 | 0.039 | 0.28 |
| 2974 | 0.067 | 0.7 |
| 2982 | 0.007 | 0.22 |
| 2998 | 0.022 | 0.765 |
| 3002 | 0.04 | 0.69 |
| 3006 | 0.023 | 0.77 |
| 3007 | 0.041 | 0.26 |
| 3013 | 0.05 | 0.725 |
| 3040 | 0.066 | 0.705 |
| 3048 | 0.017 | 0.31 |
| 3066 | 0.009 | 0.805 |
| 3070 | 0.052 | 0.3 |
| 3080 | 0.045 | 0.25 |
| 3085 | 0.034 | 0.725 |
| 3112 | 0.029 | 0.265 |
| 3113 | 0.024 | 0.28 |
| 3118 | 0.085 | 0.265 |
| 3128 | 0.034 | 0.295 |
| 3129 | 0.005 | 0.19 |
| 3133 | 0.019 | 0.765 |
| 3141 | 0.126 | 0.74 |
| 3142 | 0.107 | 0.295 |
| 3143 | 0.025 | 0.305 |
| 3153 | 0.005 | 0.795 |
| 3156 | 0.051 | 0.71 |
| 3170 | 0.044 | 0.295 |
| 3180 | 0.039 | 0.725 |
| 3184 | 0.024 | 0.28 |
| 3187 | 0.024 | 0.33 |
| 3200 | 0.049 | 0.26 |
| 3203 | 0.002 | 0.19 |
| 3204 | 0.017 | 0.75 |
| 3210 | 0.044 | 0.665 |
| 3221 | 0.002 | 0.135 |
| 3230 | 0.036 | 0.3 |

For this classification, the variable selection was performed by using a Random Forest model. A combination of 15 pre-selected lncRNAs through a Random Forest Classifier (Table 6) is the best predictive model obtained here. The lncRNAs were selected using a random forest algorithm. This model has an area under the receiver-operating characteristic curve (AUC) of 0.988, an accuracy of 0.9, a sensitivity of 0.8, a specificity of 0.95, a Positive Predictive Value (PPV) of 0.889 and Negative Predictive Value (PNV) of 0.905. The confusion matrix is presented in Table 7.

TABLE 6

List of 15 pre-selected lncRNAs through a Random Forest Classifier for the classification low LVEF (LVEF ≤ 40) and high LVEF (LVEF > 40)

| lncRNA | Rank in the model |
|---|---|
| SEQ ID NO: 1204 | 1 |
| SEQ ID NO: 1736 | 2 |
| SEQ ID NO: 0544 | 3 |
| SEQ ID NO: 0915 | 4 |
| SEQ ID NO: 2368 | 5 |
| SEQ ID NO: 1595 | 6 |
| SEQ ID NO: 2382 | 7 |
| SEQ ID NO: 0859 | 8 |
| SEQ ID NO: 3112 | 9 |
| SEQ ID NO: 1869 | 10 |
| SEQ ID NO: 1406 | 11 |
| SEQ ID NO: 0043 | 12 |
| SEQ ID NO: 0363 | 13 |

TABLE 6-continued

List of 15 pre-selected lncRNAs through a Random Forest Classifier for the classification low LVEF (LVEF ≤ 40) and high LVEF (LVEF > 40)

| lncRNA | Rank in the model |
|---|---|
| SEQ ID NO: 0069 | 14 |
| SEQ ID NO: 1947 | 15 |

TABLE 7

Confusion matrix of the best model for this classification

| | Low LVEF predicted | High LVEF predicted |
|---|---|---|
| Low LVEF real | 8 | 2 |
| High LVEF real | 1 | 19 |

Comparison between low LVEF (LVEF≤45) and high LVEF (LVEF>45) In this analysis, samples were grouped into 2 groups using the threshold of 45% LVEF: low LVEF (LVEF≤45) and high LVEF (LVEF>45). The volcano plot showed the differential expression of lncRNA. 147 lncRNAs are differentially expressed and among them 15 lncRNA are differentially expressed and have a fold change>2 or <0.5 between the low LVEF (LVEF≤45) and the high LVEF (LVEF>45) groups. The p-value and the fold-change of these lncRNA are listed in the Table 8. 206 lncRNAs which have a P<0.05 and/or an individual AUC>0.7 or <0.3 are listed in Table 9.

TABLE 8

List of 15 lncRNAs which are differentially expressed and have a fold change >2 or <0.5 between the low LVEF group (LVEF ≤ 45) and the high LVEF group (LVEF > 45)

| lncRNA | p-value | fold change |
|---|---|---|
| SEQ ID NO: 2114 | 0.03396 | 0.471 |
| SEQ ID NO: 2512 | 0.04168 | 0.498 |
| SEQ ID NO: 0372 | 0.02201 | 0.427 |
| SEQ ID NO: 0821 | 0.03922 | 0.499 |
| SEQ ID NO: 0664 | 0.00001 | 0.253 |
| SEQ ID NO: 1239 | 0.02909 | 0.499 |
| SEQ ID NO: 2709 | 0.04561 | 0.433 |
| SEQ ID NO: 1385 | 0.03278 | 0.490 |
| SEQ ID NO: 1167 | 0.01103 | 0.222 |
| SEQ ID NO: 1719 | 0.04844 | 0.434 |
| SEQ ID NO: 0917 | 0.00885 | 0.499 |
| SEQ ID NO: 2295 | 0.02772 | 3.217 |
| SEQ ID NO: 1692 | 0.00763 | 0.453 |
| SEQ ID NO: 1707 | 0.00490 | 0.463 |
| SEQ ID NO: 2477 | 0.02006 | 2.142 |

TABLE 9

List of 206 lncRNAs which are differentially expressed and/or have an AUC >0.7 or <0.3 between the low LVEF group (LVEF ≤ 45) and the high LVEF group (LVEF > 45)

| LncRNA (SEQ ID NO:) | p-value | AUC |
|---|---|---|
| 0005 | 0.029 | 0.72 |
| 0022 | 0.046 | 0.62 |
| 0023 | 0.012 | 0.73 |
| 0024 | 0.010 | 0.25 |
| 0037 | 0.056 | 0.72 |
| 0043 | 0.074 | 0.23 |
| 0069 | 0.054 | 0.26 |
| 0076 | 0.051 | 0.73 |
| 0139 | 0.016 | 0.75 |
| 0141 | 0.039 | 0.29 |
| 0147 | 0.021 | 0.72 |
| 0173 | 0.020 | 0.74 |
| 0190 | 0.016 | 0.75 |
| 0213 | 0.123 | 0.72 |
| 0216 | 0.095 | 0.71 |
| 0226 | 0.060 | 0.71 |
| 0227 | 0.054 | 0.72 |
| 0276 | 0.052 | 0.29 |
| 0321 | 0.059 | 0.71 |
| 0334 | 0.023 | 0.77 |
| 0336 | 0.032 | 0.75 |
| 0348 | 0.158 | 0.70 |
| 0357 | 0.025 | 0.72 |
| 0372 | 0.022 | 0.73 |
| 0400 | 0.015 | 0.75 |
| 0440 | 0.022 | 0.75 |
| 0472 | 0.033 | 0.74 |
| 0493 | 0.042 | 0.73 |
| 0502 | 0.065 | 0.71 |
| 0544 | 0.019 | 0.75 |
| 0586 | 0.025 | 0.73 |
| 0615 | 0.066 | 0.70 |
| 0664 | 0.000 | 0.95 |
| 0670 | 0.032 | 0.74 |
| 0688 | 0.040 | 0.72 |
| 0724 | 0.019 | 0.72 |
| 0758 | 0.043 | 0.75 |
| 0778 | 0.524 | 0.73 |
| 0781 | 0.031 | 0.71 |
| 0790 | 0.038 | 0.72 |
| 0821 | 0.039 | 0.71 |
| 0838 | 0.027 | 0.73 |
| 0845 | 0.068 | 0.70 |
| 0867 | 0.039 | 0.72 |
| 0885 | 0.035 | 0.30 |
| 0886 | 0.041 | 0.71 |
| 0891 | 0.059 | 0.30 |
| 0892 | 0.055 | 0.28 |
| 0914 | 0.037 | 0.23 |
| 0915 | 0.018 | 0.76 |
| 0917 | 0.009 | 0.78 |
| 0935 | 0.030 | 0.69 |
| 0983 | 0.055 | 0.28 |
| 1066 | 0.019 | 0.75 |
| 1089 | 0.012 | 0.76 |
| 1097 | 0.065 | 0.28 |
| 1103 | 0.073 | 0.29 |
| 1109 | 0.041 | 0.70 |
| 1162 | 0.030 | 0.72 |
| 1188 | 0.047 | 0.68 |
| 1191 | 0.039 | 0.73 |
| 1204 | 0.062 | 0.72 |
| 1207 | 0.006 | 0.76 |
| 1231 | 0.018 | 0.25 |
| 1237 | 0.104 | 0.29 |
| 1251 | 0.011 | 0.76 |
| 1281 | 0.031 | 0.24 |
| 1302 | 0.033 | 0.27 |
| 1315 | 0.051 | 0.71 |
| 1321 | 0.069 | 0.72 |
| 1329 | 0.032 | 0.26 |
| 1337 | 0.057 | 0.72 |
| 1377 | 0.012 | 0.76 |
| 1385 | 0.033 | 0.75 |
| 1402 | 0.030 | 0.73 |
| 1403 | 0.034 | 0.76 |
| 1404 | 0.031 | 0.72 |
| 1406 | 0.011 | 0.77 |
| 1426 | 0.040 | 0.75 |
| 1428 | 0.005 | 0.22 |
| 1446 | 0.083 | 0.74 |

TABLE 9-continued

List of 206 lncRNAs which are differentially expressed and/or have an AUC >0.7 or <0.3 between the low LVEF group (LVEF ≤ 45) and the high LVEF group (LVEF > 45)

| LncRNA (SEQ ID NO:) | p-value | AUC |
|---|---|---|
| 1454 | 0.063 | 0.70 |
| 1468 | 0.024 | 0.76 |
| 1483 | 0.032 | 0.27 |
| 1489 | 0.141 | 0.26 |
| 1499 | 0.078 | 0.30 |
| 1564 | 0.011 | 0.73 |
| 1576 | 0.096 | 0.70 |
| 1601 | 0.078 | 0.29 |
| 1667 | 0.063 | 0.71 |
| 1674 | 0.055 | 0.73 |
| 1692 | 0.008 | 0.82 |
| 1707 | 0.005 | 0.78 |
| 1719 | 0.048 | 0.71 |
| 1728 | 0.042 | 0.32 |
| 1737 | 0.008 | 0.27 |
| 1748 | 0.111 | 0.72 |
| 1767 | 0.036 | 0.29 |
| 1793 | 0.067 | 0.73 |
| 1804 | 0.048 | 0.69 |
| 1819 | 0.035 | 0.74 |
| 1820 | 0.048 | 0.26 |
| 1821 | 0.055 | 0.71 |
| 1858 | 0.054 | 0.27 |
| 1869 | 0.003 | 0.81 |
| 1873 | 0.071 | 0.71 |
| 1923 | 0.017 | 0.72 |
| 1983 | 0.002 | 0.84 |
| 2049 | 0.029 | 0.74 |
| 2074 | 0.022 | 0.24 |
| 2100 | 0.041 | 0.69 |
| 2114 | 0.034 | 0.68 |
| 2121 | 0.035 | 0.76 |
| 2126 | 0.031 | 0.27 |
| 2127 | 0.220 | 0.73 |
| 2170 | 0.013 | 0.19 |
| 2209 | 0.124 | 0.71 |
| 2216 | 0.033 | 0.72 |
| 2234 | 0.032 | 0.26 |
| 2253 | 0.004 | 0.21 |
| 2255 | 0.055 | 0.70 |
| 2260 | 0.060 | 0.27 |
| 2273 | 0.052 | 0.72 |
| 2282 | 0.043 | 0.29 |
| 2287 | 0.009 | 0.22 |
| 2288 | 0.024 | 0.15 |
| 2313 | 0.013 | 0.74 |
| 2320 | 0.051 | 0.72 |
| 2344 | 0.028 | 0.71 |
| 2362 | 0.031 | 0.76 |
| 2368 | 0.013 | 0.74 |
| 2372 | 0.035 | 0.72 |
| 2373 | 0.002 | 0.85 |
| 2377 | 0.009 | 0.77 |
| 2382 | 0.029 | 0.73 |
| 2402 | 0.012 | 0.83 |
| 2411 | 0.077 | 0.70 |
| 2420 | 0.043 | 0.73 |
| 2454 | 0.015 | 0.75 |
| 2466 | 0.041 | 0.70 |
| 2470 | 0.072 | 0.28 |
| 2471 | 0.039 | 0.76 |
| 2472 | 0.022 | 0.27 |
| 2478 | 0.027 | 0.27 |
| 2485 | 0.033 | 0.33 |
| 2502 | 0.061 | 0.71 |
| 2512 | 0.042 | 0.70 |
| 2521 | 0.031 | 0.32 |
| 2523 | 0.066 | 0.73 |
| 2558 | 0.160 | 0.72 |
| 2571 | 0.013 | 0.76 |
| 2583 | 0.115 | 0.28 |
| 2622 | 0.023 | 0.24 |
| 2625 | 0.027 | 0.72 |
| 2637 | 0.046 | 0.31 |
| 2657 | 0.036 | 0.65 |
| 2658 | 0.040 | 0.28 |
| 2677 | 0.022 | 0.75 |
| 2692 | 0.052 | 0.29 |
| 2699 | 0.020 | 0.27 |
| 2703 | 0.020 | 0.76 |
| 2712 | 0.091 | 0.30 |
| 2737 | 0.072 | 0.70 |
| 2742 | 0.034 | 0.73 |
| 2750 | 0.000 | 0.88 |
| 2791 | 0.045 | 0.28 |
| 2825 | 0.046 | 0.72 |
| 2830 | 0.013 | 0.76 |
| 2856 | 0.017 | 0.73 |
| 2875 | 0.019 | 0.26 |
| 2880 | 0.054 | 0.28 |
| 2883 | 0.028 | 0.35 |
| 2896 | 0.012 | 0.25 |
| 2912 | 0.102 | 0.72 |
| 2928 | 0.033 | 0.69 |
| 2957 | 0.048 | 0.31 |
| 2968 | 0.045 | 0.28 |
| 2982 | 0.002 | 0.19 |
| 2984 | 0.043 | 0.28 |
| 2998 | 0.005 | 0.79 |
| 3006 | 0.026 | 0.72 |
| 3010 | 0.016 | 0.23 |
| 3053 | 0.013 | 0.76 |
| 3054 | 0.019 | 0.27 |
| 3056 | 0.030 | 0.71 |
| 3061 | 0.023 | 0.71 |
| 3064 | 0.023 | 0.77 |
| 3080 | 0.033 | 0.26 |
| 3084 | 0.034 | 0.73 |
| 3096 | 0.044 | 0.31 |
| 3104 | 0.070 | 0.30 |
| 3112 | 0.010 | 0.22 |
| 3125 | 0.041 | 0.71 |
| 3128 | 0.041 | 0.32 |
| 3133 | 0.080 | 0.70 |
| 3137 | 0.163 | 0.73 |
| 3184 | 0.049 | 0.28 |
| 3187 | 0.038 | 0.30 |
| 3193 | 0.065 | 0.71 |
| 3196 | 0.030 | 0.29 |
| 3197 | 0.029 | 0.71 |
| 3200 | 0.015 | 0.26 |
| 3210 | 0.036 | 0.70 |
| 3215 | 0.012 | 0.24 |
| 3230 | 0.012 | 0.27 |
| 3231 | 0.016 | 0.75 |

For this classification, the 2 groups (low LVEF (LVEF≤45) and high LVEF (LVEF>45)) have the same number of samples. The variable selection was performed by using a Random Forest model. A combination of 11 preselected lncRNAs through a Random Forest Classifier (Table 10) is the best predictive model obtained here. The lncRNAs were selected using a random forest algorithm. This model has an area under the receiver-operating characteristic curve (AUC) of 0.996, an accuracy of 0.933, a sensitivity of 0.882, a specificity of 1, a Positive Predictive Value (PPV) of 1 and Negative Predictive Value (PNV) of 0.867. The confusion matrix is presented in Table 11.

TABLE 10

List of 11 pre-selected lncRNAs through a Random Forest Classifier for the classification low LVEF (LVEF ≤ 45) and high LVEF (LVEF > 45)

| lncRNA | Ranking |
| --- | --- |
| SEQ ID NO: 2373 | 1 |
| SEQ ID NO: 1748 | 2 |
| SEQ ID NO: 3112 | 3 |
| SEQ ID NO: 1231 | 4 |
| SEQ ID NO: 0664 | 5 |
| SEQ ID NO: 1686 | 6 |
| SEQ ID NO: 0791 | 7 |
| SEQ ID NO: 2126 | 8 |
| SEQ ID NO: 2750 | 9 |
| SEQ ID NO: 3010 | 10 |
| SEQ ID NO: 2241 | 11 |

TABLE 11

Confusion matrix

| | Low LVEF predicted | High LVEF predicted |
| --- | --- | --- |
| Low LVEF real | 15 | 2 |
| High LVEF real | 0 | 13 |

Correlation Between LncRNA and Left Ventricular Ejection Fraction

Instead of applying a threshold to predict patients as HF or non HF, the expression level of LncRNAs can be considered as a continuous value. For this approach, spearman correlation factor is calculated to measure the correlation between LVEF value at one month and expression level of LncRNA. When a threshold of (+or −) 0.45 for correlation factor is applied, the expression of 73 lncRNAs are positively or negatively correlated with LVEF at 1 month. Among these 73 lncRNAs, 26 have a positive correlation factor whereas 47 have a negative correlation factor (Table 12).

TABLE 12

List of 73 lncRNA with spearman correlation factor higher than 0.45 (absolute value)

| LncRNA (SEQ ID NO:) | Correlation |
| --- | --- |
| 0005 | −0.52414 |
| 0008 | −0.45621 |
| 0069 | −0.56061 |
| 0173 | −0.52934 |
| 0285 | −0.47612 |
| 0321 | −0.52163 |
| 0334 | −0.49958 |
| 0352 | 0.60914 |
| 0398 | 0.607739 |
| 0544 | 0.46328 |
| 0566 | 0.461135 |
| 0586 | 0.510946 |
| 0664 | 0.547218 |
| 0688 | −0.45551 |
| 0758 | −0.46513 |
| 0914 | −0.55591 |
| 1109 | −0.5676 |
| 1144 | −0.45238 |
| 1204 | −0.45716 |
| 1281 | 0.466222 |
| 1385 | −0.45266 |
| 1398 | −0.50488 |
| 1406 | −0.55967 |
| 1428 | −0.5583 |
| 1564 | −0.61193 |
| 1626 | 0.457149 |
| 1674 | 0.566205 |
| 1707 | 0.467787 |
| 1715 | 0.477576 |
| 1804 | −0.48111 |
| 1858 | −0.52538 |
| 1869 | −0.4541 |
| 2100 | 0.534861 |
| 2157 | −0.52703 |
| 2216 | −0.53537 |
| 2253 | −0.50086 |
| 2281 | −0.46295 |
| 2287 | −0.63378 |
| 2311 | −0.58252 |
| 2368 | 0.510665 |
| 2373 | −0.55046 |
| 2377 | −0.45729 |
| 2382 | −0.48369 |
| 2402 | −0.51064 |
| 2454 | −0.48739 |
| 2470 | 0.495523 |
| 2472 | −0.46052 |
| 2478 | −0.46735 |
| 2501 | 0.470795 |
| 2523 | −0.51113 |
| 2545 | −0.49398 |
| 2593 | −0.4538 |
| 2637 | 0.455663 |
| 2645 | −0.49274 |
| 2703 | 0.459314 |
| 2742 | −0.45062 |
| 2746 | −0.47907 |
| 2750 | 0.542019 |
| 2753 | 0.514263 |
| 2830 | 0.460882 |
| 2896 | 0.499645 |
| 2928 | 0.463878 |
| 2930 | −0.48812 |
| 2971 | 0.50357 |
| 2973 | 0.483104 |
| 2982 | −0.4529 |
| 2998 | 0.49442 |
| 3013 | 0.476852 |
| 3080 | −0.48109 |
| 3128 | −0.66808 |
| 3196 | −0.49516 |
| 3200 | 0.536685 |
| 3230 | −0.50558 |

Example 4: lncRNA Detection in Serum Samples with a Targeted lncRNA-Seq (FiMICS) Protocol Circulating lncRNAs in body fluids such as whole blood, serum or plasma are numerous and released from many different tissues. Thus, performing total RNA sequencing on peripheral samples implies to generate a high amount of data to get sufficient data on the lncRNAs of interest. To optimize cardiac lncRNA quantification in peripheral blood samples, a targeted sequencing kit is developed to specifically quantify the cardiac lncRNAs of interest. For this purpose, capture probes of 50 nucleotides specific and complementary to the sequence of lncRNAs associated to the cardiac tissue (SEQ ID NO 1 to SEQ ID NO 3238) are designed. Each probe covers region of 200 bp. Multiple probes are designed for each lncRNA over 200 bp to cover specific region. Maximum probe coverage is limited to 2000 nucleotides. Celemics technology was used to develop the assay but similar technologies using capture probes for targeting sequencing panel can be used.

Material and Methods:

Serum samples collected at discharge of patient between D3 and D5 from 30 patients with AMI from the MitoCare cohort were used for lncRNA profiling. Mitocare is a multicenter, randomized, double-blind, placebo controlled study. The study population includes AMI patients undergoing PCI, older than 18 years. The primary endpoint is the level of left ventricular ejection fraction (LVEF) less than 40% at 1 month. Demographics of the patients are presented in Table 13. Control serum samples were selected from subjects of ADDIA Chronobiological study.

TABLE 13

Demographic data for Mitocare patients used with Fi-MICS test

|  | Group 1 | Group 2 | Group 3 |
|---|---|---|---|
| EF | <40 | 41-50 | >50 |
| Nb | 6 | 6 | 5 |
| Age | 62.8 | 63.8 | 59.9 |
| Male | 100% | 83% | 60% |
| BMI | 27.9 | 28.0 | 27.6 |
| Systolic Blood Pressure | 108 | 123.5 | 117.4 |
| Diastolic Blood Pressure | 70.5 | 70.7 | 66.2 |
| Heart Rate | 83.0 | 79.6 | 67.4 |

Sequencing libraries constructed in Example 3 from Serum RNA of 18 patients who suffered AMI, (6 who developed heart failure (HF) and 12 who did not) and 6 control subjects are used. The lncRNA capture panel called Fi-MICS kit is used to capture 3238 cardiac lncRNAs of interest, according to the manufacturer instructions. Briefly, biotinylated target capture probes, specific for the lncRNAs of interest, are hybridized to the sequencing libraries for 24 hours. So, captured lncRNA sequences are purified on T1 streptavidin coated magnetic beads. Six successive washes are performed to eliminate all libraries sequences not specific to the panel probes. Finally, captures sequenced are enriched by PCR (14 cycles) and PCR products are purified with a final AMPure XP beads wash. Captured libraries are eluted in 30 µl of nuclease-free water.

For quality control, 1 µl of each library is run on the Agilent Technologies 2100 Bioanalyzer using a DNA 1000 chip according to the manufacturer's recommendations. Absence of adapter dimers is checked and the average library size is determined by a region table. Libraries are quantified on Qubit 2.0 using Qubit dsDNA High Sensitivity assay kit (Invitrogen). Library size previously determined on the Bioanalyzer is used to calculate molar concentrations from mass concentrations. All libraries are sequenced using the Illumina NextSeq500 (2×75 bp).

Sequencing Analysis and Statistical Analysis

The read alignment and the quantification are performed as described in Example 3. The transcript counts were normalized by CPM (counts per millions). To determine differentially expressed lncRNAs, a statistical analysis is performed using a non-parametric Wilcoxon-Mann-Whitney test and a parametric T-test. A lncRNA with a p-value≤0.05 is considered as differentially expressed.

Results:

Coverage in Targeted Sequencing is Improved

Figure 5:
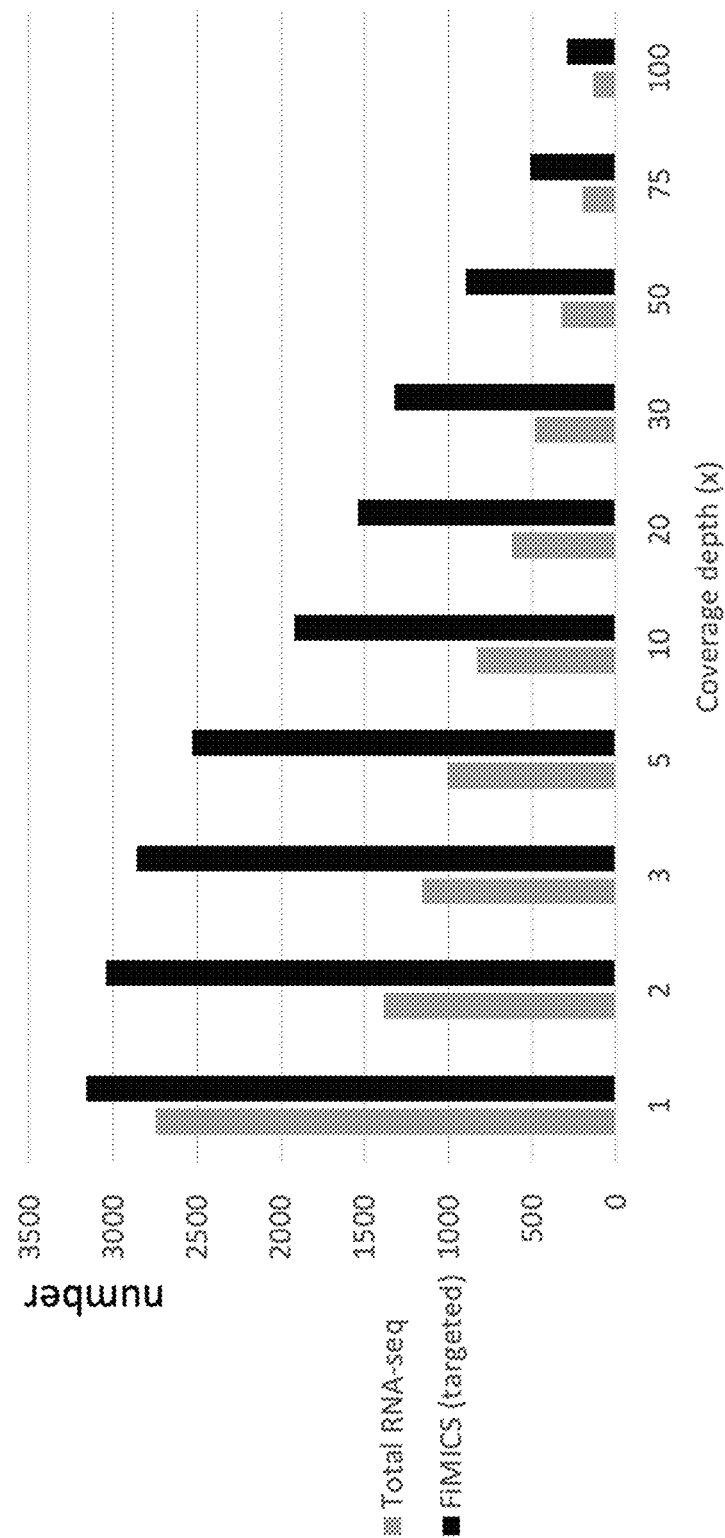
FIG. 5 shows a histogram with the number of lncRNA, which passed the different threshold of coverage depth (in horizontal axis). In total RNA-seq protocol (left bar), half of 3238 lncRNA have an average coverage depth less than 2×. In FiMICS (targeted sequencing) protocol (right bar), more than 3000 lncRNA have at least an average coverage depth of 2×.

The average coverage depth across all bases in the sample is the sum of the read depths of each base in each region divided by the sum of the lengths of every region. Using the Fi-MICS kit, the average coverage is improved (11 times better in average with equivalent number of reads) compared to a total RNA-seq protocol, as shown in Table 14. Among the 3238 lncRNAs present in the panel, 2432 lncRNAs passed the threshold of 10 CPM in serum samples. Detection and quantification in function of coverage depth is presented in FIG. 5. Whereas 2744 lncRNAs are measured with a coverage of at least 1× by total RNA-Seq experiment, 3162 lncRNAs are measured with a coverage of at least 1× with FiMICS panel with 10 fold less reads generated. At a coverage of at least 2×, half of the lncRNAs are excluded with total-RNA-Seq approach (1385) whereas 3041 lncR-NAs are passing the threshold in FiMICS panel. Efficiency of the targeted panel is highly enhanced (FIG. 5). The FiMICS (targeted sequencing) detects more lncRNA in terms of numbers of lncRNAs and their level of expression and thus using much less total sequencing reads.

TABLE 14

Number of reads and average coverage for 18 samples in the 2 sequencing protocols

|  | Total RNA-seq protocol | | Targeted RNA-seq protocol | |
|---|---|---|---|---|
| Sample name | Total reads | Average coverage depth | Total reads | Average coverage depth |
| Sample 1 | 35,545,396 | 62.01 | 4,113,215 | 135.54 |
| Sample 2 | 34,427,599 | 70.57 | 5,051,804 | 107.11 |
| Sample 3 | 27,820,331 | 64.19 | 7,664,878 | 100.01 |
| Sample 4 | 46,070,066 | 87.04 | 5,939,425 | 94.2 |
| Sample 5 | 37,846,232 | 76.60 | 5,251,571 | 96.98 |
| Sample 6 | 45,285,008 | 51.97 | 8,649,560 | 118.7 |
| Sample 7 | 63,215,798 | 88.00 | 5,342,296 | 99.26 |
| Sample 8 | 37,467,050 | 67.20 | 6,552,391 | 93.25 |
| Sample 9 | 65,796,180 | 87.51 | 6,602,505 | 129.06 |
| Sample 10 | 50,693,623 | 48.89 | 5,043,709 | 76.41 |
| Sample 11 | 64,165,816 | 88.80 | 6,586,358 | 83.5 |
| Sample 12 | 33,302,080 | 54.82 | 6,725,419 | 105.28 |
| Sample 13 | 29,673,123 | 50.11 | 8,178,840 | 123.15 |
| Sample 14 | 56,386,693 | 76.81 | 5,613,486 | 105.63 |
| Sample 15 | 75,267,997 | 107.00 | 6,789,160 | 124.8 |
| Sample 16 | 40,789,456 | 66.70 | 5,875,488 | 81.59 |
| Sample 17 | 54,651,503 | 78.11 | 7,038,893 | 85.31 |
| Sample 18 | 66,866,920 | 78.91 | 5,275,438 | 82.16 |

Comparison Between Samples after Myocardial Infarction and Control Samples

First, the statistical analysis was performed by comparing 18 samples after myocardial infarction (AMI) and 6 control samples with the goal to diagnose myocardial infraction. The volcano plot showed the differential expression of lncRNA. 20 lncRNAs are differentially expressed between the samples AMI and the control samples. The p-value and the fold-change of these lncRNA are listed in the Table 15.

TABLE 15

List of 20 lncRNAs which are differentially expressed between samples AMI and control samples

| lncRNA | p-value | Fold change |
|---|---|---|
| SEQ ID NO: 0097 | 1.35E−05 | 0.446 |
| SEQ ID NO: 2114 | 0.00194062 | 0.477 |
| SEQ ID NO: 0534 | 0.02513143 | 0.354 |
| SEQ ID NO: 1404 | 0.0128132 | 0.486 |
| SEQ ID NO: 0311 | 0.00046383 | 0.217 |
| SEQ ID NO: 1262 | 0.01381743 | 0.412 |
| SEQ ID NO: 0990 | 0.00060722 | 0.182 |
| SEQ ID NO: 1300 | 0.04098375 | 0.364 |
| SEQ ID NO: 0978 | 0.00358642 | 0.498 |
| SEQ ID NO: 0215 | 0.00013071 | 0.369 |
| SEQ ID NO: 0288 | 0.04991173 | 0.392 |

TABLE 15-continued

List of 20 lncRNAs which are differentially expressed
between samples AMI and control samples

| lncRNA | p-value | Fold change |
|---|---|---|
| SEQ ID NO: 1418 | 0.00010606 | 0.450 |
| SEQ ID NO: 2070 | 0.00078855 | 0.457 |
| SEQ ID NO: 0309 | 0.00322822 | 0.141 |
| SEQ ID NO: 0597 | 0.0182368 | 0.401 |
| SEQ ID NO: 1875 | 0.0343985 | 0.457 |
| SEQ ID NO: 1984 | 0.0108457 | 0.479 |
| SEQ ID NO: 0538 | 3.89E−05 | 0.386 |
| SEQ ID NO: 1871 | 0.00021278 | 0.360 |

For this classification, a combination of 14 pre-selected lncRNA through a Random Forest Classifier (Table 16) is the best predictive model obtained here. The lncRNAs were selected using a random forest algorithm. This model has an area under the receiver-operating characteristic curve (AUC) of 0.971, an accuracy of 0.870, a sensitivity of 0.941, a specificity of 0.667, a Positive Predictive Value (PPV) of 0.889 and Negative Predictive Value (PNV) of 0.800. The confusion matrix is presented in Table 17.

TABLE 16

List of 14 pre-selected lncRNAs through a Random Forest
Classifier for the classification between the samples
AMI and the control samples

| lncRNA | rank |
|---|---|
| SEQ ID NO: 2150 | 1 |
| SEQ ID NO: 1534 | 2 |
| SEQ ID NO: 0311 | 3 |
| SEQ ID NO: 2952 | 4 |
| SEQ ID NO: 2838 | 5 |
| SEQ ID NO: 1437 | 6 |
| SEQ ID NO: 1297 | 7 |
| SEQ ID NO: 1059 | 8 |
| SEQ ID NO: 1465 | 9 |
| SEQ ID NO: 2826 | 10 |
| SEQ ID NO: 0180 | 11 |
| SEQ ID NO: 0538 | 12 |
| SEQ ID NO: 0258 | 13 |
| SEQ ID NO: 2273 | 14 |

TABLE 17

Confusion matrix of the Random Forest model

| | Predicted AMI | Predicted Control |
|---|---|---|
| Real Control | 4 | 2 |
| True AMI | 1 | 16 |

Comparison Between Low LVEF (LVEF≤40) and High LVEF (LVEF>40)

In this analysis, the 18 samples AMI were grouped into 2 groups based on the 1-month LVEF: low LVEF (LVEF≤40) and high LVEF (LVEF>40). The volcano plot showed the differential expression of lncRNA. 95 lncRNAs are differentially expressed and among them, 6 lncRNAs are differentially expressed with a fold change>2 or <0.5 between the samples with low LVEF and the samples with high LVEF. The p-value and the fold-change and individual AUC of these 6 lncRNAs are listed in the Table 18 and 353 lncRNAs which have a P<0.05 and/or an individual AUC>0.7 or <0.3 are listed in Table 19.

TABLE 18

List of 6 lncRNAs which are differentially expressed and have a fold
change >2 or <0.5 between the low LVEF group (LVEF ≤ 40)
and the high LVEF group (LVEF > 40)

| lncRNA | p-value | Fold change | Individual AUC |
|---|---|---|---|
| SEQ ID NO: 0631 | 0.022 | 2.497 | 0.848 |
| SEQ ID NO: 0758 | 0.030 | 0.354 | 0.242 |
| SEQ ID NO: 0789 | 0.030 | 0.388 | 0.258 |
| SEQ ID NO: 1399 | 0.021 | 0.163 | 0.242 |
| SEQ ID NO: 2914 | 0.012 | 2.493 | 0.985 |
| SEQ ID NO: 2924 | 0.147 | 2.232 | 0.727 |

TABLE 19

List of 353 lncRNAs which are differentially expressed and/or
have an AUC >0.7 or <0.3 between the low LVEF group
(LVEF ≤ 40) and the high LVEF group (LVEF > 40)

| LncRNA (SEQ ID NO:) | p-value | AUC |
|---|---|---|
| 0002 | 0.006 | 0.939 |
| 0006 | 0.965 | 0.712 |
| 0007 | 0.199 | 0.712 |
| 0008 | 0.224 | 0.288 |
| 0018 | 0.5 | 0.258 |
| 0019 | 0.027 | 0.182 |
| 0023 | 0.127 | 0.742 |
| 0041 | 0.091 | 0.258 |
| 0042 | 0.151 | 0.242 |
| 0048 | 0.145 | 0.288 |
| 0057 | 0.163 | 0.712 |
| 0060 | 0.192 | 0.288 |
| 0094 | 0.264 | 0.773 |
| 0106 | 0.168 | 0.273 |
| 0117 | 0.097 | 0.727 |
| 0120 | 0.642 | 0.288 |
| 0134 | 0.075 | 0.212 |
| 0149 | 0.448 | 0.712 |
| 0151 | 0.011 | 0.182 |
| 0155 | 0.023 | 0.833 |
| 0190 | 0.05 | 0.242 |
| 0191 | 0.064 | 0.818 |
| 0205 | 0.047 | 0.212 |
| 0208 | 0.051 | 0.197 |
| 0222 | 0.018 | 0.833 |
| 0228 | 0.171 | 0.712 |
| 0236 | 0.06 | 0.788 |
| 0239 | 0.121 | 0.712 |
| 0241 | 0.097 | 0.288 |
| 0242 | 0.462 | 0.727 |
| 0285 | 0.149 | 0.758 |
| 0295 | 0.076 | 0.273 |
| 0308 | 0.12 | 0.273 |
| 0312 | 0.075 | 0.212 |
| 0334 | 0.021 | 0.864 |
| 0345 | 0.107 | 0.758 |
| 0350 | 0.017 | 0.152 |
| 0354 | 0.346 | 0.727 |
| 0358 | 0.161 | 0.288 |
| 0362 | 0.25 | 0.273 |
| 0366 | 0.095 | 0.758 |
| 0371 | 0.349 | 0.258 |
| 0380 | 0.141 | 0.727 |
| 0384 | 0.026 | 0.803 |
| 0394 | 0.029 | 0.152 |
| 0412 | 0.342 | 0.227 |
| 0434 | 0.179 | 0.712 |
| 0441 | 0.05 | 0.197 |
| 0443 | 0.211 | 0.712 |
| 0445 | 0.446 | 0.288 |
| 0460 | 0.046 | 0.227 |
| 0468 | 0.059 | 0.727 |
| 0469 | 0.09 | 0.288 |
| 0487 | 0.091 | 0.212 |
| 0502 | 0.106 | 0.758 |
| 0542 | 0.068 | 0.727 |

TABLE 19-continued

List of 353 lncRNAs which are differentially expressed and/or have an AUC >0.7 or <0.3 between the low LVEF group (LVEF ≤ 40) and the high LVEF group (LVEF > 40)

| LncRNA (SEQ ID NO:) | p-value | AUC |
| --- | --- | --- |
| 0547 | 0.016 | 0.803 |
| 0551 | 0.196 | 0.742 |
| 0552 | 0.042 | 0.833 |
| 0561 | 0.192 | 0.712 |
| 0581 | 0.057 | 0.758 |
| 0597 | 0.108 | 0.742 |
| 0601 | 0.075 | 0.803 |
| 0604 | 0.284 | 0.258 |
| 0612 | 0.071 | 0.288 |
| 0621 | 0.21 | 0.742 |
| 0629 | 0.176 | 0.758 |
| 0631 | 0.022 | 0.848 |
| 0659 | 0.052 | 0.848 |
| 0661 | 0.157 | 0.742 |
| 0670 | 0.053 | 0.742 |
| 0677 | 0.035 | 0.788 |
| 0680 | 0.045 | 0.227 |
| 0681 | 0.047 | 0.773 |
| 0701 | 0.159 | 0.212 |
| 0702 | 0.365 | 0.712 |
| 0724 | 0.058 | 0.742 |
| 0726 | 0.515 | 0.712 |
| 0729 | 0.017 | 0.864 |
| 0730 | 0.076 | 0.818 |
| 0732 | 0.098 | 0.758 |
| 0751 | 0.03 | 0.212 |
| 0758 | 0.03 | 0.242 |
| 0766 | 0.033 | 0.803 |
| 0779 | 0.36 | 0.742 |
| 0789 | 0.03 | 0.258 |
| 0821 | 0.004 | 0.864 |
| 0823 | 0.117 | 0.273 |
| 0829 | 0.143 | 0.227 |
| 0841 | 0.063 | 0.773 |
| 0844 | 0.021 | 0.136 |
| 0847 | 0.107 | 0.288 |
| 0868 | 0.228 | 0.242 |
| 0884 | 0.322 | 0.288 |
| 0891 | 0.044 | 0.742 |
| 0915 | 0.077 | 0.758 |
| 0926 | 0.285 | 0.288 |
| 0937 | 0.075 | 0.727 |
| 0938 | 0.271 | 0.742 |
| 0946 | 0.008 | 0.833 |
| 0956 | 0.012 | 0.879 |
| 0958 | 0.027 | 0.818 |
| 0960 | 0.036 | 0.788 |
| 0981 | 0.07 | 0.288 |
| 0986 | 0.044 | 0.788 |
| 1005 | 0.178 | 0.712 |
| 1052 | 0.221 | 0.727 |
| 1065 | 0.045 | 0.212 |
| 1075 | 0.025 | 0.197 |
| 1076 | 0.275 | 0.288 |
| 1089 | 0.002 | 0.97 |
| 1093 | 0.037 | 0.197 |
| 1109 | 0.114 | 0.788 |
| 1111 | 0.139 | 0.288 |
| 1146 | 0.039 | 0.182 |
| 1156 | 0.28 | 0.742 |
| 1162 | 0.019 | 0.803 |
| 1164 | 0.181 | 0.273 |
| 1179 | 0.078 | 0.197 |
| 1186 | 0.135 | 0.273 |
| 1191 | 0.064 | 0.242 |
| 1204 | 0.012 | 0.848 |
| 1207 | 0.047 | 0.864 |
| 1217 | 0.13 | 0.742 |
| 1232 | 0.086 | 0.773 |
| 1252 | 0.208 | 0.273 |
| 1273 | 0.016 | 0.182 |
| 1288 | 0.021 | 0.197 |
| 1326 | 0.056 | 0.258 |
| 1333 | 0.199 | 0.712 |
| 1338 | 0.097 | 0.288 |
| 1350 | 0.162 | 0.242 |
| 1354 | 0.059 | 0.803 |
| 1399 | 0.021 | 0.242 |
| 1403 | 0.063 | 0.788 |
| 1405 | 0.17 | 0.727 |
| 1412 | 0.097 | 0.712 |
| 1422 | 0.04 | 0.758 |
| 1433 | 0.056 | 0.258 |
| 1439 | 0.029 | 0.152 |
| 1449 | 0.073 | 0.227 |
| 1459 | 0.125 | 0.242 |
| 1465 | 0.182 | 0.288 |
| 1467 | 0.067 | 0.742 |
| 1475 | 0.034 | 0.242 |
| 1476 | 0.022 | 0.833 |
| 1484 | 0.124 | 0.288 |
| 1485 | 0.143 | 0.727 |
| 1515 | 0.014 | 0.136 |
| 1516 | 0.076 | 0.818 |
| 1527 | 0.185 | 0.273 |
| 1534 | 0.038 | 0.212 |
| 1535 | 0.284 | 0.712 |
| 1556 | 0.133 | 0.727 |
| 1573 | 0.045 | 0.258 |
| 1578 | 0.197 | 0.742 |
| 1580 | 0.229 | 0.712 |
| 1598 | 0.146 | 0.712 |
| 1624 | 0.048 | 0.227 |
| 1635 | 0.089 | 0.758 |
| 1660 | 0.014 | 0.864 |
| 1661 | 0.038 | 0.258 |
| 1678 | 0.075 | 0.258 |
| 1696 | 0.231 | 0.288 |
| 1710 | 0.056 | 0.742 |
| 1722 | 0.091 | 0.864 |
| 1740 | 0.162 | 0.712 |
| 1744 | 0.021 | 0.167 |
| 1754 | 0.453 | 0.727 |
| 1760 | 0.086 | 0.727 |
| 1773 | 0.146 | 0.288 |
| 1806 | 0.168 | 0.258 |
| 1816 | 0.06 | 0.833 |
| 1818 | 0.106 | 0.288 |
| 1833 | 0.14 | 0.273 |
| 1852 | 0.008 | 0.864 |
| 1853 | 0.069 | 0.227 |
| 1854 | 0.164 | 0.773 |
| 1860 | 0.19 | 0.727 |
| 1862 | 0.107 | 0.258 |
| 1871 | 0.096 | 0.288 |
| 1872 | 0.142 | 0.712 |
| 1880 | 0.377 | 0.712 |
| 1896 | 0.083 | 0.227 |
| 1903 | 0.105 | 0.227 |
| 1908 | 0.066 | 0.758 |
| 1912 | 0.049 | 0.258 |
| 1937 | 0.098 | 0.773 |
| 1939 | 0.139 | 0.197 |
| 1959 | 0.012 | 0.212 |
| 1962 | 0.094 | 0.258 |
| 1992 | 0.049 | 0.227 |
| 1995 | 0.06 | 0.773 |
| 2000 | 0.06 | 0.197 |
| 2021 | 0.037 | 0.212 |
| 2022 | 0.27 | 0.258 |
| 2050 | 0.117 | 0.273 |
| 2084 | 0.104 | 0.788 |
| 2086 | 0.065 | 0.242 |
| 2091 | 0.214 | 0.712 |
| 2109 | 0.22 | 0.242 |
| 2141 | 0.128 | 0.242 |
| 2149 | 0.071 | 0.227 |
| 2151 | 0.064 | 0.242 |

TABLE 19-continued

List of 353 lncRNAs which are differentially expressed and/or have an AUC >0.7 or <0.3 between the low LVEF group (LVEF ≤ 40) and the high LVEF group (LVEF > 40)

| LncRNA (SEQ ID NO:) | p-value | AUC |
|---|---|---|
| 2161 | 0.051 | 0.273 |
| 2170 | 0.099 | 0.227 |
| 2172 | 0.023 | 0.773 |
| 2174 | 0.01 | 0.848 |
| 2192 | 0.013 | 0.864 |
| 2198 | 0.027 | 0.803 |
| 2205 | 0.047 | 0.758 |
| 2207 | 0.088 | 0.197 |
| 2218 | 0.078 | 0.788 |
| 2220 | 0.105 | 0.758 |
| 2221 | 0.105 | 0.788 |
| 2226 | 0.214 | 0.712 |
| 2227 | 0.058 | 0.258 |
| 2235 | 0.032 | 0.167 |
| 2238 | 0.024 | 0.197 |
| 2244 | 0.102 | 0.742 |
| 2273 | 0.098 | 0.773 |
| 2285 | 0.107 | 0.242 |
| 2286 | 0.16 | 0.712 |
| 2294 | 0.079 | 0.803 |
| 2311 | 0.388 | 0.273 |
| 2318 | 0.114 | 0.758 |
| 2325 | 0.482 | 0.288 |
| 2327 | 0.097 | 0.727 |
| 2338 | 0.012 | 0.818 |
| 2341 | 0.086 | 0.242 |
| 2345 | 0.102 | 0.227 |
| 2364 | 0.149 | 0.742 |
| 2368 | 0.045 | 0.742 |
| 2371 | 0.144 | 0.258 |
| 2375 | 0.01 | 0.121 |
| 2379 | 0.029 | 0.773 |
| 2395 | 0.113 | 0.773 |
| 2406 | 0.018 | 0.182 |
| 2407 | 0.27 | 0.773 |
| 2411 | 0.02 | 0.864 |
| 2422 | 0.138 | 0.742 |
| 2425 | 0.15 | 0.712 |
| 2429 | 0.049 | 0.212 |
| 2436 | 0.11 | 0.758 |
| 2440 | 0.238 | 0.258 |
| 2441 | 0.067 | 0.242 |
| 2451 | 0.205 | 0.712 |
| 2454 | 0.054 | 0.758 |
| 2475 | 0.045 | 0.197 |
| 2497 | 0.109 | 0.712 |
| 2513 | 0.189 | 0.712 |
| 2517 | 0.189 | 0.758 |
| 2520 | 0.176 | 0.727 |
| 2529 | 0.256 | 0.273 |
| 2544 | 0.259 | 0.742 |
| 2546 | 0.055 | 0.258 |
| 2553 | 0.196 | 0.242 |
| 2562 | 0.099 | 0.712 |
| 2572 | 0.227 | 0.727 |
| 2584 | 0.206 | 0.288 |
| 2611 | 0.112 | 0.288 |
| 2613 | 0.105 | 0.758 |
| 2621 | 0.152 | 0.727 |
| 2627 | 0.068 | 0.788 |
| 2629 | 0.093 | 0.712 |
| 2639 | 0.131 | 0.288 |
| 2640 | 0.08 | 0.727 |
| 2641 | 0.379 | 0.742 |
| 2656 | 0.085 | 0.712 |
| 2676 | 0.03 | 0.864 |
| 2677 | 0.082 | 0.212 |
| 2680 | 0.161 | 0.727 |
| 2681 | 0.07 | 0.788 |
| 2683 | 0.053 | 0.818 |
| 2684 | 0.076 | 0.197 |
| 2692 | 0.047 | 0.242 |
| 2713 | 0.052 | 0.803 |
| 2735 | 0.261 | 0.712 |
| 2737 | 0.035 | 0.848 |
| 2754 | 0.133 | 0.212 |
| 2760 | 0.135 | 0.273 |
| 2767 | 0.156 | 0.727 |
| 2768 | 0.14 | 0.758 |
| 2784 | 0.09 | 0.742 |
| 2788 | 0.15 | 0.288 |
| 2789 | 0.426 | 0.727 |
| 2796 | 0.162 | 0.773 |
| 2806 | 0.058 | 0.773 |
| 2819 | 0.111 | 0.727 |
| 2827 | 0.024 | 0.894 |
| 2834 | 0.098 | 0.288 |
| 2841 | 0.014 | 0.818 |
| 2856 | 0.13 | 0.273 |
| 2857 | 0.135 | 0.742 |
| 2870 | 0.035 | 0.212 |
| 2881 | 0.014 | 0.818 |
| 2903 | 0.19 | 0.712 |
| 2911 | 0.177 | 0.742 |
| 2914 | 0.012 | 0.985 |
| 2917 | 0.226 | 0.712 |
| 2924 | 0.147 | 0.727 |
| 2939 | 0.06 | 0.258 |
| 2945 | 0.727 | 0.727 |
| 2955 | 0.089 | 0.288 |
| 2958 | 0.071 | 0.758 |
| 2959 | 0.34 | 0.879 |
| 2961 | 0.009 | 0.121 |
| 2963 | 0.114 | 0.758 |
| 2967 | 0.042 | 0.227 |
| 2969 | 0.22 | 0.727 |
| 2973 | 0.17 | 0.773 |
| 2982 | 0.069 | 0.818 |
| 2995 | 0.063 | 0.273 |
| 3001 | 0.088 | 0.727 |
| 3007 | 0.217 | 0.712 |
| 3013 | 0.059 | 0.758 |
| 3015 | 0.147 | 0.727 |
| 3029 | 0.03 | 0.212 |
| 3035 | 0.004 | 0.136 |
| 3036 | 0.071 | 0.818 |
| 3052 | 0.064 | 0.773 |
| 3053 | 0.002 | 0.909 |
| 3058 | 0.037 | 0.803 |
| 3060 | 0.371 | 0.712 |
| 3064 | 0.048 | 0.758 |
| 3065 | 0.16 | 0.742 |
| 3069 | 0.328 | 0.258 |
| 3090 | 0.046 | 0.773 |
| 3091 | 0.161 | 0.712 |
| 3098 | 0.094 | 0.212 |
| 3101 | 0.102 | 0.833 |
| 3107 | 0.221 | 0.258 |
| 3124 | 0.008 | 0.864 |
| 3130 | 0.134 | 0.742 |
| 3134 | 0.158 | 0.727 |
| 3142 | 0.111 | 0.242 |
| 3146 | 0.114 | 0.712 |
| 3147 | 0.237 | 0.273 |
| 3148 | 0.33 | 0.758 |
| 3169 | 0.138 | 0.742 |
| 3172 | 0.033 | 0.758 |
| 3176 | 0.037 | 0.879 |
| 3183 | 0.006 | 0.909 |
| 3190 | 0.085 | 0.788 |
| 3195 | 0.186 | 0.273 |
| 3196 | 0.036 | 0.773 |
| 3197 | 0.119 | 0.758 |
| 3199 | 0.081 | 0.788 |
| 3208 | 0.015 | 0.197 |
| 3209 | 0.133 | 0.258 |
| 3213 | 0.027 | 0.152 |

TABLE 19-continued

List of 353 lncRNAs which are differentially expressed and/or have an AUC >0.7 or <0.3 between the low LVEF group (LVEF ≤ 40) and the high LVEF group (LVEF > 40)

| LncRNA (SEQ ID NO:) | p-value | AUC |
|---|---|---|
| 3222 | 0.051 | 0.197 |
| 3236 | 0.293 | 0.712 |

Comparison Between Low LVEF (LVEF<45) and High LVEF (LVEF>45)

In this analysis, the 18 samples AMI were grouped into 2 groups using the threshold of 45% LVEF: low LVEF (LVEF≤45) and high LVEF (LVEF>45). The volcano plot showed the differential expression of lncRNA. 80 lncRNA are differentially expressed and among them, 1 lncRNA has a fold change>2 or <0.5, which is shown in Table 20. 467 lncRNAs which have a P<0.05 and/or an individual AUC>0.7 or <0.3 are listed in Table 21.

TABLE 20

List of 1 lncRNA which is differentially expressed with a fold change >2 or <0.5 between the low LVEF group (LVEF ≤ 45) and the high LVEF group (LVEF > 45)

| lncRNA | p-value | Fold change | AUC |
|---|---|---|---|
| SEQ ID NO: 2924 | 0.034 | 2.526 | 0.829 |

TABLE 21

List of 467 lncRNAs which are differentially expressed and/or have an AUC > 0.7 or < 0.3 between the low LVEF group (LVEF ≤ 45) and the high LVEF group (LVEF > 45)

| lncRNA (SEQ ID NO:) | p-value | AUC | lncRNA (SEQ ID NO:) | p-value | AUC | lncRNA (SEQ ID NO:) | p-value | AUC | lncRNA (SEQ ID NO:) | p-value | AUC |
|---|---|---|---|---|---|---|---|---|---|---|---|
| 0008 | 0.186 | 0.286 | 0877 | 0.05 | 0.757 | 1708 | 0.298 | 0.3 | 2561 | 0.214 | 0.3 |
| 0023 | 0.152 | 0.743 | 0892 | 0.061 | 0.171 | 1722 | 0.078 | 0.771 | 2576 | 0.01 | 0.114 |
| 0024 | 0.151 | 0.3 | 0897 | 0.074 | 0.257 | 1744 | 0.204 | 0.271 | 2599 | 0.18 | 0.271 |
| 0063 | 0.014 | 0.843 | 0906 | 0.157 | 0.243 | 1754 | 0.13 | 0.714 | 2602 | 0.048 | 0.229 |
| 0067 | 0.09 | 0.757 | 0907 | 0.227 | 0.7 | 1755 | 0.16 | 0.729 | 2606 | 0.021 | 0.857 |
| 0068 | 0.105 | 0.229 | 0933 | 0.122 | 0.229 | 1758 | 0.103 | 0.757 | 2632 | 0.186 | 0.257 |
| 0071 | 0.106 | 0.2 | 0937 | 0.023 | 0.843 | 1771 | 0.057 | 0.2 | 2637 | 0.007 | 0.857 |
| 0076 | 0.18 | 0.729 | 0939 | 0.177 | 0.714 | 1777 | 0.016 | 0.871 | 2647 | 0.171 | 0.286 |
| 0092 | 0.103 | 0.729 | 0940 | 0.105 | 0.743 | 1788 | 0.093 | 0.729 | 2648 | 0.161 | 0.257 |
| 0095 | 0.092 | 0.214 | 0946 | 0.083 | 0.743 | 1815 | 0.108 | 0.743 | 2660 | 0.111 | 0.286 |
| 0104 | 0.286 | 0.3 | 0956 | 0.07 | 0.786 | 1833 | 0.122 | 0.229 | 2675 | 0.306 | 0.286 |
| 0105 | 0.031 | 0.2 | 0958 | 0.066 | 0.771 | 1834 | 0.182 | 0.729 | 2676 | 0.101 | 0.7 |
| 0106 | 0.006 | 0.1 | 0966 | 0.031 | 0.786 | 1842 | 0.099 | 0.743 | 2690 | 0.231 | 0.271 |
| 0107 | 0.143 | 0.729 | 0986 | 0.029 | 0.814 | 1852 | 0.003 | 0.914 | 2692 | 0.153 | 0.271 |
| 0108 | 0.118 | 0.729 | 0993 | 0.102 | 0.729 | 1854 | 0.032 | 0.857 | 2695 | 0.105 | 0.743 |
| 0112 | 0.201 | 0.3 | 1007 | 0.138 | 0.286 | 1882 | 0.06 | 0.143 | 2696 | 0.33 | 0.3 |
| 0113 | 0.146 | 0.3 | 1016 | 0.064 | 0.229 | 1887 | 0.567 | 0.3 | 2701 | 0.111 | 0.3 |
| 0117 | 0.134 | 0.743 | 1025 | 0.023 | 0.214 | 1888 | 0.184 | 0.729 | 2706 | 0.136 | 0.286 |
| 0127 | 0.015 | 0.843 | 1028 | 0.042 | 0.729 | 1903 | 0.126 | 0.186 | 2712 | 0.213 | 0.286 |
| 0130 | 0.07 | 0.757 | 1034 | 0.077 | 0.714 | 1913 | 0.165 | 0.286 | 2726 | 0.051 | 0.229 |
| 0134 | 0.047 | 0.186 | 1036 | 0.052 | 0.186 | 1944 | 0.039 | 0.786 | 2727 | 0.399 | 0.3 |
| 0136 | 0.234 | 0.714 | 1053 | 0.044 | 0.229 | 1947 | 0.1 | 0.757 | 2729 | 0.129 | 0.243 |
| 0139 | 0.089 | 0.771 | 1055 | 0.127 | 0.729 | 1951 | 0.196 | 0.243 | 2735 | 0.241 | 0.729 |
| 0141 | 0.007 | 0.143 | 1056 | 0.151 | 0.7 | 1962 | 0.071 | 0.229 | 2740 | 0.19 | 0.271 |
| 0155 | 0.065 | 0.743 | 1057 | 0.191 | 0.257 | 1972 | 0.129 | 0.757 | 2741 | 0.714 | 0.3 |
| 0161 | 0.162 | 0.7 | 1080 | 0.139 | 0.743 | 1976 | 0.193 | 0.7 | 2745 | 0.086 | 0.729 |
| 0162 | 0.191 | 0.3 | 1086 | 0.045 | 0.786 | 1995 | 0.174 | 0.743 | 2751 | 0.102 | 0.2 |
| 0167 | 0.142 | 0.729 | 1088 | 0.075 | 0.771 | 2003 | 0.106 | 0.729 | 2760 | 0.017 | 0.186 |
| 0170 | 0.151 | 0.257 | 1089 | 0.184 | 0.786 | 2021 | 0.06 | 0.214 | 2765 | 0.208 | 0.7 |
| 0193 | 0.129 | 0.271 | 1093 | 0.129 | 0.271 | 2024 | 0.097 | 0.729 | 2768 | 0.333 | 0.714 |
| 0194 | 0.029 | 0.2 | 1099 | 0.169 | 0.3 | 2031 | 0.032 | 0.186 | 2777 | 0.066 | 0.243 |
| 0200 | 0.186 | 0.3 | 1106 | 0.199 | 0.7 | 2068 | 0.147 | 0.3 | 2785 | 0.029 | 0.2 |
| 0208 | 0.647 | 0.3 | 1109 | 0.141 | 0.771 | 2079 | 0.261 | 0.3 | 2788 | 0.161 | 0.257 |
| 0215 | 0.202 | 0.743 | 1111 | 0.48 | 0.3 | 2082 | 0.052 | 0.771 | 2795 | 0.201 | 0.3 |
| 0217 | 0.099 | 0.3 | 1115 | 0.347 | 0.743 | 2085 | 0.141 | 0.743 | 2796 | 0.276 | 0.7 |
| 0219 | 0.149 | 0.7 | 1116 | 0.1 | 0.771 | 2086 | 0.101 | 0.286 | 2805 | 0.054 | 0.243 |
| 0236 | 0.111 | 0.771 | 1121 | 0.268 | 0.3 | 2109 | 0.12 | 0.271 | 2815 | 0.196 | 0.3 |
| 0239 | 0.011 | 0.771 | 1129 | 0.108 | 0.257 | 2113 | 0.125 | 0.2 | 2827 | 0.061 | 0.771 |
| 0242 | 0.184 | 0.757 | 1136 | 0.069 | 0.214 | 2114 | 0.057 | 0.743 | 2829 | 0.076 | 0.814 |
| 0267 | 0.146 | 0.286 | 1146 | 0.139 | 0.286 | 2131 | 0.005 | 0.1 | 2834 | 0.216 | 0.257 |
| 0273 | 0.14 | 0.757 | 1164 | 0.136 | 0.271 | 2138 | 0.209 | 0.3 | 2852 | 0.145 | 0.286 |
| 0299 | 0.122 | 0.257 | 1182 | 0.126 | 0.743 | 2157 | 0.043 | 0.743 | 2857 | 0.034 | 0.843 |
| 0309 | 0.383 | 0.729 | 1184 | 0.015 | 0.814 | 2159 | 0.228 | 0.7 | 2859 | 0.111 | 0.3 |
| 0317 | 0.082 | 0.214 | 1189 | 0.097 | 0.757 | 2171 | 0.2 | 0.7 | 2860 | 0.075 | 0.214 |
| 0331 | 0.2 | 0.286 | 1192 | 0.115 | 0.3 | 2176 | 0.036 | 0.771 | 2891 | 0.18 | 0.286 |
| 0334 | 0.155 | 0.757 | 1204 | 0.19 | 0.7 | 2177 | 0.335 | 0.714 | 2916 | 0.101 | 0.257 |
| 0343 | 0.119 | 0.743 | 1207 | 0.016 | 0.829 | 2192 | 0.285 | 0.729 | 2920 | 0.084 | 0.229 |
| 0359 | 0.081 | 0.257 | 1213 | 0.008 | 0.086 | 2202 | 0.173 | 0.3 | 2922 | 0.126 | 0.186 |
| 0373 | 0.209 | 0.714 | 1222 | 0.068 | 0.214 | 2204 | 0.122 | 0.243 | 2924 | 0.034 | 0.829 |
| 0393 | 0.175 | 0.271 | 1237 | 0.059 | 0.186 | 2205 | 0.154 | 0.743 | 2928 | 0.268 | 0.7 |
| 0394 | 0.041 | 0.157 | 1241 | 0.22 | 0.3 | 2217 | 0.195 | 0.286 | 2930 | 0.247 | 0.257 |
| 0395 | 0.096 | 0.729 | 1242 | 0.347 | 0.257 | 2226 | 0.12 | 0.729 | 2933 | 0.081 | 0.229 |
| 0398 | 0.32 | 0.714 | 1268 | 0.06 | 0.757 | 2227 | 0.024 | 0.157 | 2956 | 0.113 | 0.271 |

TABLE 21-continued

List of 467 lncRNAs which are differentially expressed and/or have an AUC > 0.7 or < 0.3 between the low LVEF group (LVEF ≤ 45) and the high LVEF group (LVEF > 45)

| lncRNA (SEQ ID NO:) | p-value | AUC | lncRNA (SEQ ID NO:) | p-value | AUC | lncRNA (SEQ ID NO:) | p-value | AUC | lncRNA (SEQ ID NO:) | p-value | AUC |
| --- | --- | --- | --- | --- | --- | --- | --- | --- | --- | --- | --- |
| 0405 | 0.168 | 0.286 | 1270 | 0.121 | 0.257 | 2234 | 0.16 | 0.257 | 2957 | 0.091 | 0.286 |
| 0412 | 0.522 | 0.229 | 1273 | 0.147 | 0.257 | 2235 | 0.065 | 0.214 | 2959 | 0.885 | 0.7 |
| 0425 | 0.284 | 0.714 | 1291 | 0.067 | 0.257 | 2244 | 0.63 | 0.7 | 2961 | 0.014 | 0.186 |
| 0426 | 0.119 | 0.7 | 1300 | 0.097 | 0.8 | 2252 | 0.006 | 0.9 | 2963 | 0.128 | 0.714 |
| 0427 | 0.128 | 0.757 | 1304 | 0.216 | 0.714 | 2264 | 0.206 | 0.3 | 2967 | 0.134 | 0.257 |
| 0434 | 0.381 | 0.7 | 1310 | 0.022 | 0.157 | 2268 | 0.013 | 0.086 | 2972 | 0.378 | 0.743 |
| 0440 | 0.15 | 0.714 | 1321 | 0.081 | 0.257 | 2270 | 0.146 | 0.257 | 2974 | 0.169 | 0.743 |
| 0441 | 0.122 | 0.243 | 1328 | 0.129 | 0.3 | 2273 | 0.026 | 0.857 | 2977 | 0.043 | 0.129 |
| 0467 | 0.201 | 0.7 | 1336 | 0.047 | 0.743 | 2279 | 0.121 | 0.3 | 2978 | 0.261 | 0.271 |
| 0474 | 0.252 | 0.757 | 1343 | 0.132 | 0.714 | 2281 | 0.108 | 0.714 | 2986 | 0.062 | 0.229 |
| 0479 | 0.073 | 0.214 | 1345 | 0.188 | 0.286 | 2289 | 0.145 | 0.7 | 2988 | 0.141 | 0.257 |
| 0482 | 0.231 | 0.714 | 1350 | 0.118 | 0.3 | 2294 | 0.082 | 0.729 | 2993 | 0.026 | 0.171 |
| 0490 | 0.13 | 0.714 | 1354 | 0.181 | 0.714 | 2297 | 0.619 | 0.714 | 2995 | 0.152 | 0.286 |
| 0493 | 0.142 | 0.714 | 1369 | 0.141 | 0.271 | 2305 | 0.082 | 0.757 | 2996 | 0.197 | 0.3 |
| 0494 | 0.095 | 0.743 | 1378 | 0.28 | 0.286 | 2309 | 0.117 | 0.757 | 2997 | 0.054 | 0.243 |
| 0501 | 0.093 | 0.271 | 1379 | 0.181 | 0.743 | 2318 | 0.066 | 0.714 | 2998 | 0.089 | 0.243 |
| 0502 | 0.178 | 0.7 | 1381 | 0.757 | 0.286 | 2319 | 0.264 | 0.3 | 3009 | 0.224 | 0.3 |
| 0510 | 0.108 | 0.3 | 1384 | 0.095 | 0.271 | 2321 | 0.021 | 0.771 | 3017 | 0.168 | 0.271 |
| 0515 | 0.085 | 0.229 | 1398 | 0.468 | 0.3 | 2326 | 0.126 | 0.743 | 3027 | 0.389 | 0.3 |
| 0534 | 0.43 | 0.743 | 1403 | 0.096 | 0.757 | 2334 | 0.285 | 0.257 | 3030 | 0.165 | 0.271 |
| 0536 | 0.074 | 0.743 | 1406 | 0.108 | 0.271 | 2336 | 0.085 | 0.757 | 3040 | 0.036 | 0.8 |
| 0538 | 0.259 | 0.7 | 1409 | 0.218 | 0.229 | 2339 | 0.15 | 0.729 | 3042 | 0.214 | 0.186 |
| 0540 | 0.038 | 0.2 | 1411 | 0.091 | 0.757 | 2347 | 0.043 | 0.743 | 3054 | 0.188 | 0.243 |
| 0542 | 0.021 | 0.857 | 1426 | 0.165 | 0.714 | 2355 | 0.207 | 0.3 | 3058 | 0.091 | 0.757 |
| 0547 | 0.12 | 0.729 | 1433 | 0.006 | 0.129 | 2375 | 0.349 | 0.3 | 3064 | 0.171 | 0.714 |
| 0549 | 0.104 | 0.743 | 1439 | 0.056 | 0.229 | 2379 | 0.036 | 0.857 | 3067 | 0.148 | 0.286 |
| 0550 | 0.137 | 0.743 | 1440 | 0.198 | 0.3 | 2382 | 0.072 | 0.229 | 3069 | 0.291 | 0.3 |
| 0552 | 0.151 | 0.743 | 1445 | 0.229 | 0.7 | 2386 | 0.172 | 0.257 | 3077 | 0.212 | 0.3 |
| 0571 | 0.415 | 0.271 | 1458 | 0.149 | 0.771 | 2388 | 0.289 | 0.271 | 3078 | 0.057 | 0.786 |
| 0574 | 0.168 | 0.3 | 1474 | 0.092 | 0.257 | 2389 | 0.015 | 0.171 | 3079 | 0.031 | 0.186 |
| 0581 | 0.081 | 0.729 | 1478 | 0.27 | 0.3 | 2392 | 0.189 | 0.243 | 3083 | 0.171 | 0.286 |
| 0596 | 0.208 | 0.229 | 1490 | 0.223 | 0.3 | 2393 | 0.124 | 0.257 | 3092 | 0.283 | 0.243 |
| 0598 | 0.352 | 0.3 | 1491 | 0.195 | 0.3 | 2395 | 0.068 | 0.714 | 3102 | 0.209 | 0.3 |
| 0603 | 0.238 | 0.286 | 1493 | 0.042 | 0.2 | 2402 | 0.438 | 0.714 | 3111 | 0.303 | 0.286 |
| 0615 | 0.231 | 0.257 | 1495 | 0.185 | 0.3 | 2405 | 0.001 | 0.929 | 3119 | 0.042 | 0.229 |
| 0617 | 0.174 | 0.714 | 1504 | 0.211 | 0.271 | 2406 | 0.049 | 0.186 | 3124 | 0.04 | 0.829 |
| 0620 | 0.06 | 0.257 | 1508 | 0.115 | 0.157 | 2408 | 0.22 | 0.257 | 3126 | 0.158 | 0.714 |
| 0635 | 0.089 | 0.214 | 1515 | 0.251 | 0.257 | 2409 | 0.045 | 0.829 | 3129 | 0.152 | 0.271 |
| 0636 | 0.148 | 0.743 | 1516 | 0.21 | 0.729 | 2420 | 0.102 | 0.257 | 3140 | 0.185 | 0.271 |
| 0659 | 0.005 | 0.914 | 1536 | 0.066 | 0.229 | 2420 | 0.08 | 0.743 | 3141 | 0.036 | 0.214 |
| 0677 | 0.081 | 0.757 | 1537 | 0.127 | 0.7 | 2427 | 0.038 | 0.8 | 3142 | 0.015 | 0.157 |
| 0698 | 0.048 | 0.771 | 1539 | 0.168 | 0.729 | 2429 | 0.082 | 0.186 | 3144 | 0.145 | 0.243 |
| 0702 | 0.074 | 0.757 | 1548 | 0.183 | 0.3 | 2433 | 0.105 | 0.257 | 3147 | 0.037 | 0.171 |
| 0707 | 0.092 | 0.757 | 1558 | 0.079 | 0.229 | 2437 | 0.058 | 0.757 | 3148 | 0.19 | 0.714 |
| 0709 | 0.137 | 0.286 | 1570 | 0.014 | 0.171 | 2440 | 0.157 | 0.257 | 3154 | 0.302 | 0.714 |
| 0716 | 0.017 | 0.186 | 1573 | 0.107 | 0.271 | 2450 | 0.101 | 0.229 | 3156 | 0.09 | 0.257 |
| 0724 | 0.048 | 0.814 | 1576 | 0.044 | 0.786 | 2454 | 0.058 | 0.771 | 3157 | 0.092 | 0.243 |
| 0731 | 0.108 | 0.2 | 1587 | 0.009 | 0.9 | 2459 | 0.03 | 0.8 | 3169 | 0.005 | 0.914 |
| 0748 | 0.11 | 0.286 | 1591 | 0.192 | 0.714 | 2472 | 0.2 | 0.271 | 3170 | 0.428 | 0.286 |
| 0750 | 0.009 | 0.143 | 1592 | 0.24 | 0.743 | 2475 | 0.303 | 0.286 | 3176 | 0.032 | 0.771 |
| 0751 | 0.102 | 0.2 | 1593 | 0.032 | 0.814 | 2487 | 0.115 | 0.786 | 3178 | 0.017 | 0.2 |
| 0766 | 0.16 | 0.714 | 1594 | 0.147 | 0.286 | 2492 | 0.147 | 0.3 | 3179 | 0.235 | 0.3 |
| 0772 | 0.134 | 0.286 | 1599 | 0.101 | 0.729 | 2497 | 0.149 | 0.729 | 3182 | 0.064 | 0.786 |
| 0779 | 0.716 | 0.714 | 1609 | 0.059 | 0.186 | 2501 | 0.138 | 0.743 | 3183 | 0.059 | 0.743 |
| 0805 | 0.504 | 0.714 | 1623 | 0.153 | 0.271 | 2503 | 0.122 | 0.7 | 3186 | 0.092 | 0.2 |
| 0806 | 0.16 | 0.3 | 1638 | 0.1 | 0.3 | 2511 | 0.314 | 0.286 | 3207 | 0.123 | 0.257 |
| 0833 | 0.067 | 0.214 | 1647 | 0.181 | 0.7 | 2513 | 0.048 | 0.857 | 3208 | 0.138 | 0.3 |
| 0839 | 0.178 | 0.714 | 1649 | 0.054 | 0.229 | 2518 | 0.075 | 0.243 | 3209 | 0.11 | 0.257 |
| 0851 | 0.103 | 0.743 | 1656 | 0.102 | 0.271 | 2521 | 0.153 | 0.286 | 3210 | 0.055 | 0.757 |
| 0852 | 0.122 | 0.243 | 1660 | 0.067 | 0.786 | 2529 | 0.099 | 0.271 | 3213 | 0.052 | 0.157 |
| 0862 | 0.023 | 0.843 | 1671 | 0.421 | 0.257 | 2532 | 0.164 | 0.714 | 3221 | 0.207 | 0.3 |
| 0864 | 0.174 | 0.257 | 1678 | 0.148 | 0.286 | 2533 | 0.02 | 0.157 | 3222 | 0.092 | 0.229 |
| 0866 | 0.095 | 0.7 | 1691 | 0.223 | 0.7 | 2552 | 0.107 | 0.214 | 3228 | 0.265 | 0.3 |
| 0874 | 0.152 | 0.7 | 1692 | 0.207 | 0.7 | 2555 | 0.504 | 0.3 | | | |

Correlation Between LncRNA and Left Ventricular Ejection Fraction

LncRNAs expression level can be considered as a continuous value. Spearman correlation factor is calculated to measure the correlation between LVEF value at one month and expression level. When a threshold of (+ or −) 0.45 for correlation factor is applied, the expression of 159 lncRNAs is positively or negatively correlated with prediction of LVEF at 1 month. Among these 159 lncRNAs, 94 have a positive correlation factor whereas 65 have a negative correlation factor (Table 22).

TABLE 22

List of 159 lncRNAs with spearman correlation factor higher than 0.45 (absolute value)

| LncRNA (SEQ ID NO:) | correlation | LncRNA (SEQ ID NO:) | correlation | LncRNA (SEQ ID NO:) | correlation | LncRNA (SEQ ID NO:) | correlation |
|---|---|---|---|---|---|---|---|
| 0002 | −0.522 | 0958 | −0.482 | 1899 | 0.564 | 2647 | 0.452 |
| 0005 | −0.477 | 0966 | −0.545 | 1935 | 0.55 | 2660 | 0.483 |
| 0008 | 0.565 | 0980 | 0.456 | 1962 | 0.473 | 2692 | 0.603 |
| 0068 | 0.461 | 0986 | −0.651 | 2021 | 0.49 | 2740 | 0.52 |
| 0104 | 0.454 | 1055 | −0.455 | 2031 | 0.475 | 2742 | −0.475 |
| 0108 | −0.581 | 1057 | 0.585 | 2062 | 0.546 | 2745 | −0.531 |
| 0111 | 0.67 | 1065 | 0.667 | 2082 | −0.542 | 2767 | −0.484 |
| 0134 | 0.729 | 1075 | 0.474 | 2094 | 0.648 | 2785 | 0.457 |
| 0139 | −0.489 | 1093 | 0.461 | 2161 | 0.565 | 2827 | −0.493 |
| 0155 | −0.511 | 1207 | −0.591 | 2176 | −0.686 | 2843 | 0.473 |
| 0168 | 0.522 | 1208 | 0.543 | 2177 | −0.467 | 2857 | −0.459 |
| 0210 | −0.458 | 1213 | 0.541 | 2192 | −0.554 | 2860 | 0.572 |
| 0219 | −0.476 | 1222 | 0.466 | 2204 | 0.461 | 2865 | −0.517 |
| 0246 | 0.523 | 1270 | 0.516 | 2205 | −0.566 | 2886 | −0.493 |
| 0292 | 0.585 | 1299 | −0.479 | 2225 | 0.569 | 2920 | 0.453 |
| 0343 | −0.47 | 1343 | −0.593 | 2227 | 0.573 | 2961 | 0.467 |
| 0394 | 0.497 | 1354 | −0.47 | 2230 | 0.569 | 2974 | −0.575 |
| 0443 | −0.573 | 1403 | −0.463 | 2263 | 0.532 | 2978 | 0.555 |
| 0462 | 0.452 | 1412 | −0.524 | 2303 | 0.618 | 2993 | 0.453 |
| 0487 | 0.456 | 1433 | 0.564 | 2309 | −0.527 | 3006 | −0.476 |
| 0510 | 0.504 | 1440 | 0.575 | 2326 | −0.481 | 3029 | 0.606 |
| 0536 | −0.481 | 1465 | 0.632 | 2346 | −0.533 | 3046 | −0.483 |
| 0596 | 0.544 | 1477 | 0.553 | 2390 | 0.521 | 3058 | −0.474 |
| 0624 | 0.493 | 1508 | 0.667 | 2392 | 0.567 | 3079 | 0.487 |
| 0635 | 0.503 | 1558 | 0.57 | 2405 | −0.499 | 3086 | 0.468 |
| 0639 | 0.482 | 1560 | 0.567 | 2406 | 0.617 | 3108 | 0.576 |
| 0659 | −0.486 | 1573 | 0.525 | 2444 | 0.472 | 3124 | −0.487 |
| 0677 | −0.519 | 1587 | −0.465 | 2450 | 0.451 | 3128 | 0.577 |
| 0681 | −0.547 | 1594 | 0.499 | 2459 | −0.656 | 3141 | 0.527 |
| 0698 | −0.666 | 1598 | −0.496 | 2487 | −0.497 | 3142 | 0.604 |
| 0701 | 0.455 | 1660 | −0.47 | 2492 | 0.557 | 3156 | 0.517 |
| 0716 | 0.529 | 1678 | 0.507 | 2497 | −0.496 | 3169 | −0.675 |
| 0731 | 0.518 | 1682 | 0.451 | 2513 | −0.525 | 3176 | −0.457 |
| 0766 | −0.476 | 1687 | −0.49 | 2542 | −0.536 | 3178 | 0.46 |
| 0772 | 0.524 | 1698 | −0.53 | 2576 | 0.542 | 3183 | −0.582 |
| 0833 | 0.471 | 1723 | −0.581 | 2586 | 0.524 | 3200 | 0.543 |
| 0841 | −0.527 | 1740 | −0.533 | 2611 | 0.452 | 3207 | 0.451 |
| 0884 | 0.472 | 1794 | 0.517 | 2636 | 0.493 | 3209 | 0.533 |
| 0914 | 0.454 | 1852 | −0.541 | 2642 | 0.514 | 3213 | 0.665 |
| 0946 | −0.451 | 1854 | −0.534 | 2645 | 0.471 | | |

Comparison of the Total RNA-Seq and FiMICS Analysis

Figure 6:
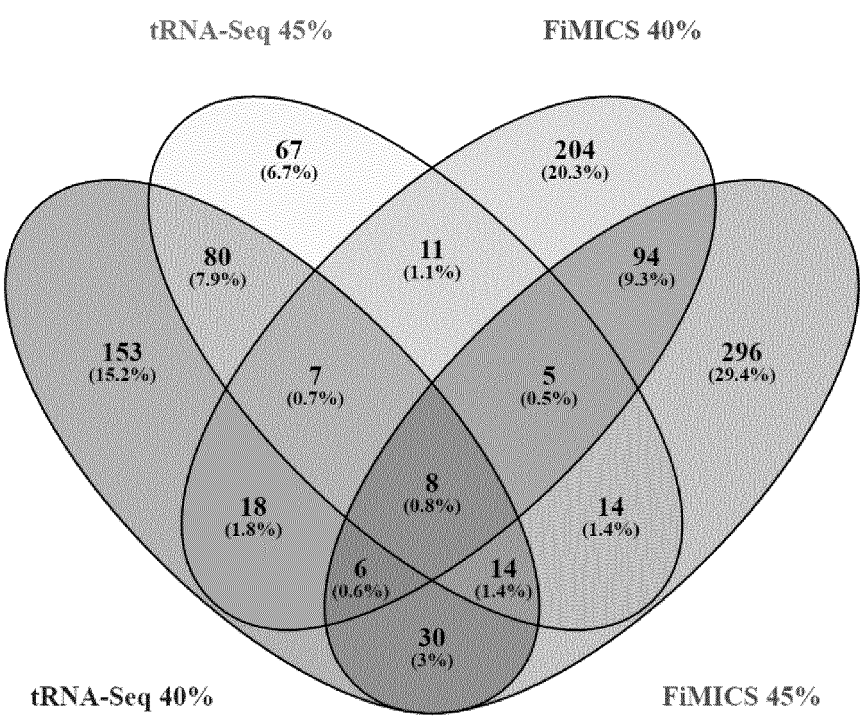
FIG. 6 shows Venn diagram of the significantly expressed lncRNAs from analysis of RNASeq and FiMICS data generated in serum samples collected at D3 of patients with AMI for the prediction of ventricular remodeling measured by the Echocardiography at month 1 post PCI. Low LVEF corresponding to the ventricular remodeling is grouped using two thresholds: either LVEF<40% or 45%.

Detection level and performance of the lncRNAs can vary in function of the method and number of samples used. FIG. 6 represent the Venn diagram for each analysis using a threshold of LVEF at 40% and 45% for total RNA-Sequencing and FiMICS test. For the comparison of the 4 conditions, 8 lncRNAs are common to all conditions (SEQ ID NO: 1204, SEQ ID NO: 2454, SEQ ID NO: 0334, SEQ ID NO: 1403, SEQ ID NO: 1089, SEQ ID NO: 2692, SEQ ID NO: 2273, and SEQ ID NO: 0502).

An example of probes sequences designed on FiMICS for the first lncRNA (SEQ ID NO: 1204) includes the below sequences;

| FIMICS Probe sequence | lncRNA |
|---|---|
| GTTCTACTCAAAGGGTCAGTTTAGGGCATAATTAAAGTCAAT TACTTTCTGAAAGGCCATCAGGACAACTGTTAGAGAAAATGA TAGCAGCCCCGCACTTGCTGTAGGAATTATTAGCTT (SEQ ID NO: 3247) | SEQ NO: ID 1204 |
| CAGGACAACTGTTAGAGAAAATGATAGCAGCCCCGCACTTGC TGTAGGAATTATTAGCTTGTCAGCCTCCAGGCTTATGGAGAC AAAGGATCAAAAAGTTAGAGAGATCCAGGTGTTCAC (SEQ ID NO: 3248) | SEQ NO: ID 1204 |
| GTCAGCCTCCAGGCTTATGGAGACAAAGGATCAAAAAGTTAG AGAGATCCAGGTGTTCACCTATTTGTTCACTAATTCTTTTATT GTGAGTGTGCATGTGTGTGGGTGGGTGTGACATTT (SEQ ID NO: 3249) | SEQ NO: ID 1204 |
| CTATTTGTTCACTAATTCTTTTATTGTGAGTGTGCATGTGTGTG GGTGGGTGTGACATTTATTATGAACCAGAGGGCAGGAGCCAG TGACACAGTGGTCAGAGAATAATCATATTCCCT (SEQ ID NO: 3250) | SEQ NO: ID 1204 |
| ATTATGAACCAGAGGGCAGGAGCCAGTGACACAGTGGTGCA GAGAATAATCATATTCCCTGCCTTCCTGGGGTCATACAGCTTG GTGGAGGACACAGATGTGAATTCGGTAATCACTCCA (SEQ ID NO: 3251) | SEQ NO: ID 1204 |
| GCCTTCCTGGGGTCATACAGCTTGGTGGAGGACACAGATGTG AATTCGGTAATCACTCCAATAAATATTCTCCTACAGATGAAG AAAGATGATACGATGTGATGGACAACAGAGACTTAT (SEQ ID NO: 3252) | SEQ NO: ID 1204 |
| ATAAATATTCTCCTACAGATGAAGAAAGATGATACGATGTGA TGGACAACAGAGACTTATATGGTGGGGTCTGGGCTGGTCTTT CTGAAGCTAAGACTGGCAGGATGAGCAGGAGTTTGC (SEQ ID NO: 3253) | SEQ NO: ID 1204 |

| FIMICS Probe sequence | lncRNA |
|---|---|
| ATGGTGGGGTCTGGGCTGGTCTTTCTGAAGCTAAGACTGGCA<br>GGATGAGCAGGAGTTTGCCAGACAAAGAGGAGTGGAGTTGT<br>TTTCCAAACACATCTCAGCACAAAGTGTTGTCTTTGC<br>(SEQ ID NO: 3254) | SEQ<br>NO:<br>ID<br>1204 |
| CAGACAAAGAGGAGTGGAGTTGTTTTCCAAACACATCTCAGC<br>ACAAAGTGTTGTCTTTGCTGGGAGCTGAAAAAAGATAGTGTG<br>GGCAGAGACCATTAGGTGAGACGCTTGATATGAGAT<br>(SEQ ID NO: 3255) | SEQ<br>NO:<br>ID<br>1204 |
| TGGGAGCTGAAAAAAGATAGTGTGGGCAGAGACCATTAGGT<br>GAGACGCTTGATATGAGATACAACCTCAACAGGTGGAAGAA<br>GATCATGAGAGATGAAGAGAGGAATATAGTACAGCAGA<br>(SEQ ID NO: 3256) | SEQ<br>NO:<br>ID<br>1204 |
| ACAACCTCAACAGGTGGAAGAAGATCATGAGAGATGAAGAG<br>AGGAATATAGTACAGCAGAGAGGACACAGAAGCTGACGTCA<br>GGGTGTCTCAGTTTGAAACCAGTGGCCACCCTGTTCCT<br>(SEQ ID NO: 3257) | SEQ<br>NO:<br>ID<br>1204 |
| GAGGACACAGAAGCTGACGTCAGGGTGTCTCAGTTTGAAACC<br>AGTGGCCACCCTGTTCCTCTCCCATGTGGTCCCATCATGGGCC<br>TCTAGGGTCTGGGATAAGAGGTTAATGAATATCTC<br>(SEQ ID NO: 3258) | SEQ<br>NO:<br>ID<br>1204 |
| CTCCCATGTGGTCCCATCATGGGCCTCTAGGGTCTGGGATAA<br>GAGGTTAATGAATATCTCATACCCTAAGCAGGGGTGGTCCCT<br>GCACTTTAGCAAAAAGTTAAGGAACTAGGGAAAAGA<br>(SEQ ID NO: 3259) | SEQ<br>NO:<br>ID<br>1204 |
| ATACCCTAAGCAGGGGTGGTCCCTGCACTTTAGCAAAAAGTT<br>AAGGAACTAGGGAAAAGAGATGGAAATAATAAAGAGATGGG<br>ACAAAGACTTTGAAGACCAAAGCCCCTGGGCTATTCT<br>(SEQ ID NO: 3260) | SEQ<br>NO:<br>ID<br>1204 |
| GATGGAAATAATAAAGAGATGGGACAAAGACTTTGAAGACC<br>AAAGCCCCTGGGCTATTCTCTTTTTTAAATTTTTTTATTTAAAT<br>TTTCATTTATTTTTATCAAGATAGGGTCTCACTAT<br>(SEQ ID NO: 3261) | SEQ<br>NO:<br>ID<br>1204 |
| CTTTTTTAAATTTTTTTATTTAAATTTTCATTTATTTTTATCAA<br>GATAGGGTCTCACTATGTTGCCCAGGTTGGTCTCAAACTTTTG<br>GCCTAAAGCAATCCTCCCACCTTGGCCTCCCAA<br>(SEQ ID NO: 3262) | SEQ<br>NO:<br>ID<br>1204 |
| GTTGCCCAGGTTGGTCTCAAACTTTTGGCCTAAAGCAATCCTC<br>CCACCTTGGCCTCCCAATGTGCTGGGATTACAATGTGAGCCA<br>CCACGTCCAGCCTCCTGGGATATTTCTCAATGAAA<br>(SEQ ID NO: 3263) | SEQ<br>NO:<br>ID<br>1204 |
| TGTGCTGGGATTACAATGTGAGCCACCACGTCCAGCCTCCTG<br>GGATATTTCTCAATGAAACATTGGATGCCAAGATTGGTTTTGT<br>GCCACATGCCAATTTCACAGAAGCCAGTCTATGAG<br>(SEQ ID NO: 3264) | SEQ<br>NO:<br>ID<br>1204 |
| CATTGGATGCCAAGATTGGTTTTGTGCCACATGCCAATTTCAC<br>AGAAGCCAGTCTATGAGCCACCAGCTCTACTCAGCAATTACA<br>GTTTCTGGAACTTTGGCTAAATTCCTGTAGATGCA<br>(SEQ ID NO: 3265) | SEQ<br>NO:<br>ID<br>1204 |
| CCACCAGCTCTACTCAGCAATTACAGTTTCTGGAACTTTGGCT<br>AAATTCCTGTAGATGCACCACTGCTTGTGGCCTGACTCTTTGC<br>CACCCAAGTGCGCTCAGCCTCCCCTGGGGAGTCT<br>(SEQ ID NO: 3266) | SEQ<br>NO:<br>ID<br>1204 |
| CCACTGCTTGTGGCCTGACTCTTTGCCACCCAAGTGCGCTCAG<br>CCTCCCCTGGGGAGTCTGCCAGGCTTGCATGGCTCCCACTGC<br>ACTTGCTGTGCTGGGACCGAAAACAGTTTTTGTGC<br>(SEQ ID NO: 3267) | SEQ<br>NO:<br>ID<br>1204 |
| GCCAGGCTTGCATGGCTCCCACTGCACTTGCTGTGCTGGGAC<br>CGAAAACAGTTTTTGTGCCCCTAGCTTAACTCCACTGGATTCA<br>TAGAGGCTTTGGCCTCCTCAATGGCTGTCCTGGGA<br>(SEQ ID NO: 3268) | SEQ<br>NO:<br>ID<br>1204 |
| CCCTAGCTTAACTCCACTGGATTCATAGAGGCTTTGGCCTCCT<br>CAATGGCTGTCCTGGGACAGGGAGGCTGGTTAGCACAATTAA<br>CACAACCTGGTCATGCAAGGCATTGATGGTCCGTA<br>(SEQ ID NO: 3269) | SEQ<br>NO:<br>ID<br>1204 |
| CAGGGAGGCTGGTTAGCACAATTAACACAACCTGGTCATGCA<br>AGGCATTGATGGTCCGTAACATGAACTTTGACCAGTAGGAGA<br>CAGAGAATGGAAAAAAGCCAGCAGATAAATCATCTG<br>(SEQ ID NO: 3270) | SEQ<br>NO:<br>ID<br>1204 |
| ACATGAACTTTGACCAGTAGGAGACAGAGAATGGAAAAAAG<br>CCAGCAGATAAATCATCTGGCCTTCCTCCCCTATGACAGACT<br>GTTCTGAGCCACAGTGTTTCACATGTCTTCCTGGAGA<br>(SEQ ID NO: 3271) | SEQ<br>NO:<br>ID<br>1204 |
| GCCTTCCTCCCCTATGACAGACTGTTCTGAGCCACAGTGTTTC<br>ACATGTCTTCCTGGAGATGTCCCACATGACTTGAGCAACCAG<br>CTGGAGCTCTGGAGAAACTGTGGCCATCCTGGTAA<br>(SEQ ID NO: 3272) | SEQ<br>NO:<br>ID<br>1204 |
| TGTCCCACATGACTTGAGCAACCAGCTGGAGCTCTGGAGAAA<br>CTGTGGCCATCCTGGTAACATATGACCTTGTATTTGCTTTCTC<br>TCCTTCCTGCTTTATTTCCCTATGTCCCTTACTTT<br>(SEQ ID NO: 3273) | SEQ<br>NO:<br>ID<br>1204 |
| CTGTGGCCATCCTGGTAACATATGACCTTGTATTTGCTTTCTC<br>TCCTTCCTGCTTTATTTCCCTATGTCCCTTACTTTGGTTGTTGG<br>GATTGCACCTCCCAATAAAGCATTAGCATGTCC<br>(SEQ ID NO: 3274) | SEQ<br>NO:<br>ID<br>1204 |

Example 5: LncRNA Detection in PAXgene Samples Using a mRNA-Seq Protocol

Material and Methods:

Paxgene samples collected at discharge of patient between D3 and D5 from 57 patients with AMI from the MitoCare cohort are used for lncRNA profiling. Mitocare is a multicenter, randomized, double-blind, placebo controlled study. The study population includes AMI patients undergoing PCI, older than 18 years. The primary endpoint is the level of left ventricular ejection fraction (LVEF) less than 40% at 1 month. Demographics data are presented in Table 23.

TABLE 23

Demographic data of patients used from Mitocare study

| | Group 1 | Group 2 | Group 3 |
|---|---|---|---|
| EF | <40 | 41-50 | >50 |
| Nb | 8 | 20 | 29 |
| Age | 68.9 | 60.5 | 60.0 |
| Male | 88% | 95% | 81% |
| BMI | 27.0 | 28.1 | 26.6 |
| Systolic Blood Pressure | 103.0 | 119.4 | 116.9 |
| Diastolic Blood Pressure | 66.0 | 71.9 | 69.6 |
| Heart Rate | 82.3 | 72.9 | 66.9 |

RNA extraction, preparation of sequencing libraires and sequencing are performed as described in Example 3.

Results:

Comparison Between Low LVEF (LVEF≤40) and High LVEF (LVEF>40)

In this analysis, the 57 samples AMI were grouped into 2 groups using the threshold of 40% LVEF: low LVEF (LVEF≤40) and high LVEF (LVEF>40). The volcano plot showed the differential expression of lncRNA. 102 lncRNA are differentially expressed and among them, 19 lncRNA have a fold change>2 or <0.5, which are shown in Table 24. 171 lncRNAs with P<0.05 and/or individual AUC>0.7 or <0.3 are listed in Table 25.

TABLE 24

List of 19 lncRNAs which are differentially expressed with a fold change >2 or <0.5 between the low LVEF group (LVEF ≤ 40) and the high LVEF group (LVEF > 40)

| lncRNA | P-value | Fold change | Individual AUC |
|---|---|---|---|
| SEQ ID NO: 0822 | 0.0003 | 0.119 | 0.717 |
| SEQ ID NO: 1170 | 0.0012 | 0.446 | 0.744 |
| SEQ ID NO: 1755 | 0.0014 | 0.434 | 0.75 |
| SEQ ID NO: 0058 | 0.0024 | 0.244 | 0.709 |
| SEQ ID NO: 2007 | 0.0027 | 0.289 | 0.744 |
| SEQ ID NO: 0430 | 0.0039 | 0.394 | 0.717 |
| SEQ ID NO: 0110 | 0.0053 | 0.33 | 0.745 |
| SEQ ID NO: 1331 | 0.0071 | 0.202 | 0.712 |

TABLE 24-continued

List of 19 lncRNAs which are differentially expressed with a fold change >2 or <0.5 between the low LVEF group (LVEF ≤ 40) and the high LVEF group (LVEF > 40)

| lncRNA | P-value | Fold change | Individual AUC |
|---|---|---|---|
| SEQ ID NO: 0388 | 0.0104 | 0.294 | 0.699 |
| SEQ ID NO: 0585 | 0.0156 | 2.091 | 0.194 |
| SEQ ID NO: 0117 | 0.0174 | 0.356 | 0.673 |
| SEQ ID NO: 0415 | 0.0204 | 0.407 | 0.653 |
| SEQ ID NO: 1263 | 0.0223 | 0.471 | 0.672 |
| SEQ ID NO: 0383 | 0.0269 | 0.38 | 0.708 |
| SEQ ID NO: 0187 | 0.0281 | 0.436 | 0.741 |
| SEQ ID NO: 0611 | 0.0310 | 0.355 | 0.656 |
| SEQ ID NO: 2446 | 0.0364 | 0.363 | 0.663 |
| SEQ ID NO: 0548 | 0.0389 | 0.488 | 0.592 |
| SEQ ID NO: 0074 | 0.0461 | 12.549 | 0.221 |

TABLE 25

List of 171 lncRNA, which are differentially expressed and/or have an AUC > 0.7 or < 0.3 between the low LVEF group (LVEF ≤ 40) and the high LVEF group (LVEF > 40)

| LncRNA (SEQ ID NO:) | P-value | AUC | LncRNA (SEQ ID NO:) | P-value | AUC | LncRNA (SEQ ID NO:) | P-value | AUC | LncRNA (SEQ ID NO:) | P-value | AUC |
|---|---|---|---|---|---|---|---|---|---|---|---|
| 0007 | 0.0583 | 0.268 | 0690 | 0.0004 | 0.23 | 1483 | 0.0008 | 0.176 | 2487 | 0.036 | 0.712 |
| 0016 | 0.0542 | 0.263 | 0720 | 0.1176 | 0.73 | 1507 | 0.0098 | 0.293 | 2490 | 0.0171 | 0.268 |
| 0058 | 0.0024 | 0.709 | 0749 | 0.0645 | 0.263 | 1510 | 0.0003 | 0.765 | 2506 | 0.4184 | 0.704 |
| 0069 | 0.0124 | 0.196 | 0756 | 0.0586 | 0.273 | 1511 | 0.0166 | 0.212 | 2522 | 0.0929 | 0.281 |
| 0074 | 0.0461 | 0.221 | 0784 | 0.1568 | 0.283 | 1519 | 0.0066 | 0.681 | 2540 | 0.0604 | 0.27 |
| 0110 | 0.0053 | 0.745 | 0802 | 0.0345 | 0.745 | 1531 | 0.0143 | 0.694 | 2563 | 0.0566 | 0.217 |
| 0113 | 0.0656 | 0.26 | 0803 | 0.0922 | 0.288 | 1533 | 0.0079 | 0.699 | 2571 | 0.0761 | 0.189 |
| 0114 | 0.0453 | 0.661 | 0807 | 0.0841 | 0.281 | 1536 | 0.011 | 0.196 | 2579 | 0.0415 | 0.263 |
| 0117 | 0.0174 | 0.673 | 0816 | 0.0431 | 0.633 | 1591 | 0.0256 | 0.661 | 2588 | 0.0888 | 0.296 |
| 0163 | 0.0042 | 0.158 | 0822 | 0.0003 | 0.717 | 1632 | 0.0308 | 0.283 | 2647 | 0.0615 | 0.283 |
| 0169 | 0.0956 | 0.296 | 0845 | 0.0437 | 0.671 | 1638 | 0.0316 | 0.24 | 2651 | 0.1479 | 0.286 |
| 0187 | 0.0281 | 0.741 | 0914 | 0.0473 | 0.635 | 1669 | 0.0466 | 0.247 | 2672 | 0.0525 | 0.255 |
| 0211 | 0.107 | 0.276 | 0957 | 0.0172 | 0.783 | 1705 | 0.1096 | 0.288 | 2675 | 0.0735 | 0.286 |
| 0240 | 0.0145 | 0.293 | 0968 | 0.0541 | 0.27 | 1755 | 0.0014 | 0.75 | 2692 | 0.0639 | 0.298 |
| 0244 | 0.0702 | 0.291 | 0982 | 0.0477 | 0.607 | 1777 | 0.0585 | 0.255 | 2697 | 0.0147 | 0.237 |
| 0246 | 0.1547 | 0.758 | 0997 | 0.0532 | 0.199 | 1795 | 0.0046 | 0.199 | 2701 | 0.0295 | 0.245 |
| 0265 | 0.2273 | 0.763 | 1023 | 0.0664 | 0.263 | 1809 | 0.041 | 0.265 | 2720 | 0.0434 | 0.255 |
| 0321 | 0.0044 | 0.727 | 1025 | 0.028 | 0.204 | 1822 | 0.0575 | 0.268 | 2727 | 0.0337 | 0.24 |
| 0329 | 0.0702 | 0.26 | 1036 | 0.0415 | 0.281 | 1826 | 0.101 | 0.298 | 2755 | 0.1095 | 0.709 |
| 0334 | 0.3913 | 0.782 | 1047 | 0.0529 | 0.702 | 1885 | 0.0416 | 0.577 | 2779 | 0.0642 | 0.291 |
| 0336 | 0.1104 | 0.276 | 1065 | 0.008 | 0.255 | 1936 | 0.0348 | 0.263 | 2783 | 0.0001 | 0.839 |
| 0348 | 0.0269 | 0.314 | 1066 | 0.0476 | 0.27 | 1949 | 0.0036 | 0.676 | 2794 | 0.0636 | 0.298 |
| 0359 | 0.0171 | 0.237 | 1110 | 0.0596 | 0.263 | 1973 | 0.0075 | 0.148 | 2803 | 0.1414 | 0.293 |
| 0360 | 0.0816 | 0.263 | 1116 | 0.0118 | 0.23 | 1976 | 0.0367 | 0.643 | 2814 | 0.1279 | 0.298 |
| 0367 | 0.0418 | 0.666 | 1151 | 0.0542 | 0.255 | 2003 | 0.0712 | 0.714 | 2855 | 0.022 | 0.217 |
| 0383 | 0.0269 | 0.708 | 1170 | 0.0012 | 0.744 | 2007 | 0.0027 | 0.744 | 2863 | 0.0823 | 0.298 |
| 0388 | 0.0104 | 0.699 | 1209 | 0.0023 | 0.184 | 2025 | 0.028 | 0.676 | 2878 | 0.0148 | 0.191 |
| 0409 | 0.0056 | 0.73 | 1211 | 0.0298 | 0.758 | 2042 | 0.0214 | 0.704 | 2887 | 0.082 | 0.298 |
| 0415 | 0.0204 | 0.653 | 1252 | 0.0275 | 0.222 | 2057 | 0.025 | 0.245 | 2928 | 0.0927 | 0.286 |
| 0430 | 0.0039 | 0.717 | 1263 | 0.0223 | 0.672 | 2070 | 0.0208 | 0.714 | 2967 | 0.0218 | 0.296 |
| 0435 | 0.0126 | 0.214 | 1265 | 0.1112 | 0.291 | 2084 | 0.0164 | 0.23 | 2992 | 0.0096 | 0.209 |
| 0459 | 0.093 | 0.733 | 1285 | 0.0491 | 0.626 | 2095 | 0.082 | 0.288 | 3011 | 0.0128 | 0.189 |
| 0460 | 0.0418 | 0.676 | 1290 | 0.0851 | 0.288 | 2150 | 0.0561 | 0.224 | 3029 | 0.0721 | 0.268 |
| 0477 | 0.0012 | 0.156 | 1300 | 0.0452 | 0.625 | 2229 | 0.5132 | 0.707 | 3080 | 0.0223 | 0.24 |
| 0493 | 0.0178 | 0.722 | 1319 | 0.0549 | 0.273 | 2254 | 0.0465 | 0.714 | 3118 | 0.0086 | 0.194 |
| 0534 | 0.0453 | 0.656 | 1325 | 0.0718 | 0.288 | 2277 | 0.0804 | 0.276 | 3128 | 0.0276 | 0.224 |
| 0548 | 0.0389 | 0.592 | 1331 | 0.0071 | 0.712 | 2291 | 0.0315 | 0.27 | 3154 | 0.0255 | 0.288 |
| 0559 | 0.0698 | 0.273 | 1386 | 0.0312 | 0.676 | 2325 | 0.0406 | 0.651 | 3160 | 0.02 | 0.247 |
| 0566 | 0.0805 | 0.263 | 1406 | 0.0161 | 0.689 | 2369 | 0.0483 | 0.296 | 3184 | 0.1028 | 0.26 |
| 0585 | 0.0156 | 0.194 | 1421 | 0.1131 | 0.264 | 2371 | 0.3109 | 0.745 | 3186 | 0.0802 | 0.291 |
| 0598 | 0.0505 | 0.263 | 1451 | 0.0196 | 0.709 | 2387 | 0.1645 | 0.296 | 3203 | 0.0226 | 0.235 |
| 0608 | 0.0648 | 0.714 | 1458 | 0.0329 | 0.635 | 2436 | 0.0619 | 0.247 | 3235 | 0.0114 | 0.232 |
| 0611 | 0.031 | 0.656 | 1460 | 0.1292 | 0.298 | 2446 | 0.0364 | 0.663 | | | |

For this classification, the variable selection was performed by using a Random Forest model. A combination of 20 pre-selected lncRNA through a Random Forest Classifier (Table 26) is the best predictive model obtained here. The lncRNAs were selected using a random forest algorithm. The model was produced with Naives Bayes algorithm. This model has an area under the receiver-operating characteristic curve (AUC) of 0.834, an accuracy of 0.895, a sensitivity of 0.918, a specificity of 0.75, a Positive Predictive Value (PPV) of 0.957 and Negative Predictive Value (PNV) of 0.6. The confusion matrix is presented in Table 27.

TABLE 26

List of 20 pre-selected lncRNA through a Random Forest Classifier for the classification low LVEF (LVEF ≤ 40) and high LVEF (LVEF > 40)

| lncRNA | Rank in the model |
|---|---|
| SEQ ID NO: 0190 | 1 |
| SEQ ID NO: 0359 | 2 |
| SEQ ID NO: 0776 | 3 |
| SEQ ID NO: 1421 | 4 |
| SEQ ID NO: 1795 | 5 |
| SEQ ID NO: 0477 | 6 |
| SEQ ID NO: 1511 | 7 |
| SEQ ID NO: 0435 | 8 |
| SEQ ID NO: 1418 | 9 |
| SEQ ID NO: 1025 | 10 |
| SEQ ID NO: 0265 | 11 |
| SEQ ID NO: 1311 | 12 |
| SEQ ID NO: 2540 | 13 |
| SEQ ID NO: 2323 | 14 |
| SEQ ID NO: 3011 | 15 |
| SEQ ID NO: 2447 | 16 |
| SEQ ID NO: 2863 | 17 |
| SEQ ID NO: 2697 | 18 |
| SEQ ID NO: 3128 | 19 |
| SEQ ID NO: 2265 | 20 |

TABLE 27

Confusion matrix of the best model for this classification

| | Low LVEF predicted | High LVEF predicted |
|---|---|---|
| Low LVEF True | 6 | 2 |
| High LVEF True | 4 | 45 |

Comparison Between Low LVEF (LVEF≤45) and High LVEF (LVEF>45)

In this analysis, the 57 samples AMI were grouped into 2 groups using the threshold of 45% LVEF: low LVEF (LVEF≤45) and high LVEF (LVEF>45). The volcano plot showed the differential expression of lncRNA. 110 lncRNA are differentially expressed and among them 11 lncRNA have a fold change>2 or <0.5, which are in Table 28. 112 lncRNAs with P<0.05 and/or individual AUC>0.7 or <0.3 are listed in Table 29.

TABLE 28

List of 11 lncRNAs which are differentially expressed with a fold change >2 or <0.5 between the low LVEF group (LVEF ≤ 40) and the high LVEF group (LVEF > 40)

| lncRNA | P-Value | foldchange | AUC |
|---|---|---|---|
| SEQ ID NO: 1755 | 0.00017 | 0.460 | 0.740 |
| SEQ ID NO: 1331 | 0.00072 | 0.243 | 0.710 |
| SEQ ID NO: 1372 | 0.00560 | 0.437 | 0.695 |
| SEQ ID NO: 1341 | 0.01608 | 0.364 | 0.664 |
| SEQ ID NO: 0173 | 0.02953 | 0.481 | 0.654 |
| SEQ ID NO: 0611 | 0.03193 | 0.434 | 0.645 |
| SEQ ID NO: 1602 | 0.03198 | 2.164 | 0.301 |
| SEQ ID NO: 0442 | 0.04288 | 0.477 | 0.635 |
| SEQ ID NO: 0117 | 0.04364 | 0.494 | 0.607 |
| SEQ ID NO: 0074 | 0.04683 | 7.908 | 0.346 |
| SEQ ID NO: 2168 | 0.04815 | 0.452 | 0.627 |

TABLE 29

List of 112 lncRNAs which are differentially expressed and/or have an AUC > 0.7 or < 0.3 between the low LVEF group (LVEF ≤ 40) and the high LVEF group (LVEF > 40)

| LncRNA (SEQ ID. NO:) | P-Value | AUC | LncRNA (SEQ ID. NO:) | P-Value | AUC | LncRNA (SEQ ID. NO:) | P-Value | AUC | LncRNA (SEQ ID. NO:) | P-Value | AUC |
|---|---|---|---|---|---|---|---|---|---|---|---|
| 0007 | 0.028 | 0.33 | 0627 | 0.015 | 0.70 | 1458 | 0.033 | 0.67 | 2347 | 0.019 | 0.69 |
| 0036 | 0.057 | 0.72 | 0690 | 0.019 | 0.30 | 1475 | 0.012 | 0.70 | 2369 | 0.047 | 0.34 |
| 0064 | 0.031 | 0.65 | 0709 | 0.031 | 0.64 | 1483 | 0.025 | 0.30 | 2426 | 0.030 | 0.62 |
| 0074 | 0.047 | 0.35 | 0720 | 0.008 | 0.71 | 1511 | 0.007 | 0.30 | 2436 | 0.020 | 0.29 |
| 0079 | 0.004 | 0.73 | 0749 | 0.031 | 0.29 | 1518 | 0.023 | 0.31 | 2471 | 0.007 | 0.73 |
| 0117 | 0.044 | 0.61 | 0756 | 0.023 | 0.33 | 1519 | 0.017 | 0.68 | 2502 | 0.033 | 0.33 |
| 0137 | 0.012 | 0.72 | 0762 | 0.021 | 0.31 | 1533 | 0.004 | 0.73 | 2540 | 0.008 | 0.26 |
| 0163 | 0.017 | 0.30 | 0802 | 0.019 | 0.68 | 1536 | 0.026 | 0.32 | 2647 | 0.027 | 0.31 |
| 0169 | 0.024 | 0.29 | 0845 | 0.013 | 0.68 | 1539 | 0.002 | 0.73 | 2684 | 0.028 | 0.27 |
| 0173 | 0.030 | 0.65 | 0914 | 0.039 | 0.62 | 1591 | 0.043 | 0.61 | 2697 | 0.004 | 0.28 |
| 0240 | 0.017 | 0.31 | 1025 | 0.026 | 0.31 | 1596 | 0.044 | 0.63 | 2727 | 0.008 | 0.30 |
| 0265 | 0.024 | 0.73 | 1042 | 0.012 | 0.26 | 1602 | 0.032 | 0.30 | 2783 | 0.018 | 0.68 |
| 0269 | 0.016 | 0.31 | 1047 | 0.044 | 0.66 | 1739 | 0.002 | 0.70 | 2850 | 0.045 | 0.33 |
| 0359 | 0.003 | 0.29 | 1065 | 0.011 | 0.29 | 1755 | 0.000 | 0.74 | 2863 | 0.040 | 0.32 |
| 0376 | 0.013 | 0.29 | 1117 | 0.032 | 0.70 | 1762 | 0.024 | 0.69 | 3011 | 0.007 | 0.25 |
| 0440 | 0.009 | 0.65 | 1123 | 0.028 | 0.32 | 1766 | 0.037 | 0.32 | 3049 | 0.047 | 0.59 |
| 0442 | 0.043 | 0.64 | 1150 | 0.030 | 0.66 | 1795 | 0.026 | 0.34 | 3051 | 0.015 | 0.30 |
| 0446 | 0.049 | 0.32 | 1158 | 0.032 | 0.65 | 1930 | 0.010 | 0.30 | 3069 | 0.040 | 0.61 |
| 0476 | 0.016 | 0.66 | 1211 | 0.027 | 0.64 | 1973 | 0.016 | 0.29 | 3106 | 0.035 | 0.31 |
| 0477 | 0.048 | 0.31 | 1228 | 0.011 | 0.65 | 2003 | 0.025 | 0.68 | 3118 | 0.028 | 0.33 |
| 0493 | 0.020 | 0.65 | 1290 | 0.049 | 0.30 | 2084 | 0.024 | 0.30 | 3128 | 0.007 | 0.28 |

TABLE 29-continued

List of 112 lncRNAs which are differentially expressed and/or have an AUC > 0.7 or < 0.3 between the low LVEF group (LVEF ≤ 40) and the high LVEF group (LVEF > 40)

| LncRNA (SEQ ID. NO:) | P-Value | AUC | LncRNA (SEQ ID. NO:) | P-Value | AUC | LncRNA (SEQ ID. NO:) | P-Value | AUC | LncRNA (SEQ ID. NO:) | P-Value | AUC |
|---|---|---|---|---|---|---|---|---|---|---|---|
| 0534 | 0.040 | 0.65 | 1300 | 0.024 | 0.62 | 2113 | 0.021 | 0.32 | 3137 | 0.042 | 0.62 |
| 0535 | 0.010 | 0.70 | 1331 | 0.001 | 0.71 | 2149 | 0.031 | 0.33 | 3160 | 0.015 | 0.31 |
| 0545 | 0.009 | 0.27 | 1341 | 0.016 | 0.66 | 2168 | 0.048 | 0.63 | 3184 | 0.184 | 0.30 |
| 0559 | 0.017 | 0.30 | 1372 | 0.006 | 0.70 | 2186 | 0.042 | 0.63 | 3186 | 0.035 | 0.30 |
| 0564 | 0.040 | 0.63 | 1403 | 0.010 | 0.66 | 2218 | 0.021 | 0.66 | 3193 | 0.026 | 0.32 |
| 0609 | 0.046 | 0.66 | 1406 | 0.016 | 0.68 | 2254 | 0.033 | 0.67 | 3203 | 0.031 | 0.32 |
| 0611 | 0.032 | 0.65 | 1446 | 0.032 | 0.30 | 2323 | 0.050 | 0.65 | 3235 | 0.027 | 0.31 |

For this classification, the variable selection was performed by using a Random Forest model. A combination of 11 pre-selected lncRNA through a Random Forest Classifier (Table 30) is the best predictive model obtained here. The lncRNAs were selected using a random forest algorithm. This model has an area under the receiver-operating characteristic curve (AUC) of 0.905, an accuracy of 0.807, a sensitivity of 0.927, a specificity of 0.5, a Positive Predictive Value (PPV) of 0.826 and Negative Predictive Value (PNV) of 0.727. The confusion matrix is presented in Table 31.

TABLE 30

List of 11 pre-selected lncRNA through a Random Forest Classifier for the classification low LVEF (LVEF ≤ 45) and high LVEF (LVEF > 45)

| lncRNA | Rank in the model |
|---|---|
| SEQ ID NO: 2540 | 1 |
| SEQ ID NO: 0545 | 2 |
| SEQ ID NO: 1766 | 3 |
| SEQ ID NO: 3011 | 4 |
| SEQ ID NO: 0968 | 5 |
| SEQ ID NO: 2371 | 6 |
| SEQ ID NO: 1533 | 7 |
| SEQ ID NO: 0749 | 8 |
| SEQ ID NO: 0609 | 9 |
| SEQ ID NO: 1446 | 10 |
| SEQ ID NO: 2986 | 11 |

TABLE 31

Confusion matrix of the best model for this classification

| | Low LVEF predicted | High LVEF predicted |
|---|---|---|
| Low LVEF True | 8 | 8 |
| High LVEF True | 3 | 38 |

Example 6: Analysis Control Subject Versus AMI Patients at DO Total Seq on Cardiac Enriched lncRNAs Quantification of lncRNAs in body fluids including but not limited to whole blood, serum, plasma, urine, saliva is a non-invasive way to develop a diagnostic test to use in clinics. The expression of circulating lncRNA is studied in serum samples from patients with AMI and control subjects. Serum samples collected at DO of patient with AMI from the MitoCare cohort and control subject of chronobiological study are used for lncRNA profiling. Mitocare demographics are presented in Table 3. Technical workflow is identical as described in Example 3.

Results:

Comparison Between Control Subject Versus AMI Patients at DO

First, samples are grouped into 2 group by a dichotomized variable: patients with cardiac disorder (AMI) and subjects with no cardiac disease. We found that 1736 lncRNAs are differentially expressed (p<0.05). Most of the lncRNAs are overexpressed in patient undergoing an AMI. We show here that the lncRNAs identified in heart biopsie are biomarkers for diagnosis of heart diseases. By selecting lncRNAs with p<0.01; a fold change>2 or <0.5 and an individual AUC>0.8 or <0.2, we identified a list of 288 lncRNAs that can diagnose AMI or heart diseases (Table 32).

TABLE 32 list of 288 lncRNAs differentially expressed, with a fold change > 2 or < 0.5 and an individual AUC > 0.8 or < 0.2.

| LncRNA (SEQ ID NO:) | P-Value | Fold change | auc | LncRNA (SEQ ID NO:) | P-Value | Fold change | auc | LncRNA (SEQ ID NO:) | P-Value | Fold change | auc |
|---|---|---|---|---|---|---|---|---|---|---|---|
| 0014 | 0.00009 | 0.49 | 0.19 | 0955 | 0.00023 | 0.37 | 0.16 | 1735 | 0.00000 | 0.19 | 0.04 |
| 0020 | 0.00002 | 0.35 | 0.13 | 0970 | 0.00001 | 0.46 | 0.14 | 1739 | 0.00001 | 0.33 | 0.10 |
| 0027 | 0.00005 | 0.31 | 0.16 | 0983 | 0.00000 | 0.46 | 0.11 | 1747 | 0.00001 | 0.37 | 0.15 |
| 0042 | 0.00000 | 0.50 | 0.11 | 0984 | 0.00000 | 0.12 | 0.09 | 1753 | 0.00001 | 0.43 | 0.12 |
| 0051 | 0.00315 | 10.58 | 0.85 | 0986 | 0.00017 | 0.50 | 0.20 | 1761 | 0.00057 | 0.48 | 0.19 |
| 0055 | 0.00001 | 0.42 | 0.13 | 0989 | 0.00027 | 0.32 | 0.19 | 1764 | 0.00112 | 0.32 | 0.19 |
| 0085 | 0.00001 | 0.29 | 0.13 | 0990 | 0.00000 | 0.11 | 0.11 | 1774 | 0.00028 | 0.32 | 0.19 |
| 0097 | 0.00012 | 0.49 | 0.17 | 0995 | 0.00007 | 0.31 | 0.17 | 1777 | 0.00000 | 0.43 | 0.12 |
| 0107 | 0.00009 | 0.26 | 0.16 | 1001 | 0.00004 | 0.44 | 0.17 | 1810 | 0.00010 | 0.50 | 0.17 |
| 0130 | 0.00012 | 0.24 | 0.16 | 1008 | 0.00000 | 0.47 | 0.11 | 1837 | 0.00009 | 0.34 | 0.14 |

TABLE 32-continued list of 288 lncRNAs differentially expressed, with a fold change > 2
or < 0.5 and an individual AUC > 0.8 or < 0.2.

| LncRNA (SEQ ID NO:) | P-Value | Fold change | auc | LncRNA (SEQ ID NO:) | P-Value | Fold change | auc | LncRNA (SEQ ID NO:) | P-Value | Fold change | auc |
|---|---|---|---|---|---|---|---|---|---|---|---|
| 0138 | 0.00007 | 0.47 | 0.17 | 1028 | 0.00010 | 0.31 | 0.19 | 1859 | 0.00000 | 0.43 | 0.13 |
| 0151 | 0.00000 | 0.26 | 0.09 | 1047 | 0.00005 | 0.43 | 0.19 | 1874 | 0.00030 | 0.43 | 0.20 |
| 0155 | 0.00007 | 0.32 | 0.15 | 1051 | 0.00002 | 0.49 | 0.16 | 1888 | 0.00000 | 0.34 | 0.09 |
| 0176 | 0.00025 | 0.44 | 0.17 | 1055 | 0.00000 | 0.46 | 0.03 | 1891 | 0.00006 | 0.44 | 0.18 |
| 0190 | 0.00000 | 0.34 | 0.05 | 1066 | 0.00000 | 0.48 | 0.09 | 1893 | 0.00005 | 0.06 | 0.13 |
| 0199 | 0.00030 | 0.46 | 0.19 | 1072 | 0.00000 | 0.29 | 0.07 | 1900 | 0.00041 | 0.40 | 0.20 |
| 0206 | 0.00003 | 0.40 | 0.16 | 1086 | 0.00000 | 0.31 | 0.08 | 1927 | 0.00000 | 0.48 | 0.09 |
| 0210 | 0.00001 | 0.48 | 0.12 | 1088 | 0.00001 | 0.20 | 0.15 | 1947 | 0.00000 | 0.33 | 0.12 |
| 0215 | 0.00003 | 0.27 | 0.16 | 1106 | 0.00004 | 0.40 | 0.14 | 1963 | 0.00000 | 0.40 | 0.09 |
| 0226 | 0.00000 | 0.46 | 0.02 | 1113 | 0.00000 | 0.34 | 0.13 | 1975 | 0.00024 | 0.26 | 0.18 |
| 0227 | 0.00001 | 0.46 | 0.15 | 1115 | 0.00022 | 0.43 | 0.19 | 1985 | 0.00468 | 0.46 | 0.20 |
| 0236 | 0.00009 | 0.44 | 0.17 | 1116 | 0.00000 | 0.49 | 0.03 | 1991 | 0.00000 | 0.33 | 0.10 |
| 0251 | 0.00010 | 0.26 | 0.20 | 1131 | 0.00000 | 0.25 | 0.05 | 1992 | 0.00000 | 0.47 | 0.11 |
| 0263 | 0.00032 | 0.42 | 0.20 | 1135 | 0.00024 | 0.40 | 0.19 | 1994 | 0.00000 | 0.43 | 0.06 |
| 0268 | 0.00001 | 0.43 | 0.14 | 1138 | 0.00000 | 0.25 | 0.10 | 1998 | 0.00000 | 0.48 | 0.05 |
| 0281 | 0.00003 | 0.44 | 0.14 | 1142 | 0.00037 | 7.14 | 0.97 | 1999 | 0.00002 | 0.41 | 0.13 |
| 0293 | 0.00000 | 0.12 | 0.16 | 1146 | 0.00008 | 0.38 | 0.17 | 2020 | 0.00001 | 0.39 | 0.13 |
| 0325 | 0.00100 | 0.20 | 0.18 | 1180 | 0.00005 | 0.18 | 0.17 | 2043 | 0.00001 | 0.11 | 0.10 |
| 0330 | 0.00008 | 0.27 | 0.16 | 1184 | 0.00000 | 0.36 | 0.07 | 2059 | 0.00005 | 0.38 | 0.16 |
| 0350 | 0.00000 | 0.38 | 0.10 | 1211 | 0.00000 | 0.47 | 0.02 | 2065 | 0.00000 | 0.43 | 0.02 |
| 0365 | 0.00001 | 0.47 | 0.14 | 1220 | 0.00000 | 0.41 | 0.12 | 2070 | 0.00000 | 0.32 | 0.12 |
| 0368 | 0.00022 | 0.32 | 0.20 | 1239 | 0.00001 | 0.43 | 0.14 | 2071 | 0.00001 | 0.37 | 0.13 |
| 0372 | 0.00009 | 0.35 | 0.18 | 1253 | 0.00030 | 0.28 | 0.17 | 2077 | 0.00005 | 0.10 | 0.07 |
| 0374 | 0.00032 | 0.23 | 0.17 | 1276 | 0.00164 | 0.40 | 0.19 | 2082 | 0.00000 | 0.42 | 0.12 |
| 0383 | 0.00054 | 0.49 | 0.19 | 1291 | 0.00000 | 0.38 | 0.08 | 2085 | 0.00002 | 0.28 | 0.14 |
| 0387 | 0.00006 | 0.41 | 0.18 | 1297 | 0.00000 | 0.43 | 0.02 | 2093 | 0.00000 | 0.26 | 0.10 |
| 0396 | 0.00019 | 0.34 | 0.17 | 1301 | 0.00011 | 0.25 | 0.16 | 2108 | 0.00000 | 0.21 | 0.07 |
| 0402 | 0.00021 | 0.36 | 0.20 | 1306 | 0.00015 | 0.15 | 0.17 | 2127 | 0.00322 | 0.36 | 0.16 |
| 0439 | 0.00029 | 0.45 | 0.19 | 1307 | 0.00005 | 0.30 | 0.16 | 2129 | 0.00000 | 0.47 | 0.13 |
| 0465 | 0.00000 | 0.31 | 0.05 | 1314 | 0.00001 | 0.46 | 0.14 | 2133 | 0.00061 | 0.45 | 0.19 |
| 0486 | 0.00041 | 0.46 | 0.19 | 1320 | 0.00004 | 0.18 | 0.12 | 2148 | 0.00000 | 2.04 | 0.89 |
| 0494 | 0.00003 | 0.42 | 0.16 | 1336 | 0.00006 | 0.48 | 0.17 | 2156 | 0.00010 | 0.18 | 0.16 |
| 0499 | 0.00000 | 0.38 | 0.13 | 1350 | 0.00008 | 0.48 | 0.19 | 2161 | 0.00000 | 2.05 | 0.93 |
| 0507 | 0.00001 | 0.17 | 0.13 | 1357 | 0.00008 | 0.29 | 0.13 | 2163 | 0.00000 | 0.19 | 0.05 |
| 0511 | 0.00016 | 0.44 | 0.17 | 1367 | 0.00010 | 0.34 | 0.16 | 2173 | 0.00000 | 0.46 | 0.04 |
| 0523 | 0.00000 | 0.21 | 0.01 | 1372 | 0.00063 | 0.46 | 0.19 | 2184 | 0.00006 | 0.32 | 0.14 |
| 0538 | 0.00059 | 0.29 | 0.20 | 1374 | 0.00000 | 0.48 | 0.02 | 2192 | 0.00000 | 0.47 | 0.11 |
| 0559 | 0.00016 | 0.47 | 0.19 | 1393 | 0.00000 | 0.37 | 0.12 | 2196 | 0.00005 | 0.44 | 0.16 |
| 0560 | 0.00027 | 0.34 | 0.19 | 1404 | 0.00001 | 0.42 | 0.14 | 2198 | 0.00010 | 0.49 | 0.18 |
| 0564 | 0.00000 | 0.28 | 0.08 | 1415 | 0.00000 | 0.23 | 0.06 | 2207 | 0.00004 | 0.24 | 0.13 |
| 0572 | 0.00000 | 0.21 | 0.09 | 1424 | 0.00024 | 0.31 | 0.17 | 2245 | 0.00002 | 0.38 | 0.16 |
| 0589 | 0.00018 | 0.48 | 0.19 | 1434 | 0.00005 | 0.26 | 0.17 | 2250 | 0.00000 | 0.49 | 0.05 |
| 0594 | 0.00000 | 20.93 | 1.00 | 1469 | 0.00000 | 0.45 | 0.03 | 2260 | 0.00024 | 2.31 | 0.82 |
| 0597 | 0.00009 | 0.17 | 0.09 | 1477 | 0.00000 | 2.06 | 0.90 | 2280 | 0.00012 | 0.12 | 0.12 |
| 0599 | 0.00001 | 0.40 | 0.12 | 1484 | 0.00000 | 0.42 | 0.04 | 2295 | 0.00000 | 0.41 | 0.13 |
| 0639 | 0.00005 | 2.02 | 0.85 | 1492 | 0.00007 | 0.26 | 0.18 | 2310 | 0.00002 | 0.21 | 0.16 |
| 0647 | 0.00000 | 0.43 | 0.10 | 1499 | 0.00000 | 0.37 | 0.09 | 2343 | 0.00017 | 0.33 | 0.20 |
| 0657 | 0.00000 | 0.49 | 0.08 | 1502 | 0.00004 | 0.22 | 0.17 | 2373 | 0.00000 | 0.47 | 0.03 |
| 0662 | 0.00024 | 0.31 | 0.17 | 1509 | 0.00000 | 0.32 | 0.12 | 2406 | 0.00014 | 2.65 | 0.81 |
| 0664 | 0.00001 | 0.42 | 0.15 | 1523 | 0.00027 | 0.31 | 0.16 | 2420 | 0.00001 | 0.40 | 0.12 |
| 0668 | 0.00015 | 0.29 | 0.18 | 1532 | 0.00005 | 0.17 | 0.16 | 2462 | 0.00000 | 0.36 | 0.08 |
| 0674 | 0.00000 | 0.47 | 0.13 | 1534 | 0.00000 | 0.48 | 0.00 | 2479 | 0.00063 | 0.49 | 0.19 |
| 0685 | 0.00009 | 0.46 | 0.17 | 1537 | 0.00009 | 0.40 | 0.15 | 2488 | 0.00000 | 0.40 | 0.09 |
| 0696 | 0.00010 | 0.29 | 0.16 | 1567 | 0.00012 | 0.47 | 0.16 | 2489 | 0.00018 | 2.10 | 0.81 |
| 0697 | 0.00000 | 0.23 | 0.12 | 1572 | 0.00003 | 0.43 | 0.15 | 2571 | 0.00001 | 0.36 | 0.14 |
| 0707 | 0.00000 | 0.43 | 0.05 | 1582 | 0.00026 | 0.13 | 0.17 | 2584 | 0.00000 | 0.45 | 0.07 |
| 0710 | 0.00003 | 0.40 | 0.17 | 1585 | 0.00026 | 2.17 | 0.83 | 2603 | 0.00000 | 0.42 | 0.02 |
| 0714 | 0.00002 | 0.37 | 0.11 | 1587 | 0.00000 | 0.40 | 0.10 | 2676 | 0.00000 | 0.49 | 0.12 |
| 0745 | 0.00044 | 0.38 | 0.19 | 1597 | 0.00009 | 0.19 | 0.16 | 2682 | 0.00000 | 0.46 | 0.05 |
| 0755 | 0.00000 | 0.19 | 0.08 | 1601 | 0.00001 | 6.65 | 0.88 | 2766 | 0.00001 | 0.19 | 0.12 |
| 0772 | 0.00006 | 2.32 | 0.82 | 1608 | 0.00046 | 0.44 | 0.20 | 2832 | 0.00064 | 0.45 | 0.19 |
| 0804 | 0.00012 | 0.35 | 0.20 | 1612 | 0.00000 | 0.08 | 0.10 | 2842 | 0.00011 | 0.40 | 0.19 |
| 0809 | 0.00075 | 0.20 | 0.19 | 1624 | 0.00000 | 0.41 | 0.05 | 2868 | 0.00001 | 0.16 | 0.07 |
| 0818 | 0.00000 | 0.46 | 0.01 | 1625 | 0.00000 | 0.21 | 0.05 | 2904 | 0.00242 | 0.20 | 0.14 |
| 0839 | 0.00000 | 0.42 | 0.04 | 1638 | 0.00001 | 2.06 | 0.85 | 2924 | 0.00000 | 2.10 | 0.87 |
| 0846 | 0.00000 | 0.41 | 0.03 | 1646 | 0.00000 | 0.42 | 0.08 | 2939 | 0.00000 | 0.49 | 0.13 |
| 0862 | 0.00024 | 0.32 | 0.19 | 1647 | 0.00000 | 0.44 | 0.05 | 2946 | 0.00000 | 0.41 | 0.04 |
| 0866 | 0.00000 | 0.25 | 0.11 | 1652 | 0.00539 | 0.21 | 0.15 | 2985 | 0.00000 | 0.47 | 0.03 |
| 0884 | 0.00004 | 0.44 | 0.17 | 1670 | 0.00036 | 0.34 | 0.20 | 2996 | 0.00047 | 0.15 | 0.17 |
| 0886 | 0.00001 | 0.32 | 0.12 | 1680 | 0.00003 | 0.26 | 0.13 | 3006 | 0.00002 | 0.43 | 0.16 |
| 0899 | 0.00000 | 0.38 | 0.10 | 1716 | 0.00000 | 0.12 | 0.10 | 3073 | 0.00037 | 0.37 | 0.19 |
| 0916 | 0.00000 | 0.41 | 0.03 | 1717 | 0.00062 | 0.05 | 0.15 | 3133 | 0.00000 | 0.39 | 0.02 |
| 0917 | 0.00003 | 0.33 | 0.15 | 1719 | 0.00038 | 0.30 | 0.20 | 3139 | 0.00000 | 0.28 | 0.07 |

TABLE 32-continued list of 288 lncRNAs differentially expressed, with a fold change > 2
or < 0.5 and an individual AUC > 0.8 or < 0.2.

| LncRNA (SEQ ID NO:) | P-Value | Fold change | auc | LncRNA (SEQ ID NO:) | P-Value | Fold change | auc | LncRNA (SEQ ID NO:) | P-Value | Fold change | auc |
|---|---|---|---|---|---|---|---|---|---|---|---|
| 0936 | 0.00005 | 0.45 | 0.17 | 1721 | 0.00001 | 0.37 | 0.15 | 3198 | 0.00000 | 0.46 | 0.08 |
| 0939 | 0.00009 | 0.29 | 0.19 | 1731 | 0.00000 | 0.06 | 0.09 | 3212 | 0.00000 | 0.49 | 0.09 |
| 0949 | 0.00000 | 0.45 | 0.05 | 1732 | 0.00002 | 0.45 | 0.14 | 3220 | 0.00033 | 0.41 | 0.19 |

Correlation Between lncRNA Expression at D0 and LVEF at 3 Days

In order to predict outcome of patient suffering from AMI at day 3 and recovery of the patients, LVEF at day 3 is considered as continuous value and spearman correlation is performed between lncRNA expression at D0 and LVEF at day 3. We found that 72 lncRNAs present a correlation factor over 0.45 or below −0.45 as represented in Table 33. These lncRNAs can be used as predictor of outcome 3 days after AMI to evaluate LVEF.

TABLE 33

72 lncRNAs with spearman correlation factor over
0.45 or below −0.45 wit LVEF at D3.

| LncRNA (SEQ ID NO:) | Correlation |
|---|---|
| 0026 | −0.475 |
| 0090 | −0.530 |
| 0097 | 0.453 |
| 0103 | −0.639 |
| 0131 | −0.512 |
| 0212 | −0.454 |
| 0242 | 0.517 |
| 0255 | −0.559 |
| 0266 | −0.649 |
| 0433 | −0.504 |
| 0489 | −0.454 |
| 0563 | 0.494 |
| 0573 | −0.537 |
| 0595 | −0.605 |
| 0602 | 0.557 |
| 0718 | 0.593 |
| 0721 | −0.472 |
| 0741 | −0.598 |
| 0777 | −0.617 |
| 0786 | −0.529 |
| 0900 | −0.469 |
| 0903 | −0.629 |
| 0947 | −0.473 |
| 1021 | −0.508 |
| 1034 | 0.453 |
| 1045 | −0.474 |
| 1051 | −0.499 |
| 1076 | −0.652 |
| 1176 | −0.512 |
| 1245 | −0.568 |
| 1295 | 0.599 |
| 1373 | 0.533 |
| 1391 | 0.500 |
| 1392 | −0.474 |
| 1482 | −0.492 |
| 1514 | −0.453 |
| 1571 | −0.476 |
| 1579 | 0.506 |
| 1637 | −0.469 |
| 1830 | −0.477 |
| 1847 | −0.465 |
| 1848 | 0.666 |
| 1932 | −0.531 |
| 1947 | −0.477 |
| 2091 | −0.553 |
| 2095 | −0.496 |
| 2244 | −0.458 |
| 2258 | −0.595 |
| 2273 | 0.502 |
| 2307 | −0.547 |
| 2312 | 0.574 |
| 2329 | 0.545 |
| 2371 | 0.493 |
| 2387 | 0.594 |
| 2390 | 0.644 |
| 2396 | −0.513 |
| 2429 | 0.529 |
| 2452 | 0.452 |
| 2517 | 0.531 |
| 2523 | −0.479 |
| 2549 | −0.520 |
| 2628 | −0.505 |
| 2674 | −0.492 |
| 2709 | −0.487 |
| 2827 | 0.501 |
| 2829 | 0.587 |
| 2858 | −0.457 |
| 2900 | 0.470 |
| 2907 | −0.481 |
| 2996 | −0.514 |
| 3054 | 0.455 |
| 3166 | 0.551 |

Among these lncRNA, 4 lncRNA (SEQ0097, SEQ1947, SEQ1051 and SEQ2996) are differentially expressed between controls and AMI, and are correlated to LVEF value at D3.

Example 7: Analysis of Gencode lncRNAs from Serum RNA-Seq Data

Quantification of lncRNAs in body fluids including but not limited to whole blood, serum, plasma, urine, saliva is a non-invasive way to develop a diagnostic test to use in clinics. The expression of circulating lncRNA is studied in serum samples from patients with AMI and control subjects.

Serum samples collected at D0 and D3-D5 of patient with AMI from the MitoCare cohort and control subject of chronobiological study are used for lncRNA profiling. Mitocare demographics are presented in Table 3. Technical workflow is identical as described in Example 3 and sequencing data are aligned against Gencode database from LNCipedia 5.0. Cardiac enriched lncRNAs (SEQ0001 to SEQ3238) are removed from the analysis. A threshold of 10 CPM in half of samples in one group is applied to consider the lncRNA as positive.

In this analysis, focus is done on circulating lncRNAs to be used as biomarkers for the prediction and monitoring of Left Ventricular Remodeling and development of heart failure.

Comparison Between Low LVEF (LVEF≤40%) and High LVEF (LVEF>40%) at D3-D5 Serum Samples First, samples are classified into 2 group by a dichotomized variable: 1-month LVEF<40% considered as LV dysfunction (Ventricular remodeling) and 1-month LVEF>40% considered as preserved LV function.

291 lncRNA are differentially expressed and among these, 82 lncRNA are differentially expressed and have a fold change>2 or <0.5 between the low LVEF (LVEF≤40%) and the high LVEF (LVEF>40%). The p-value and the fold-change of these lncRNA are listed in the Table 34. 468 lncRNAs which have a p<0.05 and/or an individual AUC>0.7 or <0.3 are listed in Table 35.

TABLE 34

List of 86 lncRNAs from Gencode database which are differentially expressed (p < 0.05) and have a fold change >2 or <0.5 between the low LVEF group (LVEF ≤ 40%) and the high LVEF group (LVEF > 40%)

| lncRNA | P value | foldchange |
|---|---|---|
| ENST00000491676.1 | 0.002 | 0.461 |
| ENST00000512458.1 | 0.002 | 0.211 |
| ENST00000485020.1 | 0.002 | 3.802 |
| ENST00000487814.1 | 0.002 | 2.091 |
| ENST00000515306.1 | 0.003 | 3.302 |
| ENST00000426551.1 | 0.004 | 0.244 |
| ENST00000412944.1 | 0.004 | 8.646 |
| ENST00000553319.1 | 0.004 | 0.493 |
| ENST00000421563.1 | 0.005 | 0.435 |
| ENST00000427732.1 | 0.006 | 5.310 |
| ENST00000506068.1 | 0.006 | 5.486 |
| ENST00000417420.1 | 0.006 | 5.855 |
| ENST00000514942.2 | 0.007 | 2.865 |
| ENST00000461943.1 | 0.009 | 2.816 |
| ENST00000507932.1 | 0.009 | 0.238 |
| ENST00000456255.1 | 0.010 | 0.295 |
| ENST00000519929.1 | 0.011 | 0.357 |
| ENST00000466034.1 | 0.013 | 6.486 |
| ENST00000399152.2 | 0.013 | 3.882 |
| ENST00000422417.1 | 0.014 | 0.262 |
| ENST00000503037.1 | 0.015 | 0.430 |
| ENST00000515811.1 | 0.015 | 3.365 |
| ENST00000502861.1 | 0.016 | 2.281 |
| ENST00000455541.1 | 0.016 | 0.382 |
| ENST00000424592.1 | 0.016 | 2.843 |
| ENST00000431911.1 | 0.017 | 0.422 |
| ENST00000452618.1 | 0.017 | 2.526 |
| ENST00000437488.1 | 0.018 | 0.333 |
| ENST00000443066.2 | 0.018 | 3.846 |
| ENST00000457169.1 | 0.018 | 10.873 |
| ENST00000447761.1 | 0.019 | 2.455 |
| ENST00000527035.1 | 0.019 | 0.313 |
| ENST00000522525.1 | 0.021 | 2.384 |

TABLE 34-continued

List of 86 lncRNAs from Gencode database which are differentially expressed (p < 0.05) and have a fold change >2 or <0.5 between the low LVEF group (LVEF ≤ 40%) and the high LVEF group (LVEF > 40%)

| lncRNA | P value | foldchange |
|---|---|---|
| ENST00000602445.1 | 0.022 | 13.038 |
| ENST00000431569.1 | 0.022 | 4.473 |
| ENST00000609450.1 | 0.022 | 0.498 |
| ENST00000501965.2 | 0.022 | 2.161 |
| ENST00000441026.1 | 0.022 | 2.312 |
| ENST00000432125.2 | 0.022 | 2.253 |
| ENST00000609549.1 | 0.023 | 0.393 |
| ENST00000514526.1 | 0.023 | 0.286 |
| ENST00000510946.1 | 0.024 | 3.217 |
| ENST00000521819.1 | 0.025 | 0.140 |
| ENST00000608774.1 | 0.025 | 0.481 |
| ENST00000601586.1 | 0.026 | 0.399 |
| ENST00000508847.1 | 0.026 | 0.229 |
| ENST00000421696.2 | 0.026 | 2.796 |
| ENST00000601913.1 | 0.028 | 3.766 |
| ENST00000494900.1 | 0.029 | 2.198 |
| ENST00000434207.1 | 0.030 | 2.133 |
| ENST00000452809.1 | 0.031 | 2.428 |
| ENST00000498413.1 | 0.032 | 0.321 |
| ENST00000507957.1 | 0.034 | 2.706 |
| ENST00000443562.1 | 0.034 | 0.355 |
| ENST00000577528.1 | 0.034 | 0.218 |
| ENST00000439964.1 | 0.035 | 0.367 |
| ENST00000515184.1 | 0.035 | 0.469 |
| ENST00000452795.2 | 0.035 | 0.392 |
| ENST00000427213.1 | 0.036 | 2.863 |
| ENST00000416506.1 | 0.037 | 0.411 |
| ENST00000432038.1 | 0.037 | 0.488 |
| ENST00000521805.1 | 0.037 | 0.403 |
| ENST00000498480.1 | 0.038 | 0.492 |
| ENST00000455988.1 | 0.038 | 3.218 |
| ENST00000606056.1 | 0.038 | 0.331 |
| ENST00000509057.1 | 0.038 | 0.457 |
| ENST00000465215.1 | 0.039 | 0.122 |
| ENST00000514368.1 | 0.040 | 0.349 |
| ENST00000585826.1 | 0.040 | 3.226 |
| ENST00000472821.1 | 0.041 | 3.001 |
| ENST00000588108.1 | 0.041 | 0.386 |
| ENST00000421640.1 | 0.041 | 2.670 |
| ENST00000437290.2 | 0.042 | 0.193 |
| ENST00000415629.2 | 0.043 | 0.118 |
| ENST00000489690.1 | 0.043 | 0.481 |
| ENST00000513219.1 | 0.043 | 0.416 |
| ENST00000419614.1 | 0.043 | 2.574 |
| ENST00000604677.1 | 0.044 | 3.502 |
| ENST00000440574.1 | 0.048 | 2.392 |
| ENST00000435643.1 | 0.048 | 0.212 |
| ENST00000587568.1 | 0.050 | 3.194 |
| ENST00000413525.1 | 0.050 | 4.403 |

TABLE 35

List of 468 lncRNA from Gencode database which are differentially expressed (p < 0.05) and/or have an AUC > 0.7 or < 0.3 between the low LVEF group (LVEF ≤ 40%) and the high LVEF group (LVEF > 40%)

| lncRNA | p Value | auc | lncRNA | p Value | auc | lncRNA | p Value | auc |
|---|---|---|---|---|---|---|---|---|
| ENST00000425754.1 | 00000 | 00850 | ENST00000504046.1 | 00027 | 00800 | ENST00000466225.2 | 00056 | 00255 |
| ENST00000609071.1 | 00000 | 00875 | ENST00000607662.1 | 00027 | 00705 | ENST00000510230.1 | 00057 | 00283 |
| ENST00000503929.1 | 00000 | 00825 | ENST00000487624.1 | 00027 | 00720 | ENST00000453039.1 | 00057 | 00780 |
| ENST00000562952.1 | 00001 | 00830 | ENST00000340444.1 | 00027 | 00270 | ENST00000500224.2 | 00057 | 00225 |
| ENST00000587099.1 | 00001 | 00860 | ENST00000430048.1 | 00027 | 00740 | ENST00000510198.1 | 00057 | 00275 |
| ENST00000424895.1 | 00001 | 00825 | ENST00000453665.1 | 00028 | 00280 | ENST00000515199.1 | 00058 | 00700 |
| ENST00000608537.1 | 00001 | 00810 | ENST00000607797.1 | 00028 | 00735 | ENST00000505626.1 | 00058 | 00725 |
| ENST00000414309.1 | 00002 | 00850 | ENST00000446139.1 | 00028 | 00745 | ENST00000522350.1 | 00058 | 00240 |
| ENST00000491676.1 | 00002 | 00160 | ENST00000589496.2 | 00028 | 00745 | ENST00000507236.1 | 00058 | 00265 |
| ENST00000412134.1 | 00002 | 00805 | ENST00000601913.1 | 00028 | 00580 | ENST00000417557.1 | 00058 | 00735 |
| ENST00000565538.1 | 00002 | 00810 | ENST00000431557.1 | 00029 | 00245 | ENST00000609881.1 | 00058 | 00295 |
| ENST00000508752.1 | 00002 | 00795 | ENST00000439050.1 | 00029 | 00750 | ENST00000458359.1 | 00059 | 00270 |

TABLE 35-continued

List of 468 lncRNA from Gencode database which are differentially expressed (p < 0.05) and/or have an AUC > 0.7 or < 0.3 between the low LVEF group (LVEF ≤ 40%) and the high LVEF group (LVEF > 40%)

| lncRNA | p Value | auc | lncRNA | p Value | auc | lncRNA | p Value | auc |
|---|---|---|---|---|---|---|---|---|
| ENST00000512458.1 | 00002 | 00123 | ENST00000494900.1 | 00029 | 00680 | ENST00000564748.1 | 00059 | 00710 |
| ENST00000485020.1 | 00002 | 00810 | ENST00000456687.3 | 00029 | 00260 | ENST00000427892.1 | 00059 | 00275 |
| ENST00000487814.1 | 00002 | 00820 | ENST00000505162.1 | 00029 | 00725 | ENST00000511634.1 | 00059 | 00285 |
| ENST00000598757.1 | 00002 | 00170 | ENST00000597366.1 | 00030 | 00715 | ENST00000606287.1 | 00061 | 00290 |
| ENST00000515306.1 | 00003 | 00790 | ENST00000566366.1 | 00030 | 00290 | ENST00000456469.1 | 00061 | 00270 |
| ENST00000443613.2 | 00003 | 00190 | ENST00000434207.1 | 00030 | 00715 | ENST00000418620.1 | 00062 | 00265 |
| ENST00000507344.1 | 00004 | 00815 | ENST00000609168.1 | 00030 | 00715 | ENST00000602484.1 | 00062 | 00735 |
| ENST00000426551.1 | 00004 | 00170 | ENST00000436488.1 | 00030 | 00250 | ENST00000473713.1 | 00063 | 00275 |
| ENST00000412944.1 | 00004 | 00720 | ENST00000506852.1 | 00031 | 00700 | ENST00000503321.1 | 00064 | 00290 |
| ENST00000513958.1 | 00004 | 00195 | ENST00000452809.1 | 00031 | 00675 | ENST00000432386.1 | 00065 | 00280 |
| ENST00000511064.1 | 00004 | 00790 | ENST00000442410.2 | 00031 | 00305 | ENST00000440358.1 | 00065 | 00275 |
| ENST00000448901.1 | 00004 | 00795 | ENST00000609354.1 | 00031 | 00725 | ENST00000440371.1 | 00066 | 00290 |
| ENST00000553319.1 | 00004 | 00150 | ENST00000429315.3 | 00032 | 00285 | ENST00000457364.2 | 00066 | 00300 |
| ENST00000421563.1 | 00005 | 00205 | ENST00000496488.1 | 00032 | 00215 | ENST00000510349.1 | 00066 | 00290 |
| ENST00000497573.1 | 00005 | 00140 | ENST00000421157.1 | 00032 | 00735 | ENST00000528692.1 | 00067 | 00295 |
| ENST00000456026.1 | 00005 | 00775 | ENST00000498413.1 | 00032 | 00245 | ENST00000606239.1 | 00067 | 00710 |
| ENST00000427732.1 | 00006 | 00745 | ENST00000511693.1 | 00033 | 00160 | ENST00000443928.2 | 00067 | 00295 |
| ENST00000506068.1 | 00006 | 00730 | ENST00000602433.1 | 00033 | 00775 | ENST00000453828.1 | 00067 | 00300 |
| ENST00000512712.2 | 00006 | 00200 | ENST00000507957.1 | 00034 | 00690 | ENST00000608123.1 | 00067 | 00295 |
| ENST00000417420.1 | 00006 | 00735 | ENST00000443562.1 | 00034 | 00245 | ENST00000602434.1 | 00067 | 00715 |
| ENST00000568686.1 | 00006 | 00245 | ENST00000577528.1 | 00034 | 00250 | ENST00000441870.1 | 00067 | 00295 |
| ENST00000543490.1 | 00006 | 00785 | ENST00000415706.1 | 00034 | 00675 | ENST00000449012.1 | 00068 | 00270 |
| ENST00000503815.1 | 00007 | 00185 | ENST00000439964.1 | 00035 | 00260 | ENST00000610235.1 | 00069 | 00285 |
| ENST00000565044.1 | 00007 | 00195 | ENST00000503593.1 | 00035 | 00675 | ENST00000427176.1 | 00070 | 00295 |
| ENST00000514942.2 | 00007 | 00735 | ENST00000498457.1 | 00035 | 00285 | ENST00000417324.1 | 00070 | 00300 |
| ENST00000607216.1 | 00007 | 00160 | ENST00000451992.2 | 00035 | 00205 | ENST00000610094.1 | 00071 | 00290 |
| ENST00000412294.1 | 00007 | 00785 | ENST00000608465.1 | 00035 | 00740 | ENST00000594608.1 | 00071 | 00300 |
| ENST00000430666.1 | 00007 | 00205 | ENST00000244820.2 | 00035 | 00720 | ENST00000607338.1 | 00071 | 00295 |
| ENST00000415330.2 | 00007 | 00200 | ENST00000413304.2 | 00035 | 00275 | ENST00000606696.1 | 00073 | 00700 |
| ENST00000429666.1 | 00008 | 00215 | ENST00000515184.1 | 00035 | 00260 | ENST00000513926.1 | 00073 | 00285 |
| ENST00000499713.2 | 00008 | 00220 | ENST00000452795.2 | 00035 | 00243 | ENST00000596887.1 | 00074 | 00705 |
| ENST00000608574.1 | 00008 | 00170 | ENST00000427213.1 | 00036 | 00750 | ENST00000433084.1 | 00074 | 00290 |
| ENST00000420365.1 | 00008 | 00220 | ENST00000424451.1 | 00036 | 00665 | ENST00000600928.1 | 00074 | 00240 |
| ENST00000421998.1 | 00008 | 00240 | ENST00000503403.1 | 00036 | 00700 | ENST00000606233.1 | 00075 | 00280 |
| ENST00000424244.1 | 00009 | 00265 | ENST00000416506.1 | 00037 | 00240 | ENST00000439795.1 | 00076 | 00280 |
| ENST00000552220.1 | 00009 | 00795 | ENST00000432038.1 | 00037 | 00255 | ENST00000310916.3 | 00076 | 00710 |
| ENST00000428156.1 | 00009 | 00770 | ENST00000521805.1 | 00037 | 00255 | ENST00000457079.1 | 00077 | 00295 |
| ENST00000429725.1 | 00009 | 00780 | ENST00000425914.2 | 00037 | 00285 | ENST00000443093.2 | 00078 | 00255 |
| ENST00000461943.1 | 00009 | 00715 | ENST00000604716.1 | 00037 | 00260 | ENST00000443237.1 | 00078 | 00300 |
| ENST00000508572.1 | 00009 | 00225 | ENST00000507565.1 | 00037 | 00720 | ENST00000424628.1 | 00079 | 00290 |
| ENST00000507932.1 | 00009 | 00205 | ENST00000367716.3 | 00037 | 00255 | ENST00000587162.1 | 00079 | 00300 |
| ENST00000418602.1 | 00010 | 00250 | ENST00000514239.1 | 00037 | 00270 | ENST00000609900.1 | 00080 | 00705 |
| ENST00000505680.1 | 00010 | 00755 | ENST00000498480.1 | 00038 | 00270 | ENST00000608069.1 | 00081 | 00775 |
| ENST00000419578.1 | 00010 | 00785 | ENST00000512435.1 | 00038 | 00270 | ENST00000600062.1 | 00081 | 00700 |
| ENST00000475939.1 | 00010 | 00195 | ENST00000455988.1 | 00038 | 00660 | ENST00000566840.1 | 00081 | 00295 |
| ENST00000456255.1 | 00010 | 00193 | ENST00000606056.1 | 00038 | 00220 | ENST00000507776.1 | 00082 | 00250 |
| ENST00000610058.1 | 00011 | 00775 | ENST00000509057.1 | 00038 | 00240 | ENST00000453732.1 | 00083 | 00290 |
| ENST00000607786.1 | 00011 | 00735 | ENST00000608511.1 | 00038 | 00240 | ENST00000452553.1 | 00083 | 00295 |
| ENST00000439898.1 | 00011 | 00255 | ENST00000452212.1 | 00039 | 00315 | ENST00000504250.1 | 00084 | 00285 |
| ENST00000519929.1 | 00011 | 00185 | ENST00000510302.1 | 00039 | 00780 | ENST00000417926.1 | 00084 | 00710 |
| ENST00000447181.1 | 00011 | 00275 | ENST00000511602.1 | 00039 | 00695 | ENST00000512035.1 | 00084 | 00285 |
| ENST00000504287.1 | 00012 | 00745 | ENST00000515186.1 | 00039 | 00705 | ENST00000515286.1 | 00084 | 00270 |
| ENST00000435552.1 | 00012 | 00260 | ENST00000412092.2 | 00039 | 00330 | ENST00000587306.1 | 00085 | 00280 |
| ENST00000366441.2 | 00012 | 00745 | ENST00000413828.2 | 00039 | 00280 | ENST00000557729.1 | 00086 | 00245 |
| ENST00000441790.1 | 00012 | 00780 | ENST00000465215.1 | 00039 | 00375 | ENST00000610091.1 | 00086 | 00715 |
| ENST00000505018.1 | 00012 | 00755 | ENST00000606582.1 | 00040 | 00680 | ENST00000602919.1 | 00086 | 00300 |
| ENST00000496733.2 | 00012 | 00730 | ENST00000417786.1 | 00040 | 00275 | ENST00000441773.1 | 00086 | 00295 |
| ENST00000440322.1 | 00012 | 00770 | ENST00000514368.1 | 00040 | 00258 | ENST00000589150.1 | 00087 | 00300 |
| ENST00000514600.1 | 00012 | 00725 | ENST00000585826.1 | 00040 | 00680 | ENST00000589487.1 | 00087 | 00258 |
| ENST00000441272.2 | 00013 | 00265 | ENST00000441245.1 | 00041 | 00295 | ENST00000503589.1 | 00087 | 00280 |
| ENST00000466034.1 | 00013 | 00525 | ENST00000472821.1 | 00041 | 00595 | ENST00000414765.1 | 00090 | 00295 |
| ENST00000587085.1 | 00013 | 00750 | ENST00000427439.1 | 00041 | 00725 | ENST00000433186.1 | 00090 | 00278 |
| ENST00000399543.1 | 00013 | 00230 | ENST00000588108.1 | 00041 | 00210 | ENST00000427804.1 | 00091 | 00295 |
| ENST00000595732.1 | 00013 | 00220 | ENST00000441504.1 | 00041 | 00683 | ENST00000439246.1 | 00091 | 00265 |
| ENST00000399152.2 | 00013 | 00705 | ENST00000494582.1 | 00041 | 00675 | ENST00000431268.1 | 00091 | 00260 |
| ENST00000414128.1 | 00014 | 00215 | ENST00000506465.1 | 00041 | 00280 | ENST00000510637.1 | 00091 | 00745 |
| ENST00000502934.1 | 00014 | 00765 | ENST00000511385.1 | 00041 | 00320 | ENST00000446029.1 | 00092 | 00288 |
| ENST00000441053.1 | 00014 | 00255 | ENST00000421640.1 | 00041 | 00610 | ENST00000503488.2 | 00092 | 00705 |
| ENST00000422417.1 | 00014 | 00253 | ENST00000437290.2 | 00042 | 00255 | ENST00000462835.1 | 00093 | 00285 |
| ENST00000422038.1 | 00014 | 00765 | ENST00000602108.1 | 00042 | 00260 | ENST00000435557.1 | 00093 | 00290 |
| ENST00000607723.1 | 00015 | 00750 | ENST00000416349.1 | 00042 | 00705 | ENST00000515405.1 | 00093 | 00240 |
| ENST00000503037.1 | 00015 | 00195 | ENST00000445180.2 | 00042 | 00235 | ENST00000423921.1 | 00093 | 00190 |
| ENST00000515811.1 | 00015 | 00815 | ENST00000511592.1 | 00042 | 00675 | ENST00000515842.1 | 00094 | 00295 |
| ENST00000424215.1 | 00015 | 00230 | ENST00000477246.1 | 00042 | 00300 | ENST00000599448.1 | 00094 | 00235 |
| ENST00000482381.1 | 00015 | 00240 | ENST00000512155.1 | 00042 | 00310 | ENST00000605698.1 | 00095 | 00300 |

TABLE 35-continued

List of 468 lncRNA from Gencode database which are differentially expressed (p < 0.05) and/or have an
AUC > 0.7 or < 0.3 between the low LVEF group (LVEF ≤ 40%) and the high LVEF group (LVEF > 40%)

| lncRNA | p Value | auc | lncRNA | p Value | auc | lncRNA | p Value | auc |
|---|---|---|---|---|---|---|---|---|
| ENST00000410830.1 | 00015 | 00235 | ENST00000608077.1 | 00042 | 00290 | ENST00000510753.1 | 00095 | 00715 |
| ENST00000513572.1 | 00016 | 00760 | ENST00000415629.2 | 00043 | 00275 | ENST00000414634.1 | 00097 | 00293 |
| ENST00000594898.1 | 00016 | 00783 | ENST00000424474.2 | 00043 | 00280 | ENST00000517934.1 | 00098 | 00270 |
| ENST00000479610.1 | 00016 | 00255 | ENST00000605740.1 | 00043 | 00730 | ENST00000510850.1 | 00099 | 00700 |
| ENST00000502861.1 | 00016 | 00790 | ENST00000489690.1 | 00043 | 00283 | ENST00000414688.1 | 00099 | 00710 |
| ENST00000455541.1 | 00016 | 00205 | ENST00000607950.1 | 00043 | 00285 | ENST00000273083.3 | 00099 | 00290 |
| ENST00000459861.1 | 00016 | 00235 | ENST00000513219.1 | 00043 | 00265 | ENST00000552418.1 | 00099 | 00285 |
| ENST00000424592.1 | 00016 | 00720 | ENST00000419614.1 | 00043 | 00675 | ENST00000436248.3 | 00100 | 00275 |
| ENST00000424246.1 | 00017 | 00750 | ENST00000413234.1 | 00043 | 00285 | ENST00000439893.1 | 00102 | 00250 |
| ENST00000492209.1 | 00017 | 00265 | ENST00000420549.1 | 00043 | 00720 | ENST00000427354.1 | 00102 | 00235 |
| ENST00000448134.1 | 00017 | 00230 | ENST00000458698.2 | 00043 | 00290 | ENST00000517299.1 | 00103 | 00295 |
| ENST00000510853.2 | 00017 | 00240 | ENST00000482019.1 | 00043 | 00310 | ENST00000569711.1 | 00104 | 00280 |
| ENST00000431911.1 | 00017 | 00200 | ENST00000509984.1 | 00044 | 00270 | ENST00000453347.1 | 00106 | 00300 |
| ENST00000451711.1 | 00017 | 00215 | ENST00000501927.2 | 00044 | 00285 | ENST00000507373.1 | 00107 | 00295 |
| ENST00000452618.1 | 00017 | 00705 | ENST00000439024.1 | 00044 | 00658 | ENST00000453155.1 | 00108 | 00295 |
| ENST00000568928.1 | 00017 | 00765 | ENST00000511993.1 | 00044 | 00215 | ENST00000465946.1 | 00108 | 00300 |
| ENST00000563320.1 | 00018 | 00775 | ENST00000515128.1 | 00044 | 00665 | ENST00000515086.1 | 00109 | 00280 |
| ENST00000437488.1 | 00018 | 00240 | ENST00000604677.1 | 00044 | 00665 | ENST00000449086.1 | 00110 | 00745 |
| ENST00000443066.2 | 00018 | 00743 | ENST00000606180.1 | 00045 | 00250 | ENST00000540997.1 | 00111 | 00705 |
| ENST00000445791.1 | 00018 | 00745 | ENST00000579914.1 | 00045 | 00290 | ENST00000572124.1 | 00111 | 00705 |
| ENST00000457169.1 | 00018 | 00685 | ENST00000440900.1 | 00045 | 00690 | ENST00000508986.1 | 00120 | 00288 |
| ENST00000417260.1 | 00018 | 00765 | ENST00000431311.1 | 00046 | 00295 | ENST00000505028.1 | 00120 | 00295 |
| ENST00000448977.1 | 00018 | 00705 | ENST00000484076.1 | 00047 | 00665 | ENST00000426444.1 | 00122 | 00285 |
| ENST00000509745.1 | 00019 | 00230 | ENST00000451101.1 | 00047 | 00265 | ENST00000507916.2 | 00124 | 00700 |
| ENST00000420272.2 | 00019 | 00250 | ENST00000381078.1 | 00047 | 00290 | ENST00000514265.1 | 00126 | 00725 |
| ENST00000447761.1 | 00019 | 00720 | ENST00000609423.1 | 00047 | 00250 | ENST00000510632.1 | 00126 | 00295 |
| ENST00000449845.1 | 00019 | 00220 | ENST00000513955.1 | 00048 | 00730 | ENST00000597651.1 | 00127 | 00295 |
| ENST00000527035.1 | 00019 | 00215 | ENST00000450070.1 | 00048 | 00720 | ENST00000443800.1 | 00132 | 00300 |
| ENST00000484765.2 | 00020 | 00255 | ENST00000440574.1 | 00048 | 00720 | ENST00000508255.1 | 00134 | 00295 |
| ENST00000428891.1 | 00020 | 00240 | ENST00000435643.1 | 00048 | 00260 | ENST00000607847.1 | 00137 | 00705 |
| ENST00000450325.1 | 00021 | 00255 | ENST00000609657.1 | 00048 | 00720 | ENST00000430904.1 | 00140 | 00295 |
| ENST00000430542.1 | 00021 | 00785 | ENST00000512464.1 | 00048 | 00725 | ENST00000594622.1 | 00142 | 00700 |
| ENST00000522525.1 | 00021 | 00735 | ENST00000411509.1 | 00048 | 00635 | ENST00000436121.1 | 00144 | 00710 |
| ENST00000507582.1 | 00021 | 00240 | ENST00000607412.1 | 00049 | 00675 | ENST00000503757.1 | 00145 | 00280 |
| ENST00000505877.1 | 00021 | 00775 | ENST00000430520.1 | 00049 | 00260 | ENST00000507011.1 | 00146 | 00270 |
| ENST00000602445.1 | 00022 | 00525 | ENST00000512882.2 | 00049 | 00665 | ENST00000609270.1 | 00146 | 00735 |
| ENST00000431569.1 | 00022 | 00668 | ENST00000511327.1 | 00049 | 00735 | ENST00000500526.1 | 00147 | 00290 |
| ENST00000609450.1 | 00022 | 00225 | ENST00000436885.1 | 00049 | 00275 | ENST00000429230.1 | 00151 | 00300 |
| ENST00000501965.2 | 00022 | 00710 | ENST00000604215.1 | 00049 | 00685 | ENST00000601684.1 | 00155 | 00290 |
| ENST00000441026.1 | 00022 | 00725 | ENST00000443205.1 | 00049 | 00610 | ENST00000434306.1 | 00155 | 00705 |
| ENST00000431500.2 | 00022 | 00735 | ENST00000504869.1 | 00049 | 00255 | ENST00000602820.1 | 00164 | 00250 |
| ENST00000432125.2 | 00022 | 00765 | ENST00000587568.1 | 00050 | 00690 | ENST00000425449.1 | 00168 | 00730 |
| ENST00000505668.1 | 00023 | 00720 | ENST00000608154.1 | 00050 | 00320 | ENST00000433377.1 | 00169 | 00295 |
| ENST00000609549.1 | 00023 | 00250 | ENST00000510570.1 | 00050 | 00698 | ENST00000424528.2 | 00172 | 00710 |
| ENST00000505736.1 | 00023 | 00755 | ENST00000451289.1 | 00050 | 00720 | ENST00000597871.1 | 00176 | 00300 |
| ENST00000523648.1 | 00023 | 00255 | ENST00000458155.1 | 00050 | 00710 | ENST00000593876.1 | 00177 | 00760 |
| ENST00000458254.1 | 00023 | 00215 | ENST00000606186.1 | 00050 | 00295 | ENST00000412674.1 | 00184 | 00280 |
| ENST00000508719.1 | 00023 | 00750 | ENST00000413525.1 | 00050 | 00650 | ENST00000432658.1 | 00195 | 00718 |
| ENST00000514526.1 | 00023 | 00175 | ENST00000438158.1 | 00050 | 00295 | ENST00000588796.1 | 00207 | 00290 |
| ENST00000601486.1 | 00023 | 00225 | ENST00000483840.1 | 00050 | 00760 | ENST00000430540.1 | 00212 | 00300 |
| ENST00000461864.1 | 00023 | 00755 | ENST00000604448.1 | 00051 | 00725 | ENST00000565748.1 | 00215 | 00715 |
| ENST00000502100.2 | 00023 | 00210 | ENST00000414086.1 | 00051 | 00250 | ENST00000415543.1 | 00215 | 00275 |
| ENST00000510946.1 | 00024 | 00655 | ENST00000457440.1 | 00052 | 00280 | ENST00000485338.1 | 00216 | 00293 |
| ENST00000417481.1 | 00024 | 00255 | ENST00000503998.1 | 00052 | 00720 | ENST00000436706.1 | 00232 | 00300 |
| ENST00000504436.1 | 00024 | 00250 | ENST00000603884.1 | 00052 | 00735 | ENST00000431691.1 | 00235 | 00715 |
| ENST00000508352.1 | 00024 | 00235 | ENST00000444649.1 | 00052 | 00280 | ENST00000522762.1 | 00241 | 00290 |
| ENST00000509416.1 | 00024 | 00780 | ENST00000504249.1 | 00052 | 00280 | ENST00000506086.2 | 00254 | 00300 |
| ENST00000521819.1 | 00025 | 00245 | ENST00000433876.2 | 00053 | 00270 | ENST00000596220.1 | 00258 | 00278 |
| ENST00000455929.1 | 00025 | 00810 | ENST00000607946.1 | 00053 | 00265 | ENST00000468859.1 | 00262 | 00700 |
| ENST00000507361.1 | 00025 | 00250 | ENST00000508696.1 | 00053 | 00708 | ENST00000511241.1 | 00268 | 00290 |
| ENST00000460796.1 | 00025 | 00265 | ENST00000503009.1 | 00054 | 00275 | ENST00000457387.1 | 00276 | 00285 |
| ENST00000608774.1 | 00025 | 00243 | ENST00000488287.1 | 00054 | 00705 | ENST00000451707.1 | 00307 | 00715 |
| ENST00000449783.1 | 00025 | 00735 | ENST00000504989.1 | 00055 | 00295 | ENST00000524210.1 | 00317 | 00720 |
| ENST00000444037.1 | 00026 | 00250 | ENST00000431999.1 | 00055 | 00250 | ENST00000458182.1 | 00323 | 00280 |
| ENST00000601586.1 | 00026 | 00248 | ENST00000513871.1 | 00055 | 00265 | ENST00000447880.1 | 00324 | 00300 |
| ENST00000508847.1 | 00026 | 00255 | ENST00000450709.1 | 00055 | 00255 | ENST00000508000.1 | 00380 | 00720 |
| ENST00000421696.1 | 00026 | 00660 | ENST00000416395.1 | 00055 | 00275 | ENST00000432558.1 | 00463 | 00265 |
| ENST00000601500.1 | 00026 | 00710 | ENST00000568817.1 | 00056 | 00700 | ENST00000465347.1 | 00474 | 00300 |
| ENST00000432981.1 | 00027 | 00200 | ENST00000437267.2 | 00056 | 00245 | ENST00000514802.1 | 00571 | 00295 |

First, samples are grouped into 2 group by a dichotomized variable: 1-month LVEF<45% and 1-month LVEF>45%.

277 lncRNA are differentially expressed and among these, 70 lncRNA are differentially expressed and have a fold change>2 or <0.5 between the low LVEF (LVEF≤45%) and the high LVEF (LVEF>45%) groups. The p-value and the fold-change of these lncRNA are listed in the Table 36. 369 lncRNAs which have a p<0.05 and/or an individual AUC>0.7 or <0.3 are listed in Table 37.

TABLE 36

List of 70 lncRNA from Gencode database which are differentially expressed (p < 0.05) and have a fold change >2 or <0.5 between the low LVEF group (LVEF ≤ 45%) and the high LVEF group (LVEF > 45%)

| lncRNA | p Value | Fold change |
|---|---|---|
| ENST00000437488.1 | 0.000 | 0.072 |
| ENST00000507236.1 | 0.001 | 0.477 |
| ENST00000505848.1 | 0.001 | 0.315 |
| ENST00000509416.1 | 0.002 | 2.150 |
| ENST00000451894.2 | 0.003 | 2.266 |
| ENST00000477805.1 | 0.003 | 0.236 |
| ENST00000562054.1 | 0.004 | 0.456 |
| ENST00000502757.1 | 0.004 | 2.498 |
| ENST00000609549.1 | 0.005 | 0.289 |
| ENST00000519929.1 | 0.006 | 0.354 |
| ENST00000515286.1 | 0.006 | 0.244 |
| ENST00000427825.1 | 0.006 | 0.479 |
| ENST00000457815.1 | 0.007 | 2.063 |
| ENST00000512458.1 | 0.007 | 0.254 |
| ENST00000514724.2 | 0.007 | 0.148 |
| ENST00000513219.1 | 0.008 | 0.271 |
| ENST00000456255.1 | 0.010 | 0.286 |
| ENST00000503037.1 | 0.011 | 0.450 |
| ENST00000427732.1 | 0.011 | 4.147 |
| ENST00000506292.2 | 0.011 | 0.321 |
| ENST00000357876.5 | 0.012 | 0.209 |
| ENST00000588108.1 | 0.013 | 0.260 |
| ENST00000514877.1 | 0.013 | 0.427 |
| ENST00000426551.1 | 0.013 | 0.283 |
| ENST00000440516.1 | 0.013 | 2.510 |
| ENST00000422996.1 | 0.015 | 0.494 |
| ENST00000587306.1 | 0.016 | 0.482 |
| ENST00000439878.1 | 0.017 | 0.484 |
| ENST00000506068.1 | 0.018 | 3.665 |
| ENST00000431650.1 | 0.018 | 0.366 |

TABLE 36-continued

List of 70 lncRNA from Gencode database which are differentially expressed (p < 0.05) and have a fold change >2 or <0.5 between the low LVEF group (LVEF ≤ 45%) and the high LVEF group (LVEF > 45%)

| lncRNA | p Value | Fold change |
|---|---|---|
| ENST00000421498.1 | 0.021 | 3.747 |
| ENST00000507011.1 | 0.022 | 0.282 |
| ENST00000507932.1 | 0.022 | 0.289 |
| ENST00000515405.1 | 0.024 | 0.256 |
| ENST00000432978.1 | 0.024 | 0.453 |
| ENST00000452809.1 | 0.024 | 2.386 |
| ENST00000509999.1 | 0.025 | 2.321 |
| ENST00000515184.1 | 0.026 | 0.456 |
| ENST00000517934.1 | 0.027 | 0.288 |
| ENST00000590186.1 | 0.028 | 0.248 |
| ENST00000510632.1 | 0.028 | 0.389 |
| ENST00000429352.1 | 0.028 | 0.497 |
| ENST00000514368.1 | 0.029 | 0.335 |
| ENST00000451607.1 | 0.029 | 0.252 |
| ENST00000435580.1 | 0.030 | 0.343 |
| ENST00000429230.1 | 0.030 | 0.213 |
| ENST00000426716.1 | 0.031 | 3.178 |
| ENST00000510261.1 | 0.031 | 4.086 |
| ENST00000599448.1 | 0.032 | 0.324 |
| ENST00000436121.1 | 0.033 | 2.086 |
| ENST00000600693.1 | 0.036 | 0.359 |
| ENST00000521819.1 | 0.036 | 0.195 |
| ENST00000508968.1 | 0.036 | 0.314 |
| ENST00000598349.1 | 0.037 | 2.579 |
| ENST00000453568.1 | 0.037 | 0.410 |
| ENST00000443800.1 | 0.037 | 0.396 |
| ENST00000435023.1 | 0.037 | 0.487 |
| ENST00000431569.1 | 0.038 | 3.721 |
| ENST00000439893.1 | 0.038 | 0.390 |
| ENST00000508847.1 | 0.038 | 0.256 |
| ENST00000587568.1 | 0.040 | 3.573 |
| ENST00000418620.1 | 0.041 | 0.248 |
| ENST00000509497.1 | 0.041 | 0.337 |
| ENST00000527035.1 | 0.042 | 0.369 |
| ENST00000498480.1 | 0.042 | 0.447 |
| ENST00000415629.2 | 0.043 | 0.145 |
| ENST00000514661.1 | 0.044 | 2.482 |
| ENST00000465215.1 | 0.046 | 0.179 |
| ENST00000416453.2 | 0.048 | 2.769 |
| ENST00000505339.1 | 0.048 | 3.529 |

TABLE 37

List of 369 lncRNA from Gencode database which are differentially expressed (p < 0.05) and/or have an AUC > 0.7 or < 0.3 between the low LVEF group (LVEF ≤ 45%) and the high LVEF group (LVEF > 45%)

| lncRNA | p Value | auc | lncRNA | p Value | auc | lncRNA | p Value | auc |
|---|---|---|---|---|---|---|---|---|
| ENST00000437488.1 | 0.000 | 0.147 | ENST00000450746.1 | 0.023 | 0.707 | ENST00000607541.1 | 0.045 | 0.293 |
| ENST00000441790.1 | 0.000 | 0.862 | ENST00000456687.3 | 0.023 | 0.267 | ENST00000432386.1 | 0.045 | 0.298 |
| ENST00000587085.1 | 0.000 | 0.849 | ENST00000609354.1 | 0.024 | 0.716 | ENST00000508799.1 | 0.045 | 0.284 |
| ENST00000451711.1 | 0.001 | 0.156 | ENST00000515405.1 | 0.024 | 0.249 | ENST00000605698.1 | 0.045 | 0.311 |
| ENST00000507236.1 | 0.001 | 0.164 | ENST00000432978.1 | 0.024 | 0.258 | ENST00000399543.1 | 0.045 | 0.262 |
| ENST00000513955.1 | 0.001 | 0.849 | ENST00000452809.1 | 0.024 | 0.698 | ENST00000513540.1 | 0.045 | 0.733 |
| ENST00000505848.1 | 0.001 | 0.173 | ENST00000417795.1 | 0.025 | 0.284 | ENST00000427819.1 | 0.046 | 0.716 |
| ENST00000598757.1 | 0.001 | 0.191 | ENST00000509999.1 | 0.025 | 0.713 | ENST00000509548.2 | 0.046 | 0.676 |
| ENST00000417926.1 | 0.001 | 0.867 | ENST00000553319.1 | 0.025 | 0.276 | ENST00000424689.1 | 0.046 | 0.298 |
| ENST00000441053.1 | 0.001 | 0.209 | ENST00000441272.2 | 0.025 | 0.271 | ENST00000465215.1 | 0.046 | 0.458 |
| ENST00000444037.1 | 0.002 | 0.187 | ENST00000445180.2 | 0.026 | 0.284 | ENST00000512637.1 | 0.046 | 0.311 |
| ENST00000509416.1 | 0.002 | 0.844 | ENST00000452840.1 | 0.026 | 0.724 | ENST00000436207.2 | 0.046 | 0.771 |
| ENST00000435552.1 | 0.002 | 0.191 | ENST00000515153.1 | 0.026 | 0.244 | ENST00000508696.1 | 0.046 | 0.711 |
| ENST00000416930.2 | 0.002 | 0.213 | ENST00000606696.1 | 0.026 | 0.733 | ENST00000609881.1 | 0.046 | 0.298 |
| ENST00000438158.1 | 0.003 | 0.200 | ENST00000515184.1 | 0.026 | 0.280 | ENST00000515243.1 | 0.046 | 0.276 |
| ENST00000565044.1 | 0.003 | 0.196 | ENST00000596887.1 | 0.027 | 0.769 | ENST00000438414.1 | 0.047 | 0.338 |
| ENST00000451894.2 | 0.003 | 0.796 | ENST00000450944.1 | 0.027 | 0.271 | ENST00000458007.2 | 0.047 | 0.271 |
| ENST00000477805.1 | 0.003 | 0.222 | ENST00000510935.1 | 0.027 | 0.284 | ENST00000424748.1 | 0.047 | 0.293 |
| ENST00000450713.1 | 0.003 | 0.800 | ENST00000565538.1 | 0.027 | 0.800 | ENST00000508959.1 | 0.047 | 0.302 |
| ENST00000562054.1 | 0.004 | 0.191 | ENST00000517934.1 | 0.027 | 0.284 | ENST00000596329.1 | 0.047 | 0.364 |

TABLE 37-continued

List of 369 lncRNA from Gencode database which are differentially expressed (p < 0.05) and/or have an
AUC > 0.7 or < 0.3 between the low LVEF group (LVEF ≤ 45%) and the high LVEF group (LVEF > 45%)

| lncRNA | p Value | auc | lncRNA | p Value | auc | lncRNA | p Value | auc |
|---|---|---|---|---|---|---|---|---|
| ENST00000412228.1 | 0.004 | 0.227 | ENST00000569860.1 | 0.027 | 0.742 | ENST00000446521.1 | 0.048 | 0.284 |
| ENST00000417324.1 | 0.004 | 0.209 | ENST00000415628.1 | 0.027 | 0.293 | ENST00000512965.1 | 0.048 | 0.704 |
| ENST00000513767.3 | 0.004 | 0.178 | ENST00000607831.1 | 0.027 | 0.258 | ENST00000416453.2 | 0.048 | 0.658 |
| ENST00000502757.1 | 0.004 | 0.804 | ENST00000594798.1 | 0.027 | 0.271 | ENST00000505339.1 | 0.048 | 0.578 |
| ENST00000608574.1 | 0.004 | 0.200 | ENST00000497573.1 | 0.028 | 0.253 | ENST00000417563.1 | 0.049 | 0.713 |
| ENST00000456026.1 | 0.005 | 0.756 | ENST00000416689.1 | 0.028 | 0.249 | ENST00000440322.1 | 0.049 | 0.716 |
| ENST00000609549.1 | 0.005 | 0.276 | ENST00000507424.1 | 0.028 | 0.293 | ENST00000596632.1 | 0.049 | 0.298 |
| ENST00000608077.1 | 0.005 | 0.253 | ENST00000566527.1 | 0.028 | 0.720 | ENST00000451289.1 | 0.049 | 0.716 |
| ENST00000589496.2 | 0.005 | 0.782 | ENST00000590186.1 | 0.028 | 0.236 | ENST00000437267.2 | 0.049 | 0.276 |
| ENST00000568384.1 | 0.005 | 0.213 | ENST00000510632.1 | 0.028 | 0.298 | ENST00000520443.1 | 0.049 | 0.671 |
| ENST00000440371.1 | 0.005 | 0.236 | ENST00000429352.1 | 0.028 | 0.280 | ENST00000523648.1 | 0.049 | 0.316 |
| ENST00000366187.2 | 0.005 | 0.791 | ENST00000510175.1 | 0.029 | 0.738 | ENST00000449140.2 | 0.049 | 0.284 |
| ENST00000607068.1 | 0.006 | 0.213 | ENST00000514368.1 | 0.029 | 0.304 | ENST00000594351.1 | 0.051 | 0.293 |
| ENST00000519929.1 | 0.006 | 0.213 | ENST00000451607.1 | 0.029 | 0.244 | ENST00000506660.1 | 0.051 | 0.293 |
| ENST00000504246.1 | 0.006 | 0.209 | ENST00000448786.1 | 0.030 | 0.700 | ENST00000608881.1 | 0.051 | 0.711 |
| ENST00000515286.1 | 0.006 | 0.218 | ENST00000435580.1 | 0.030 | 0.320 | ENST00000463978.1 | 0.051 | 0.720 |
| ENST00000427825.1 | 0.006 | 0.236 | ENST00000429230.1 | 0.030 | 0.236 | ENST00000507782.1 | 0.051 | 0.293 |
| ENST00000412294.1 | 0.006 | 0.778 | ENST00000508752.1 | 0.030 | 0.707 | ENST00000436475.2 | 0.051 | 0.720 |
| ENST00000512882.2 | 0.007 | 0.791 | ENST00000426716.1 | 0.031 | 0.713 | ENST00000512464.1 | 0.052 | 0.720 |
| ENST00000424246.1 | 0.007 | 0.769 | ENST00000423600.1 | 0.031 | 0.271 | ENST00000599387.1 | 0.052 | 0.702 |
| ENST00000457815.1 | 0.007 | 0.769 | ENST00000417976.1 | 0.031 | 0.707 | ENST00000441587.2 | 0.052 | 0.716 |
| ENST00000512458.1 | 0.007 | 0.251 | ENST00000510261.1 | 0.031 | 0.711 | ENST00000504765.1 | 0.052 | 0.716 |
| ENST00000510795.1 | 0.007 | 0.791 | ENST00000442864.1 | 0.031 | 0.698 | ENST00000430542.1 | 0.053 | 0.720 |
| ENST00000422038.1 | 0.007 | 0.756 | ENST00000442956.1 | 0.031 | 0.276 | ENST00000549744.1 | 0.053 | 0.284 |
| ENST00000428156.1 | 0.007 | 0.813 | ENST00000458698.2 | 0.031 | 0.284 | ENST00000441459.1 | 0.053 | 0.298 |
| ENST00000514724.2 | 0.007 | 0.267 | ENST00000506305.1 | 0.032 | 0.280 | ENST00000453988.1 | 0.055 | 0.249 |
| ENST00000418602.1 | 0.008 | 0.244 | ENST00000599448.1 | 0.032 | 0.258 | ENST00000414634.1 | 0.056 | 0.278 |
| ENST00000506892.1 | 0.008 | 0.258 | ENST00000505347.1 | 0.032 | 0.293 | ENST00000515842.1 | 0.056 | 0.289 |
| ENST00000513219.1 | 0.008 | 0.240 | ENST00000436121.1 | 0.033 | 0.760 | ENST00000456897.1 | 0.057 | 0.284 |
| ENST00000420365.1 | 0.008 | 0.249 | ENST00000606217.1 | 0.033 | 0.284 | ENST00000449673.1 | 0.057 | 0.276 |
| ENST00000602528.1 | 0.009 | 0.778 | ENST00000608360.1 | 0.033 | 0.298 | ENST00000511091.1 | 0.057 | 0.702 |
| ENST00000430666.1 | 0.009 | 0.218 | ENST00000439024.1 | 0.033 | 0.667 | ENST00000449783.1 | 0.057 | 0.733 |
| ENST00000508486.2 | 0.009 | 0.773 | ENST00000414030.1 | 0.033 | 0.276 | ENST00000414938.1 | 0.058 | 0.253 |
| ENST00000607216.1 | 0.010 | 0.227 | ENST00000437798.1 | 0.034 | 0.329 | ENST00000515811.1 | 0.058 | 0.716 |
| ENST00000456255.1 | 0.010 | 0.233 | ENST00000449845.1 | 0.034 | 0.284 | ENST00000589853.1 | 0.060 | 0.711 |
| ENST00000424895.1 | 0.011 | 0.747 | ENST00000566840.1 | 0.034 | 0.262 | ENST00000476125.1 | 0.061 | 0.707 |
| ENST00000565428.1 | 0.011 | 0.258 | ENST00000460574.1 | 0.034 | 0.280 | ENST00000451992.2 | 0.062 | 0.262 |
| ENST00000503037.1 | 0.011 | 0.240 | ENST00000438553.1 | 0.034 | 0.729 | ENST00000562191.1 | 0.062 | 0.724 |
| ENST00000503929.1 | 0.011 | 0.773 | ENST00000605571.1 | 0.034 | 0.267 | ENST00000505572.1 | 0.062 | 0.716 |
| ENST00000427732.1 | 0.011 | 0.769 | ENST00000439186.1 | 0.034 | 0.727 | ENST00000434572.1 | 0.062 | 0.262 |
| ENST00000427804.1 | 0.011 | 0.209 | ENST00000412369.1 | 0.034 | 0.298 | ENST00000454348.1 | 0.064 | 0.271 |
| ENST00000506292.2 | 0.011 | 0.244 | ENST00000412483.1 | 0.035 | 0.262 | ENST00000482609.1 | 0.064 | 0.262 |
| ENST00000452738.1 | 0.011 | 0.738 | ENST00000607830.1 | 0.035 | 0.284 | ENST00000511241.1 | 0.064 | 0.213 |
| ENST00000420549.1 | 0.012 | 0.804 | ENST00000505348.1 | 0.035 | 0.729 | ENST00000504263.1 | 0.070 | 0.716 |
| ENST00000445523.1 | 0.012 | 0.769 | ENST00000600693.1 | 0.036 | 0.267 | ENST00000418925.1 | 0.071 | 0.298 |
| ENST00000357876.5 | 0.012 | 0.249 | ENST00000438002.1 | 0.036 | 0.293 | ENST00000417482.1 | 0.071 | 0.271 |
| ENST00000513572.1 | 0.012 | 0.751 | ENST00000431435.1 | 0.036 | 0.716 | ENST00000514265.1 | 0.072 | 0.742 |
| ENST00000443613.2 | 0.012 | 0.240 | ENST00000521819.1 | 0.036 | 0.331 | ENST00000467438.1 | 0.072 | 0.244 |
| ENST00000600062.1 | 0.012 | 0.764 | ENST00000569502.1 | 0.036 | 0.293 | ENST00000608069.1 | 0.073 | 0.711 |
| ENST00000479610.1 | 0.012 | 0.267 | ENST00000508968.1 | 0.036 | 0.287 | ENST00000587696.1 | 0.076 | 0.293 |
| ENST00000588108.1 | 0.013 | 0.200 | ENST00000413304.2 | 0.037 | 0.320 | ENST00000609583.1 | 0.076 | 0.300 |
| ENST00000446139.1 | 0.013 | 0.791 | ENST00000562952.1 | 0.037 | 0.724 | ENST00000446411.1 | 0.076 | 0.738 |
| ENST00000510381.2 | 0.013 | 0.773 | ENST00000598349.1 | 0.037 | 0.649 | ENST00000443093.2 | 0.077 | 0.253 |
| ENST00000514877.1 | 0.013 | 0.233 | ENST00000453568.1 | 0.037 | 0.280 | ENST00000431759.1 | 0.077 | 0.289 |
| ENST00000426551.1 | 0.013 | 0.284 | ENST00000482019.1 | 0.037 | 0.324 | ENST00000418387.1 | 0.078 | 0.733 |
| ENST00000507361.1 | 0.013 | 0.244 | ENST00000418244.1 | 0.037 | 0.269 | ENST00000419609.1 | 0.079 | 0.716 |
| ENST00000504046.1 | 0.013 | 0.769 | ENST00000443800.1 | 0.037 | 0.271 | ENST00000466225.2 | 0.079 | 0.280 |
| ENST00000462431.1 | 0.013 | 0.787 | ENST00000435023.1 | 0.037 | 0.307 | ENST00000513926.1 | 0.081 | 0.298 |
| ENST00000491676.1 | 0.013 | 0.244 | ENST00000440545.1 | 0.037 | 0.724 | ENST00000437631.1 | 0.082 | 0.760 |
| ENST00000440516.1 | 0.013 | 0.764 | ENST00000452509.1 | 0.037 | 0.724 | ENST00000430520.1 | 0.082 | 0.296 |
| ENST00000609900.1 | 0.014 | 0.800 | ENST00000431569.1 | 0.038 | 0.611 | ENST00000506852.1 | 0.084 | 0.751 |
| ENST00000589150.1 | 0.014 | 0.258 | ENST00000439893.1 | 0.038 | 0.187 | ENST00000510753.1 | 0.085 | 0.707 |
| ENST00000596829.1 | 0.014 | 0.227 | ENST00000508847.1 | 0.038 | 0.311 | ENST00000447389.1 | 0.089 | 0.716 |
| ENST00000601955.1 | 0.014 | 0.271 | ENST00000453128.1 | 0.039 | 0.267 | ENST00000436262.1 | 0.091 | 0.271 |
| ENST00000608482.1 | 0.015 | 0.244 | ENST00000458254.1 | 0.039 | 0.267 | ENST00000496242.1 | 0.091 | 0.280 |
| ENST00000457489.1 | 0.015 | 0.747 | ENST00000594189.1 | 0.039 | 0.253 | ENST00000453324.1 | 0.092 | 0.280 |
| ENST00000422996.1 | 0.015 | 0.249 | ENST00000502934.1 | 0.040 | 0.711 | ENST00000602108.1 | 0.096 | 0.267 |
| ENST00000495228.1 | 0.015 | 0.253 | ENST00000587568.1 | 0.040 | 0.720 | ENST00000505538.1 | 0.099 | 0.298 |
| ENST00000477539.2 | 0.016 | 0.756 | ENST00000431985.1 | 0.040 | 0.302 | ENST00000606056.1 | 0.101 | 0.280 |
| ENST00000503616.1 | 0.016 | 0.262 | ENST00000507344.1 | 0.040 | 0.738 | ENST00000508719.1 | 0.102 | 0.702 |
| ENST00000587306.1 | 0.016 | 0.244 | ENST00000471990.2 | 0.041 | 0.702 | ENST00000512370.1 | 0.107 | 0.271 |
| ENST00000608123.1 | 0.016 | 0.267 | ENST00000597543.1 | 0.041 | 0.702 | ENST00000427421.1 | 0.107 | 0.293 |
| ENST00000439878.1 | 0.017 | 0.238 | ENST00000418620.1 | 0.041 | 0.302 | ENST00000609097.1 | 0.108 | 0.711 |
| ENST00000607002.1 | 0.017 | 0.249 | ENST00000443205.1 | 0.041 | 0.684 | ENST00000602433.1 | 0.116 | 0.720 |
| ENST00000466291.1 | 0.017 | 0.747 | ENST00000483840.1 | 0.041 | 0.716 | ENST00000512090.1 | 0.117 | 0.298 |

TABLE 37-continued

List of 369 lncRNA from Gencode database which are differentially expressed (p < 0.05) and/or have an
AUC > 0.7 or < 0.3 between the low LVEF group (LVEF ≤ 45%) and the high LVEF group (LVEF > 45%)

| lncRNA | p Value | auc | lncRNA | p Value | auc | lncRNA | p Value | auc |
|---|---|---|---|---|---|---|---|---|
| ENST00000424244.1 | 0.018 | 0.253 | ENST00000509497.1 | 0.041 | 0.302 | ENST00000588944.1 | 0.118 | 0.702 |
| ENST00000455929.1 | 0.018 | 0.796 | ENST00000412134.1 | 0.042 | 0.742 | ENST00000426519.1 | 0.119 | 0.716 |
| ENST00000512417.1 | 0.018 | 0.284 | ENST00000511517.1 | 0.042 | 0.311 | ENST00000506454.1 | 0.121 | 0.720 |
| ENST00000506068.1 | 0.018 | 0.769 | ENST00000503267.1 | 0.042 | 0.311 | ENST00000515337.1 | 0.126 | 0.271 |
| ENST00000431650.1 | 0.018 | 0.276 | ENST00000607662.1 | 0.042 | 0.724 | ENST00000505371.2 | 0.127 | 0.296 |
| ENST00000607723.1 | 0.018 | 0.773 | ENST00000507517.1 | 0.042 | 0.307 | ENST00000503685.1 | 0.131 | 0.289 |
| ENST00000417765.1 | 0.019 | 0.742 | ENST00000527035.1 | 0.042 | 0.282 | ENST00000503163.1 | 0.132 | 0.271 |
| ENST00000607540.1 | 0.019 | 0.747 | ENST00000498480.1 | 0.042 | 0.276 | ENST00000504829.1 | 0.136 | 0.707 |
| ENST00000502467.1 | 0.019 | 0.693 | ENST00000507251.1 | 0.042 | 0.711 | ENST00000431856.1 | 0.136 | 0.716 |
| ENST00000589024.1 | 0.019 | 0.738 | ENST00000417651.1 | 0.042 | 0.280 | ENST00000607164.1 | 0.138 | 0.738 |
| ENST00000433219.1 | 0.019 | 0.276 | ENST00000415629.2 | 0.043 | 0.333 | ENST00000503113.1 | 0.141 | 0.293 |
| ENST00000426881.2 | 0.019 | 0.258 | ENST00000417805.1 | 0.043 | 0.711 | ENST00000503320.1 | 0.150 | 0.298 |
| ENST00000443928.2 | 0.019 | 0.244 | ENST00000606069.1 | 0.043 | 0.298 | ENST00000356684.3 | 0.156 | 0.702 |
| ENST00000567904.1 | 0.020 | 0.258 | ENST00000431362.1 | 0.043 | 0.253 | ENST00000565748.1 | 0.156 | 0.702 |
| ENST00000439479.1 | 0.020 | 0.276 | ENST00000610091.1 | 0.043 | 0.729 | ENST00000423921.1 | 0.158 | 0.276 |
| ENST00000473001.1 | 0.020 | 0.276 | ENST00000515422.1 | 0.044 | 0.698 | ENST00000462835.1 | 0.158 | 0.289 |
| ENST00000429666.1 | 0.020 | 0.247 | ENST00000514661.1 | 0.044 | 0.644 | ENST00000512185.1 | 0.158 | 0.298 |
| ENST00000421498.1 | 0.021 | 0.676 | ENST00000608605.1 | 0.044 | 0.311 | ENST00000513591.1 | 0.162 | 0.298 |
| ENST00000455038.1 | 0.021 | 0.280 | ENST00000414625.2 | 0.044 | 0.316 | ENST00000366278.2 | 0.165 | 0.711 |
| ENST00000433175.2 | 0.022 | 0.267 | ENST00000514600.1 | 0.044 | 0.787 | ENST00000505018.1 | 0.166 | 0.760 |
| ENST00000451101.1 | 0.022 | 0.267 | ENST00000416209.2 | 0.044 | 0.293 | ENST00000453370.1 | 0.166 | 0.716 |
| ENST00000608777.1 | 0.022 | 0.267 | ENST00000597366.1 | 0.044 | 0.707 | ENST00000502100.2 | 0.178 | 0.289 |
| ENST00000602919.1 | 0.022 | 0.253 | ENST00000417695.1 | 0.044 | 0.293 | ENST00000416221.1 | 0.190 | 0.720 |
| ENST00000507011.1 | 0.022 | 0.242 | ENST00000448901.1 | 0.044 | 0.760 | ENST00000596220.1 | 0.195 | 0.267 |
| ENST00000360083.3 | 0.022 | 0.760 | ENST00000424612.1 | 0.045 | 0.311 | ENST00000593876.1 | 0.291 | 0.742 |
| ENST00000420272.2 | 0.022 | 0.280 | ENST00000606287.1 | 0.045 | 0.289 | ENST00000602972.1 | 0.335 | 0.284 |
| ENST00000507932.1 | 0.022 | 0.298 | ENST00000607594.1 | 0.045 | 0.689 | ENST00000456146.1 | 0.346 | 0.718 |
| ENST00000417644.1 | 0.023 | 0.258 | ENST00000367716.3 | 0.045 | 0.293 | ENST00000607769.1 | 0.539 | 0.293 |

First, samples are grouped into 2 groups by a dichotomized variable: 1-month LVEF<40% and 1-month LVEF>40%.

273 lncRNA are differentially expressed and among these, 83 lncRNA are differentially expressed and have a fold change>2 or <0.5 between the low LVEF (LVEF≤40%) and the high LVEF (LVEF>40%). 3 lncRNAs are common to D3 samples (ENST00000421563.1, ENST00000443562.1, ENST00000455988.1). The p-value and the fold-change of these lncRNA are listed in the Table 38. In Table 39, 235 lncRNAs which have a p<0.05 and an individual AUC>0.7 or <0.3 are listed in Table 39.

TABLE 38

List of 83 lncRNA from Gencode database which are
differentially expressed (p < 0.05) and
have a fold change >2 or <0.5 between the low
LVEF group (LVEF ≤ 40%) and the
high LVEF group (LVEF > 40%)

| lncRNA | p Value | fold change |
|---|---|---|
| ENST00000510165.1 | 0.000 | 0.454 |
| ENST00000449154.1 | 0.001 | 3.668 |
| ENST00000523354.1 | 0.001 | 2.383 |
| ENST00000598798.1 | 0.001 | 3.678 |
| ENST00000421563.1 | 0.001 | 2.688 |
| ENST00000513851.1 | 0.002 | 2.445 |
| ENST00000515842.1 | 0.002 | 0.453 |
| ENST00000508845.1 | 0.004 | 2.084 |
| ENST00000506338.1 | 0.004 | 3.476 |
| ENST00000453015.1 | 0.006 | 0.491 |
| ENST00000505997.1 | 0.006 | 12.552 |
| ENST00000507435.1 | 0.007 | 4.142 |
| ENST00000504368.1 | 0.007 | 2.362 |
| ENST00000420672.1 | 0.008 | 7.02E+28 |
| ENST00000504165.1 | 0.008 | 2.796 |
| ENST00000412311.1 | 0.009 | 6.569 |
| ENST00000454183.1 | 0.009 | 4.501 |
| ENST00000422253.1 | 0.010 | 3.571 |

TABLE 38-continued

List of 83 lncRNA from Gencode database which are
differentially expressed (p < 0.05) and
have a fold change >2 or <0.5 between the low
LVEF group (LVEF ≤ 40%) and the
high LVEF group (LVEF > 40%)

| lncRNA | p Value | fold change |
|---|---|---|
| ENST00000490497.1 | 0.011 | 6.17E+13 |
| ENST00000402410.2 | 0.011 | 9.911 |
| ENST00000513660.2 | 0.012 | 3.751 |
| ENST00000511222.1 | 0.012 | 2.305 |
| ENST00000439239.2 | 0.013 | 2.069 |
| ENST00000549878.1 | 0.013 | 2.466 |
| ENST00000444217.1 | 0.013 | 2.075 |
| ENST00000435548.1 | 0.014 | 5.647 |
| ENST00000607026.1 | 0.014 | 0.480 |
| ENST00000515111.1 | 0.048 | 2.667 |
| ENST00000503093.1 | 0.014 | 4.916 |
| ENST00000443670.1 | 0.014 | 2.095 |
| ENST00000429608.1 | 0.015 | 2.188 |
| ENST00000518276.1 | 0.016 | 2.734 |
| ENST00000420418.1 | 0.016 | 4.067 |
| ENST00000511419.1 | 0.017 | 3.308 |
| ENST00000431130.2 | 0.017 | 2.765 |
| ENST00000412171.2 | 0.020 | 988.115 |
| ENST00000419531.2 | 0.021 | 0.003 |
| ENST00000442384.1 | 0.022 | 2.042 |
| ENST00000446102.1 | 0.022 | 0.481 |
| ENST00000414102.1 | 0.022 | 0.365 |
| ENST00000507963.1 | 0.022 | 4.620 |
| ENST00000609843.1 | 0.024 | 2.273 |
| ENST00000449124.1 | 0.025 | 3.322 |
| ENST00000425192.1 | 0.025 | 2.64E+12 |
| ENST00000514377.1 | 0.025 | 4.851 |
| ENST00000515680.2 | 0.027 | 2.330 |
| ENST00000423168.1 | 0.028 | 4.270 |
| ENST00000429230.1 | 0.028 | 3.757 |
| ENST00000604660.1 | 0.029 | 2.349 |
| ENST00000421298.1 | 0.029 | 3.474 |
| ENST00000492209.1 | 0.030 | 2.082 |

TABLE 38-continued

List of 83 lncRNA from Gencode database which are differentially expressed (p < 0.05) and have a fold change >2 or <0.5 between the low LVEF group (LVEF ≤ 40%) and the high LVEF group (LVEF > 40%)

| lncRNA | p Value | fold change |
|---|---|---|
| ENST00000523311.1 | 0.031 | 2.078 |
| ENST00000434796.1 | 0.031 | 2.290 |
| ENST00000447876.1 | 0.031 | 0.287 |
| ENST00000576302.1 | 0.032 | 3.094 |
| ENST00000457686.1 | 0.049 | 0.231 |
| ENST00000588145.1 | 0.032 | 13.047 |
| ENST00000602470.1 | 0.032 | 2.968 |
| ENST00000497379.2 | 0.033 | 0.330 |
| ENST00000506100.1 | 0.033 | 2.451 |
| ENST00000609352.1 | 0.034 | 2.228 |
| ENST00000507476.1 | 0.034 | 3.547 |
| ENST00000415202.1 | 0.035 | 6.887 |
| ENST00000599781.1 | 0.036 | 0.075 |
| ENST00000497551.2 | 0.037 | 2.235 |
| ENST00000597654.1 | 0.037 | 0.037 |
| ENST00000439606.1 | 0.038 | 7.846 |
| ENST00000455988.1 | 0.038 | 2.302 |
| ENST00000597904.1 | 0.039 | 2.634 |
| ENST00000505972.2 | 0.039 | 0.466 |
| ENST00000609140.1 | 0.040 | 68.930 |
| ENST00000443284.1 | 0.041 | 2.225 |
| ENST00000502812.2 | 0.042 | 0.359 |
| ENST00000552026.1 | 0.043 | 2.692 |
| ENST00000522300.1 | 0.043 | 0.468 |
| ENST00000440038.2 | 0.044 | 7.706 |
| ENST00000413841.1 | 0.044 | 2.153 |
| ENST00000443562.1 | 0.044 | 2.013 |
| ENST00000457941.1 | 0.045 | 17.472 |
| ENST00000605147.1 | 0.046 | 0.409 |
| ENST00000456803.1 | 0.047 | 0.465 |
| ENST00000578974.2 | 0.048 | 0.387 |
| ENST00000509212.1 | 0.048 | 0.492 |

TABLE 39

List of 235 lncRNA from Gencode database, which are differentially expressed (p < 0.05) and have an AUC > 0.7 or < 0.3 between the low LVEF group (LVEF ≤ 40%) and the high LVEF group (LVEF > 40%)

| lncRNA | p Value | auc | lncRNA | p Value | auc | lncRNA | p Value | auc |
|---|---|---|---|---|---|---|---|---|
| ENST00000510165.1 | 0.000 | 0.034 | ENST00000496154.2 | 0.017 | 0.179 | ENST00000608777.1 | 0.035 | 0.231 |
| ENST00000431244.1 | 0.001 | 0.085 | ENST00000511419.1 | 0.017 | 0.761 | ENST00000499292.2 | 0.035 | 0.162 |
| ENST00000449154.1 | 0.001 | 0.868 | ENST00000431130.2 | 0.017 | 0.765 | ENST00000415202.1 | 0.035 | 0.821 |
| ENST00000414199.1 | 0.001 | 0.880 | ENST00000487657.2 | 0.017 | 0.786 | ENST00000610144.1 | 0.035 | 0.231 |
| ENST00000523354.1 | 0.001 | 0.829 | ENST00000514241.1 | 0.017 | 0.214 | ENST00000515188.1 | 0.035 | 0.778 |
| ENST00000454595.1 | 0.001 | 0.863 | ENST00000604571.1 | 0.017 | 0.162 | ENST00000599781.1 | 0.036 | 0.111 |
| ENST00000598798.1 | 0.001 | 0.859 | ENST00000428624.1 | 0.018 | 0.162 | ENST00000497551.2 | 0.037 | 0.726 |
| ENST00000421563.1 | 0.001 | 0.872 | ENST00000592948.1 | 0.018 | 0.222 | ENST00000597654.1 | 0.037 | 0.188 |
| ENST00000417926.1 | 0.001 | 0.863 | ENST00000418335.1 | 0.018 | 0.171 | ENST00000505364.1 | 0.037 | 0.744 |
| ENST00000513851.1 | 0.002 | 0.863 | ENST00000435895.1 | 0.018 | 0.171 | ENST00000514427.1 | 0.038 | 0.265 |
| ENST00000515842.1 | 0.002 | 0.094 | ENST00000322353.3 | 0.019 | 0.744 | ENST00000604680.1 | 0.038 | 0.752 |
| ENST00000444672.1 | 0.002 | 0.880 | ENST00000512464.1 | 0.019 | 0.803 | ENST00000512546.1 | 0.038 | 0.239 |
| ENST00000420071.1 | 0.002 | 0.880 | ENST00000448713.1 | 0.019 | 0.778 | ENST00000455988.1 | 0.038 | 0.786 |
| ENST00000420350.1 | 0.002 | 0.128 | ENST00000467240.1 | 0.019 | 0.786 | ENST00000597904.1 | 0.039 | 0.752 |
| ENST00000512417.1 | 0.003 | 0.855 | ENST00000444647.1 | 0.019 | 0.239 | ENST00000505972.2 | 0.039 | 0.248 |
| ENST00000608111.1 | 0.004 | 0.846 | ENST00000425974.1 | 0.020 | 0.769 | ENST00000512873.1 | 0.039 | 0.761 |
| ENST00000508845.1 | 0.004 | 0.829 | ENST00000452176.1 | 0.020 | 0.778 | ENST00000607459.1 | 0.039 | 0.231 |
| ENST00000506338.1 | 0.004 | 0.803 | ENST00000510416.1 | 0.020 | 0.761 | ENST00000584829.1 | 0.039 | 0.744 |
| ENST00000430897.1 | 0.004 | 0.162 | ENST00000503188.1 | 0.020 | 0.197 | ENST00000471626.1 | 0.039 | 0.718 |
| ENST00000601136.1 | 0.005 | 0.872 | ENST00000509559.1 | 0.021 | 0.188 | ENST00000514265.1 | 0.039 | 0.231 |
| ENST00000430520.1 | 0.005 | 0.137 | ENST00000508255.1 | 0.021 | 0.214 | ENST00000451362.1 | 0.039 | 0.265 |
| ENST00000522312.1 | 0.005 | 0.137 | ENST00000419531.2 | 0.021 | 0.128 | ENST00000595232.1 | 0.039 | 0.214 |
| ENST00000451396.2 | 0.005 | 0.838 | ENST00000430471.1 | 0.021 | 0.786 | ENST00000473798.1 | 0.039 | 0.769 |
| ENST00000453015.1 | 0.006 | 0.179 | ENST00000442384.1 | 0.022 | 0.761 | ENST00000427748.1 | 0.040 | 0.239 |
| ENST00000397645.2 | 0.006 | 0.838 | ENST00000446102.1 | 0.022 | 0.188 | ENST00000607389.1 | 0.040 | 0.769 |
| ENST00000449586.1 | 0.006 | 0.821 | ENST00000414102.1 | 0.022 | 0.179 | ENST00000602316.1 | 0.040 | 0.197 |
| ENST00000356684.3 | 0.006 | 0.162 | ENST00000428651.1 | 0.022 | 0.231 | ENST00000439601.1 | 0.040 | 0.205 |
| ENST00000505997.1 | 0.006 | 0.761 | ENST00000507963.1 | 0.022 | 0.726 | ENST00000462176.2 | 0.040 | 0.248 |
| ENST00000508619.1 | 0.007 | 0.829 | ENST00000473595.1 | 0.023 | 0.761 | ENST00000512519.1 | 0.040 | 0.197 |
| ENST00000507435.1 | 0.007 | 0.786 | ENST00000326734.1 | 0.023 | 0.256 | ENST00000609140.1 | 0.040 | 0.752 |
| ENST00000510254.1 | 0.007 | 0.197 | ENST00000435692.2 | 0.023 | 0.863 | ENST00000512527.1 | 0.041 | 0.239 |
| ENST00000440104.1 | 0.007 | 0.829 | ENST00000513812.1 | 0.023 | 0.726 | ENST00000514010.1 | 0.041 | 0.726 |
| ENST00000504368.1 | 0.007 | 0.786 | ENST00000609843.1 | 0.024 | 0.752 | ENST00000444043.2 | 0.041 | 0.726 |
| ENST00000438506.1 | 0.008 | 0.829 | ENST00000449124.1 | 0.025 | 0.795 | ENST00000429871.1 | 0.041 | 0.291 |
| ENST00000420672.1 | 0.008 | 0.859 | ENST00000433108.1 | 0.025 | 0.778 | ENST00000443284.1 | 0.041 | 0.795 |
| ENST00000412313.1 | 0.008 | 0.128 | ENST00000425192.1 | 0.025 | 0.726 | ENST00000461448.1 | 0.041 | 0.231 |
| ENST00000504165.1 | 0.008 | 0.803 | ENST00000514377.1 | 0.025 | 0.752 | ENST00000609969.1 | 0.041 | 0.769 |
| ENST00000511234.1 | 0.008 | 0.179 | ENST00000444346.1 | 0.025 | 0.239 | ENST00000458097.1 | 0.041 | 0.222 |
| ENST00000510879.1 | 0.009 | 0.872 | ENST00000513770.1 | 0.026 | 0.778 | ENST00000446073.1 | 0.042 | 0.769 |
| ENST00000412311.1 | 0.009 | 0.722 | ENST00000448431.1 | 0.026 | 0.214 | ENST00000431691.1 | 0.042 | 0.752 |
| ENST00000439795.1 | 0.009 | 0.222 | ENST00000440404.1 | 0.026 | 0.197 | ENST00000502812.2 | 0.042 | 0.239 |
| ENST00000434094.1 | 0.009 | 0.179 | ENST00000560688.1 | 0.026 | 0.248 | ENST00000508470.1 | 0.043 | 0.761 |
| ENST00000454183.1 | 0.009 | 0.774 | ENST00000428176.1 | 0.026 | 0.248 | ENST00000552026.1 | 0.043 | 0.735 |
| ENST00000504207.1 | 0.009 | 0.179 | ENST00000515680.2 | 0.027 | 0.765 | ENST00000458007.2 | 0.043 | 0.256 |
| ENST00000504297.1 | 0.010 | 0.846 | ENST00000446136.1 | 0.027 | 0.769 | ENST00000522300.1 | 0.043 | 0.248 |

TABLE 39-continued

List of 235 lncRNA from Gencode database, which are differentially expressed (p < 0.05) and have an AUC > 0.7 or < 0.3 between the low LVEF group (LVEF ≤ 40%) and the high LVEF group (LVEF > 40%)

| lncRNA | p Value | auc | lncRNA | p Value | auc | lncRNA | p Value | auc |
|---|---|---|---|---|---|---|---|---|
| ENST00000503568.1 | 0.010 | 0.821 | ENST00000511279.1 | 0.028 | 0.752 | ENST00000366441.2 | 0.043 | 0.795 |
| ENST00000412357.1 | 0.010 | 0.803 | ENST00000423168.1 | 0.028 | 0.838 | ENST00000429269.1 | 0.043 | 0.778 |
| ENST00000460597.1 | 0.010 | 0.821 | ENST00000429230.1 | 0.028 | 0.744 | ENST00000595268.1 | 0.044 | 0.744 |
| ENST00000422253.1 | 0.010 | 0.803 | ENST00000421437.1 | 0.029 | 0.265 | ENST00000440038.2 | 0.044 | 0.778 |
| ENST00000506655.1 | 0.011 | 0.812 | ENST00000504728.1 | 0.029 | 0.752 | ENST00000413841.1 | 0.044 | 0.752 |
| ENST00000526176.1 | 0.011 | 0.821 | ENST00000569928.1 | 0.029 | 0.239 | ENST00000489011.1 | 0.044 | 0.735 |
| ENST00000402410.2 | 0.011 | 0.761 | ENST00000421298.1 | 0.029 | 0.778 | ENST00000443562.1 | 0.044 | 0.795 |
| ENST00000455121.3 | 0.012 | 0.162 | ENST00000445565.1 | 0.030 | 0.769 | ENST00000512349.1 | 0.045 | 0.231 |
| ENST00000513660.2 | 0.012 | 0.769 | ENST00000598710.1 | 0.030 | 0.231 | ENST00000505736.1 | 0.045 | 0.231 |
| ENST00000602411.1 | 0.012 | 0.778 | ENST00000492209.1 | 0.030 | 0.786 | ENST00000442020.1 | 0.045 | 0.761 |
| ENST00000511222.1 | 0.012 | 0.752 | ENST00000492300.1 | 0.030 | 0.735 | ENST00000440862.1 | 0.045 | 0.205 |
| ENST00000607594.1 | 0.013 | 0.812 | ENST00000508484.1 | 0.030 | 0.248 | ENST00000464242.1 | 0.045 | 0.718 |
| ENST00000450500.1 | 0.013 | 0.786 | ENST00000415174.1 | 0.030 | 0.188 | ENST00000499900.2 | 0.045 | 0.231 |
| ENST00000439239.2 | 0.013 | 0.795 | ENST00000432505.1 | 0.031 | 0.761 | ENST00000457941.1 | 0.045 | 0.718 |
| ENST00000549878.1 | 0.013 | 0.761 | ENST00000523311.1 | 0.031 | 0.756 | ENST00000470263.1 | 0.045 | 0.761 |
| ENST00000418015.1 | 0.013 | 0.821 | ENST00000434796.1 | 0.031 | 0.735 | ENST00000512581.1 | 0.045 | 0.735 |
| ENST00000444217.1 | 0.013 | 0.786 | ENST00000440266.2 | 0.031 | 0.778 | ENST00000464428.2 | 0.045 | 0.752 |
| ENST00000435548.1 | 0.014 | 0.795 | ENST00000447876.1 | 0.031 | 0.239 | ENST00000523745.1 | 0.046 | 0.222 |
| ENST00000607026.1 | 0.014 | 0.188 | ENST00000506070.1 | 0.031 | 0.274 | ENST00000522173.1 | 0.046 | 0.214 |
| ENST00000503093.1 | 0.014 | 0.739 | ENST00000426083.1 | 0.032 | 0.248 | ENST00000585718.1 | 0.046 | 0.248 |
| ENST00000509184.1 | 0.014 | 0.821 | ENST00000576302.1 | 0.032 | 0.761 | ENST00000605147.1 | 0.046 | 0.188 |
| ENST00000443670.1 | 0.014 | 0.769 | ENST00000607950.1 | 0.032 | 0.778 | ENST00000509496.1 | 0.047 | 0.735 |
| ENST00000486767.1 | 0.015 | 0.786 | ENST00000588145.1 | 0.032 | 0.701 | ENST00000449298.1 | 0.047 | 0.769 |
| ENST00000457402.1 | 0.015 | 0.188 | ENST00000503259.1 | 0.032 | 0.761 | ENST00000456803.1 | 0.047 | 0.226 |
| ENST00000515789.1 | 0.015 | 0.197 | ENST00000454380.1 | 0.032 | 0.205 | ENST00000509212.1 | 0.048 | 0.256 |
| ENST00000429608.1 | 0.015 | 0.782 | ENST00000608925.1 | 0.032 | 0.239 | ENST00000442036.1 | 0.048 | 0.735 |
| ENST00000592182.1 | 0.016 | 0.786 | ENST00000608442.1 | 0.032 | 0.214 | ENST00000564300.1 | 0.048 | 0.239 |
| ENST00000422259.1 | 0.016 | 0.231 | ENST00000602470.1 | 0.032 | 0.739 | ENST00000426504.1 | 0.048 | 0.231 |
| ENST00000442200.1 | 0.016 | 0.786 | ENST00000514011.1 | 0.033 | 0.239 | ENST00000457686.1 | 0.049 | 0.205 |
| ENST00000432733.1 | 0.016 | 0.214 | ENST00000605589.1 | 0.033 | 0.735 | ENST00000515542.1 | 0.049 | 0.735 |
| ENST00000518276.1 | 0.016 | 0.744 | ENST00000497379.2 | 0.033 | 0.171 | ENST00000429469.1 | 0.050 | 0.701 |
| ENST00000420418.1 | 0.016 | 0.761 | ENST00000609352.1 | 0.034 | 0.752 | ENST00000443008.1 | 0.050 | 0.265 |
| ENST00000297163.3 | 0.016 | 0.744 | ENST00000507476.1 | 0.034 | 0.726 | ENST00000427524.1 | 0.034 | 0.778 |
| ENST00000453155.1 | 0.016 | 0.821 | | | | | | |

First, samples are grouped into 2 groups by a dichotomized variable: 1-month LVEF<45% and 1-month LVEF>45%.

243 lncRNA are differentially expressed and among these, 69 lncRNA are differentially expressed and have a fold change>2 or <0.5 between the low LVEF (LVEF≤45%) and the high LVEF (LVEF>45%). 2 lncRNAs are common to D3 samples (ENST00000429230.1, ENST00000599448.1). The p-value and the fold-change of these lncRNA are listed in the Table 40. 211 lncRNAs which have a p<0.05 and an individual AUC>0.7 or ≤0.3 are listed in Table 41.

TABLE 40

List of 76 lncRNA from Gencode database which are differentially expressed (p < 0.05) and have a fold change >2 or <0.5 between the low LVEF group (LVEF ≤ 45%) and the high LVEF group (LVEF > 45%)

| lncRNA | p Value | foldchange |
|---|---|---|
| ENST00000449154.1 | 0.000 | 3.558 |
| ENST00000523354.1 | 0.000 | 2.334 |
| ENST00000453015.1 | 0.000 | 0.356 |
| ENST00000435895.1 | 0.000 | 0.486 |
| ENST00000552026.1 | 0.001 | 3.770 |
| ENST00000415543.1 | 0.001 | 0.237 |
| ENST00000436488.1 | 0.001 | 0.431 |
| ENST00000599448.1 | 0.003 | 0.203 |
| ENST00000441345.2 | 0.005 | 0.117 |
| ENST00000430555.1 | 0.005 | 2.363 |
| ENST00000608111.1 | 0.006 | 17.287 |
| ENST00000607026.1 | 0.006 | 0.439 |
| ENST00000435643.1 | 0.006 | 0.249 |

TABLE 40-continued

List of 76 lncRNA from Gencode database which are differentially expressed (p < 0.05) and have a fold change >2 or <0.5 between the low LVEF group (LVEF ≤ 45%) and the high LVEF group (LVEF > 45%)

| lncRNA | p Value | foldchange |
|---|---|---|
| ENST00000597904.1 | 0.006 | 3.537 |
| ENST00000496733.2 | 0.007 | 0.488 |
| ENST00000607985.1 | 0.007 | 0.109 |
| ENST00000465283.1 | 0.007 | 0.082 |
| ENST00000429230.1 | 0.008 | 4.740 |
| ENST00000443562.1 | 0.008 | 2.248 |
| ENST00000461448.1 | 0.010 | 0.467 |
| ENST00000507698.1 | 0.010 | 2.574 |
| ENST00000594976.1 | 0.011 | 0.206 |
| ENST00000606468.1 | 0.011 | 2.875 |
| ENST00000431130.2 | 0.011 | 2.733 |
| ENST00000605147.1 | 0.012 | 0.351 |
| ENST00000469289.1 | 0.013 | 5.727 |
| ENST00000427042.1 | 0.013 | 2.802 |
| ENST00000413525.1 | 0.013 | 0.248 |
| ENST00000461864.1 | 0.014 | 0.440 |
| ENST00000439745.1 | 0.016 | 0.470 |
| ENST00000402410.2 | 0.017 | 6.982 |
| ENST00000507476.1 | 0.017 | 4.500 |
| ENST00000421563.1 | 0.018 | 2.113 |
| ENST00000515263.1 | 0.019 | 0.304 |
| ENST00000433475.1 | 0.019 | 9.721 |
| ENST00000436293.2 | 0.021 | 4.454 |
| ENST00000509057.1 | 0.022 | 2.111 |
| ENST00000457686.1 | 0.023 | 0.198 |
| ENST00000523895.1 | 0.024 | 0.435 |
| ENST00000419531.2 | 0.025 | 0.000 |

TABLE 40-continued

List of 76 lncRNA from Gencode database which are differentially expressed (p < 0.05) and have a fold change >2 or <0.5 between the low LVEF group (LVEF ≤ 45%) and the high LVEF group (LVEF > 45%)

| lncRNA | p Value | foldchange |
|---|---|---|
| ENST00000444361.1 | 0.025 | 0.254 |
| ENST00000601854.1 | 0.026 | 5.663 |
| ENST00000441036.1 | 0.026 | 2.509 |
| ENST00000505149.1 | 0.027 | 0.448 |
| ENST00000435492.1 | 0.030 | 0.316 |
| ENST00000512401.1 | 0.031 | 0.057 |
| ENST00000507842.1 | 0.032 | 2.843 |
| ENST00000510648.1 | 0.032 | 3.873 |
| ENST00000606314.1 | 0.033 | 3.833 |
| ENST00000474250.1 | 0.034 | 4.009 |
| ENST00000509105.1 | 0.034 | 8.823 |
| ENST00000588145.1 | 0.035 | 13.232 |
| ENST00000470860.1 | 0.035 | 0.238 |
| ENST00000485020.1 | 0.037 | 0.412 |
| ENST00000447876.1 | 0.037 | 0.323 |
| ENST00000426892.1 | 0.037 | 2.191 |
| ENST00000512603.1 | 0.039 | 0.433 |
| ENST00000602528.1 | 0.040 | 0.441 |
| ENST00000424788.1 | 0.040 | 0.169 |
| ENST00000424084.1 | 0.044 | 6.957 |
| ENST00000507639.1 | 0.044 | 3.312 |
| ENST00000426178.1 | 0.044 | 0.170 |
| ENST00000417516.1 | 0.044 | 2.784 |
| ENST00000416279.1 | 0.044 | 2.637 |
| ENST00000443270.1 | 0.044 | 3.375 |
| ENST00000469846.2 | 0.045 | 0.256 |
| ENST00000508998.1 | 0.047 | 3.937 |
| ENST00000598740.1 | 0.047 | 2.006 |
| ENST00000597654.1 | 0.047 | 0.068 |

TABLE 41

List of 211 lncRNA from Gencode database, which are differentially expressed (p < 0.05) and have an AUC > 0.7 or < 0.3 between the low LVEF group (LVEF ≤ 45%) and the high LVEF group (LVEF > 45%)

| lncRNA | p Value | auc | lncRNA | p Value | auc | lncRNA | p Value | auc |
|---|---|---|---|---|---|---|---|---|
| ENST00000449154.1 | 0.000 | 0.923 | ENST00000424748.1 | 0.016 | 0.803 | ENST00000471248.1 | 0.034 | 0.239 |
| ENST00000523354.1 | 0.000 | 0.897 | ENST00000514201.1 | 0.016 | 0.769 | ENST00000448379.1 | 0.034 | 0.735 |
| ENST00000453015.1 | 0.000 | 0.068 | ENST00000592948.1 | 0.017 | 0.214 | ENST00000543656.1 | 0.034 | 0.761 |
| ENST00000435895.1 | 0.000 | 0.068 | ENST00000450500.1 | 0.017 | 0.795 | ENST00000416080.1 | 0.034 | 0.752 |
| ENST00000552026.1 | 0.001 | 0.889 | ENST00000402410.2 | 0.017 | 0.821 | ENST00000474250.1 | 0.034 | 0.744 |
| ENST00000415543.1 | 0.001 | 0.128 | ENST00000417926.1 | 0.017 | 0.778 | ENST00000509105.1 | 0.034 | 0.744 |
| ENST00000436488.1 | 0.001 | 0.103 | ENST00000564407.1 | 0.017 | 0.222 | ENST00000608740.1 | 0.035 | 0.769 |
| ENST00000492300.1 | 0.002 | 0.872 | ENST00000507476.1 | 0.017 | 0.821 | ENST00000456327.1 | 0.035 | 0.744 |
| ENST00000506655.1 | 0.002 | 0.872 | ENST00000432711.1 | 0.018 | 0.795 | ENST00000588145.1 | 0.035 | 0.803 |
| ENST00000588227.1 | 0.002 | 0.838 | ENST00000421563.1 | 0.018 | 0.812 | ENST00000452901.1 | 0.035 | 0.786 |
| ENST00000432210.1 | 0.002 | 0.889 | ENST00000415342.1 | 0.019 | 0.222 | ENST00000499583.1 | 0.036 | 0.248 |
| ENST00000442020.1 | 0.002 | 0.872 | ENST00000430471.1 | 0.019 | 0.786 | ENST00000509559.1 | 0.036 | 0.256 |
| ENST00000414065.1 | 0.002 | 0.829 | ENST00000515263.1 | 0.019 | 0.205 | ENST00000514608.1 | 0.036 | 0.214 |
| ENST00000599448.1 | 0.003 | 0.188 | ENST00000433475.1 | 0.019 | 0.872 | ENST00000485020.1 | 0.037 | 0.291 |
| ENST00000496154.2 | 0.004 | 0.137 | ENST00000507056.1 | 0.019 | 0.248 | ENST00000447876.1 | 0.037 | 0.282 |
| ENST00000444672.1 | 0.004 | 0.872 | ENST00000428647.1 | 0.019 | 0.786 | ENST00000608851.1 | 0.037 | 0.265 |
| ENST00000440786.1 | 0.005 | 0.829 | ENST00000492307.1 | 0.020 | 0.803 | ENST00000426892.1 | 0.037 | 0.752 |
| ENST00000356133.3 | 0.005 | 0.855 | ENST00000507781.1 | 0.020 | 0.291 | ENST00000606200.1 | 0.037 | 0.752 |
| ENST00000514010.1 | 0.005 | 0.855 | ENST00000522173.1 | 0.020 | 0.205 | ENST00000425176.1 | 0.037 | 0.295 |
| ENST00000441345.2 | 0.005 | 0.111 | ENST00000521803.1 | 0.020 | 0.795 | ENST00000601136.1 | 0.037 | 0.829 |
| ENST00000603264.1 | 0.005 | 0.162 | ENST00000448129.1 | 0.021 | 0.197 | ENST00000438978.1 | 0.038 | 0.761 |
| ENST00000602433.1 | 0.005 | 0.205 | ENST00000436293.2 | 0.021 | 0.855 | ENST00000510254.1 | 0.038 | 0.214 |
| ENST00000430555.1 | 0.005 | 0.846 | ENST00000506425.1 | 0.021 | 0.214 | ENST00000423410.1 | 0.038 | 0.752 |
| ENST00000428083.1 | 0.006 | 0.838 | ENST00000422841.1 | 0.021 | 0.222 | ENST00000512603.1 | 0.039 | 0.265 |
| ENST00000608111.1 | 0.006 | 0.915 | ENST00000431244.1 | 0.022 | 0.222 | ENST00000414120.1 | 0.040 | 0.282 |
| ENST00000607026.1 | 0.006 | 0.248 | ENST00000509057.1 | 0.022 | 0.786 | ENST00000602528.1 | 0.040 | 0.265 |
| ENST00000435643.1 | 0.006 | 0.188 | ENST00000430520.1 | 0.023 | 0.222 | ENST00000414625.2 | 0.040 | 0.239 |
| ENST00000597904.1 | 0.006 | 0.880 | ENST00000457686.1 | 0.023 | 0.282 | ENST00000502410.1 | 0.040 | 0.778 |
| ENST00000496733.2 | 0.007 | 0.188 | ENST00000429315.3 | 0.023 | 0.744 | ENST00000601940.1 | 0.041 | 0.239 |
| ENST00000446520.1 | 0.007 | 0.188 | ENST00000523895.1 | 0.024 | 0.222 | ENST00000505162.1 | 0.041 | 0.744 |
| ENST00000607985.1 | 0.007 | 0.235 | ENST00000504728.1 | 0.024 | 0.752 | ENST00000492209.1 | 0.041 | 0.786 |
| ENST00000465283.1 | 0.007 | 0.261 | ENST00000607148.1 | 0.025 | 0.214 | ENST00000427748.1 | 0.042 | 0.239 |
| ENST00000421933.1 | 0.007 | 0.162 | ENST00000326734.1 | 0.025 | 0.248 | ENST00000522975.1 | 0.042 | 0.726 |
| ENST00000499346.2 | 0.007 | 0.812 | ENST00000428624.1 | 0.025 | 0.222 | ENST00000606855.1 | 0.042 | 0.744 |
| ENST00000429230.1 | 0.008 | 0.786 | ENST00000419531.2 | 0.025 | 0.214 | ENST00000508031.1 | 0.043 | 0.744 |
| ENST00000443562.1 | 0.008 | 0.846 | ENST00000564261.1 | 0.026 | 0.769 | ENST00000609032.1 | 0.043 | 0.231 |
| ENST00000435692.2 | 0.009 | 0.846 | ENST00000601854.1 | 0.026 | 0.735 | ENST00000446073.1 | 0.043 | 0.761 |
| ENST00000461448.1 | 0.010 | 0.179 | ENST00000566904.1 | 0.026 | 0.812 | ENST00000424084.1 | 0.044 | 0.778 |
| ENST00000522312.1 | 0.010 | 0.197 | ENST00000441036.1 | 0.026 | 0.812 | ENST00000507639.1 | 0.044 | 0.718 |
| ENST00000425776.1 | 0.010 | 0.872 | ENST00000442036.1 | 0.026 | 0.786 | ENST00000413531.1 | 0.044 | 0.274 |
| ENST00000512349.1 | 0.010 | 0.162 | ENST00000594101.1 | 0.026 | 0.239 | ENST00000434346.1 | 0.044 | 0.299 |
| ENST00000507698.1 | 0.010 | 0.816 | ENST00000335577.4 | 0.026 | 0.786 | ENST00000417516.1 | 0.044 | 0.803 |
| ENST00000425896.1 | 0.010 | 0.769 | ENST00000607594.1 | 0.027 | 0.778 | ENST00000416279.1 | 0.044 | 0.795 |
| ENST00000594976.1 | 0.011 | 0.299 | ENST00000510165.1 | 0.027 | 0.214 | ENST00000443270.1 | 0.044 | 0.795 |
| ENST00000606468.1 | 0.011 | 0.812 | ENST00000505149.1 | 0.027 | 0.282 | ENST00000436262.1 | 0.045 | 0.222 |
| ENST00000517595.1 | 0.011 | 0.205 | ENST00000507681.1 | 0.027 | 0.222 | ENST00000503179.1 | 0.046 | 0.231 |
| ENST00000431130.2 | 0.011 | 0.821 | ENST00000417636.1 | 0.027 | 0.795 | ENST00000510240.1 | 0.046 | 0.256 |

TABLE 41-continued

List of 211 lncRNA from Gencode database, which are differentially expressed (p < 0.05) and have an
AUC > 0.7 or < 0.3 between the low LVEF group (LVEF ≤ 45%) and the high LVEF group (LVEF > 45%)

| lncRNA | p Value | auc | lncRNA | p Value | auc | lncRNA | p Value | auc |
|---|---|---|---|---|---|---|---|---|
| ENST00000507627.1 | 0.011 | 0.812 | ENST00000605082.1 | 0.028 | 0.752 | ENST00000607744.1 | 0.046 | 0.231 |
| ENST00000515842.1 | 0.012 | 0.179 | ENST00000438623.1 | 0.028 | 0.222 | ENST00000512428.1 | 0.046 | 0.274 |
| ENST00000435880.2 | 0.012 | 0.197 | ENST00000470263.1 | 0.028 | 0.778 | ENST00000511390.1 | 0.046 | 0.774 |
| ENST00000432267.2 | 0.012 | 0.812 | ENST00000509641.2 | 0.029 | 0.752 | ENST00000456519.1 | 0.046 | 0.274 |
| ENST00000528818.1 | 0.012 | 0.205 | ENST00000607804.1 | 0.029 | 0.786 | ENST00000506950.1 | 0.047 | 0.265 |
| ENST00000512417.1 | 0.012 | 0.812 | ENST00000435492.1 | 0.030 | 0.226 | ENST00000598740.1 | 0.047 | 0.744 |
| ENST00000605147.1 | 0.012 | 0.171 | ENST00000431139.2 | 0.030 | 0.769 | ENST00000520041.1 | 0.047 | 0.752 |
| ENST00000469289.1 | 0.013 | 0.855 | ENST00000425275.1 | 0.030 | 0.214 | ENST00000417927.1 | 0.047 | 0.282 |
| ENST00000444721.1 | 0.013 | 0.812 | ENST00000428176.1 | 0.030 | 0.265 | ENST00000523311.1 | 0.047 | 0.756 |
| ENST00000507653.1 | 0.013 | 0.179 | ENST00000505109.1 | 0.031 | 0.769 | ENST00000432395.1 | 0.047 | 0.214 |
| ENST00000427042.1 | 0.013 | 0.829 | ENST00000504207.1 | 0.031 | 0.231 | ENST00000502467.1 | 0.047 | 0.248 |
| ENST00000584829.1 | 0.013 | 0.803 | ENST00000512401.1 | 0.031 | 0.226 | ENST00000609166.1 | 0.047 | 0.744 |
| ENST00000454595.1 | 0.013 | 0.821 | ENST00000517916.1 | 0.031 | 0.752 | ENST00000609005.1 | 0.047 | 0.761 |
| ENST00000413525.1 | 0.013 | 0.218 | ENST00000511213.1 | 0.031 | 0.778 | ENST00000444042.2 | 0.047 | 0.795 |
| ENST00000418050.1 | 0.014 | 0.821 | ENST00000567486.2 | 0.031 | 0.761 | ENST00000511616.1 | 0.048 | 0.282 |
| ENST00000453569.1 | 0.014 | 0.222 | ENST00000507842.1 | 0.032 | 0.769 | ENST00000426539.1 | 0.048 | 0.299 |
| ENST00000461864.1 | 0.014 | 0.162 | ENST00000510648.1 | 0.032 | 0.786 | ENST00000412204.2 | 0.048 | 0.735 |
| ENST00000608056.1 | 0.015 | 0.171 | ENST00000513851.1 | 0.032 | 0.752 | ENST00000436950.1 | 0.048 | 0.761 |
| ENST00000439745.1 | 0.016 | 0.226 | ENST00000430677.1 | 0.032 | 0.256 | ENST00000496220.1 | 0.048 | 0.726 |
| ENST00000470739.1 | 0.016 | 0.197 | ENST00000452283.1 | 0.032 | 0.726 | ENST00000569928.1 | 0.049 | 0.239 |
| ENST00000569694.1 | 0.016 | 0.162 | ENST00000606314.1 | 0.033 | 0.803 | ENST00000433108.1 | 0.049 | 0.752 |
| ENST00000314957.3 | 0.016 | 0.752 | ENST00000426702.1 | 0.033 | 0.256 | ENST00000507398.1 | 0.049 | 0.274 |
| ENST00000513304.1 | 0.016 | 0.179 | ENST00000451396.2 | 0.033 | 0.735 | ENST00000414199.1 | 0.049 | 0.769 |
| ENST00000452176.1 | 0.034 | 0.786 | | | | | | |

The lncRNAs listed can be used as biomarkers for the prediction of Left Ventricular Remodeling and as therapeutics targets to prevent development of Heart Failure.

SEQUENCE LISTING

The patent contains a lengthy sequence listing. A copy of the sequence listing is available in electronic form from the USPTO web site (https://seqdata.uspto.gov/?pageRequest=docDetail&DocID=US11667974B2). An electronic copy of the sequence listing will also be available from the USPTO upon request and payment of the fee set forth in 37 CFR 1.19(b)(3).

The invention claimed is:

1. A method of detecting a level of expression of one or more lncRNAs in a subject, the method comprising
   (a) obtaining a biological sample from said subject; and
   (b) detecting the level of expression of one or more lncRNAs in the sample, wherein the one or more lncRNAs comprise 20 lncRNAs of SEQ ID NO: 0190, SEQ ID NO: 0359, SEQ ID NO: 0776, SEQ ID NO: 1421, SEQ ID NO: 1795, SEQ ID NO: 0477, SEQ ID NO: 1511, SEQ ID NO: 0435, SEQ ID NO: 1418, SEQ ID NO: 1025, SEQ ID NO: 0265, SEQ ID NO: 1311, SEQ ID NO: 2540, SEQ ID NO: 2323, SEQ ID NO: 3011, SEQ ID NO: 2447, SEQ ID NO: 2863, SEQ ID NO: 2697, SEQ ID NO: 3128, and SEQ ID NO: 2265.

2. The method of claim 1, wherein the biological sample is selected from the group consisting of: whole blood, serum, and plasma.

3. The method of claim 1, wherein the lncRNA expression levels are detected in the biological sample using a technique selected from the group consisting of: polymerase chain reaction (PCR), reverse transcriptase polymerase chain reaction (RT-PCR), and reverse transcriptase quantitative polymerase chain reaction (RT-qPCR).

4. The method of claim 1, wherein the expression levels of the lncRNAs in the biological sample are detected using a singleplexed or multiplexed method.

5. The method of claim 1, wherein the expression levels of the lncRNAs in the biological sample are detected by measuring the levels of cDNAs, amplified RNAs or DNAs, or quantities of DNA probes that are indicative of the expression levels of the lncRNAs.

6. A kit for diagnosing heart failure with reduced ejection fraction (HFrEF), comprising at least one reagent for the determination of expression levels of one or more lncRNAs, wherein the one or more lncRNAs comprise 20 lncRNAs of SEQ ID NO: 0190, SEQ ID NO: 0359, SEQ ID NO: 0776, SEQ ID NO: 1421, SEQ ID NO: 1795, SEQ ID NO: 0477, SEQ ID NO: 1511, SEQ ID NO: 0435, SEQ ID NO: 1418, SEQ ID NO: 1025, SEQ ID NO: 0265, SEQ ID NO: 1311, SEQ ID NO: 2540, SEQ ID NO: 2323, SEQ ID NO: 3011, SEQ ID NO: 2447, SEQ ID NO: 2863, SEQ ID NO: 2697, SEQ ID NO: 3128, and SEQ ID NO: 2265, wherein the kit comprises:
   (i) one or more oligonucleotide probes comprising a sequence complementary to a region of the one or more lncRNAs which form one or more probe-target nucleic acid complexes; and (ii) a reagent for purifying the probe-target nucleic acid complexes, and wherein the oligonucleotide probes are biotinylated.

7. The kit of claim 6, wherein the reagent for purifying the probe-target complexes is a streptavidin-coated substrate.

8. The method of claim 1, wherein the biological sample is cardiac tissue.

9. The method of claim 1, wherein the biological sample is PBMC (peripheral blood mononuclear cell).

10. The method of claim 1, wherein the lncRNA expression levels are detected in the biological sample using microarray analysis.

11. The method of claim 1, wherein the lncRNA expression levels are detected in the biological sample using serial analysis of gene expression (SAGE).

12. The method of claim 1, wherein the lncRNA expression levels are detected in the biological sample using Northern blot analysis.

13. The method of claim 1, wherein the lncRNA expression levels are detected in the biological sample using 51 nuclease protection assay.

14. The method of claim 1, wherein the lncRNA expression levels are detected in the biological sample using a hybridization technology.

15. The method of claim 1, wherein the lncRNA expression levels are detected in the biological sample using next generation sequencing.

16. The kit of claim 7, wherein the streptavidin-coated substrate is a streptavidin-coated magnetic particle.

* * * * *